(12) United States Patent
Arthur

(10) Patent No.: US 8,790,632 B2
(45) Date of Patent: Jul. 29, 2014

(54) POLYMER-BASED TISSUE-ADHESIVE FORM MEDICAL USE

(75) Inventor: Samuel David Arthur, Wilmington, DE (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 2271 days.

(21) Appl. No.: 11/244,758

(22) Filed: Oct. 5, 2005

(65) Prior Publication Data
US 2006/0079599 A1    Apr. 13, 2006

Related U.S. Application Data

(60) Provisional application No. 60/616,853, filed on Oct. 7, 2004.

(51) Int. Cl.
*A61K 31/74* (2006.01)
*A61L 24/04* (2006.01)
*A61L 24/00* (2006.01)

(52) U.S. Cl.
CPC ............. *A61L 24/046* (2013.01); *A61L 24/043* (2013.01); *A61L 24/0031* (2013.01)
USPC .................................... 424/78.17; 424/78.08

(58) Field of Classification Search
USPC ...................................................... 424/78.31
See application file for complete search history.

(56) References Cited

U.S. PATENT DOCUMENTS

| | | | |
|---|---|---|---|
| 3,029,187 A * | 4/1962 | Steinhardt et al. | 424/94.62 |
| 3,361,585 A * | 1/1968 | Armour et al. | 106/207.5 |
| 4,584,188 A | 4/1986 | Graham | |
| 4,708,821 A | 11/1987 | Shimokawa et al. | |
| 5,116,824 A | 5/1992 | Miyata et al. | |
| 5,162,430 A | 11/1992 | Rhee et al. | |
| 5,203,914 A * | 4/1993 | Futami et al. | 106/35 |
| 5,275,838 A | 1/1994 | Merrill | |
| 5,292,802 A | 3/1994 | Rhee et al. | |
| 5,308,889 A | 5/1994 | Rhee et al. | |
| 5,324,775 A | 6/1994 | Rhee et al. | |
| 5,328,995 A | 7/1994 | Schaulin et al. | |
| 5,505,952 A | 4/1996 | Jiang et al. | |
| 5,514,379 A | 5/1996 | Weissleder et al. | |
| 5,643,575 A | 7/1997 | Martinez et al. | |
| 5,733,563 A | 3/1998 | Fortier | |
| 5,874,500 A | 2/1999 | Rhee et al. | |
| 6,184,284 B1 * | 2/2001 | Stokich et al. | 524/500 |
| 6,620,125 B1 | 9/2003 | Redl | |
| 2001/0056137 A1 * | 12/2001 | Buter et al. | 523/414 |
| 2002/0136769 A1 | 9/2002 | Kabanov et al. | |
| 2005/0002893 A1 * | 1/2005 | Goldmann | 424/70.27 |
| 2006/0078536 A1 | 4/2006 | Kodokian et al. | |
| 2006/0079599 A1 | 4/2006 | Arthur | |
| 2007/0048251 A1 | 3/2007 | Arthur | |
| 2007/0048337 A1 | 3/2007 | Arthur | |

FOREIGN PATENT DOCUMENTS

| | | |
|---|---|---|
| FR | 2099308 | 4/1972 |
| JP | 1982-102932 | 6/1982 |
| JP | 1988-11167 | 1/1988 |
| JP | 05020458 | 3/1993 |
| WO | WO 91/15368 | 10/1991 |
| WO | WO 97/22371 | 6/1997 |
| WO | WO 00/62827 | 10/2000 |
| WO | WO 01/16210 | 3/2001 |
| WO | WO 01/49268 | 7/2001 |
| WO | WO 03/020818 | 3/2003 |
| WO | WO 03/035122 | 5/2003 |

OTHER PUBLICATIONS

Search Report for International Application No. PCT/US2005/036270.
Kondo, et al., "Immobilization of Biocatalysts Using Crosslinked Acetoacetyl Poly(vinyl alcohol) Hydrogels", Hakko Koganku Kaishi, vol. 69, No. 5, (1991), pp. 337-344—Abstract Only.
Pfannemuller, B., et al., "Chemical Modification of the Surface of the Starch Granules", Starch/Starke, vol. 95, No. 9, 1983, pp. 298-303.

* cited by examiner

*Primary Examiner* — James Rogers
(74) *Attorney, Agent, or Firm* — McCarter & English

(57) ABSTRACT

Tissue adhesives formed by reacting poly(hydroxylic) compounds derivatized with acetoacetate groups and/or polyamino compounds derivatized with acetoacetamide groups with an amino-functional crosslinking compound are disclosed.

The use of the tissue adhesives for medical and veterinary applications such as topical wound closure; and surgical procedures, such as intestinal anastomosis, vascular anastomosis, tissue repair, and ophthalmic procedures; drug delivery; and anti-adhesive applications are described.

21 Claims, No Drawings

POLYMER-BASED TISSUE-ADHESIVE FORM MEDICAL USE

CROSS-REFERENCE TO RELATED APPLICATION

This application claims priority under 35 U.S.C. §119 from U.S. Provisional Application Ser. No. 60/616,853, filed Oct. 7, 2004.

FIELD OF THE INVENTION

The invention relates to the field of medical adhesives. More specifically, the invention relates to a polymer-based tissue-adhesive formed by reacting poly(hydroxylic) compounds derivatized with acetoacetate groups and/or polyamino compounds derivatized with acetoacetamide groups with an amino-functional crosslinking compound.

BACKGROUND

Tissue adhesives have many potential medical applications, including topical wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of infection. Additionally, the Fibrin-based adhesives do not covalently bind to the underlying tissue.

Several types of hydrogel tissue adhesives that have improved adhesive and cohesive properties and are nontoxic have been developed. These hydrogels are generally formed by reacting a component having nucleophilic groups with a component having electrophilic groups to form a covalently crosslinked network. However, these hydrogels are not very effective as surgical adhesives because they typically swell excessively upon the intake of aqueous media, dissolve away at a rate faster than necessary, or lack sufficient adhesion or mechanical strength.

Hydrogels comprising acetoacetate esters crosslinked with amino groups have not been used as tissue adhesives in medical applications. For example, U.S. Pat. No. 4,708,821 describes a process for preparing an aqueous gel which comprises mixing a water-soluble acetoacetylated high molecular compound and a compound containing an amino group in water. Such an aqueous gel is deemed for usage in perfumes and deodorants. The '821 patent does not describe acetoacetylated compound cross-linked with compounds comprising amino groups for medical applications and specifically, for applications related to tissue adhesives.

The main hydrogel bioadhesive polymers known in the art are polyethers or proteins such as albumin. The polyethers are limited in functionality to their end groups, while animal- or human-derived proteins have viral transmission issues. Additionally, the reactive crosslinkable polyether end groups in the art are either photoreactive, requiring the awkward use of a curing lamp, or else they are activated esters that hydrolyze quickly in aqueous solution, or thiols which easily air-oxidize to unreactive disulfides.

Poly(hydroxylic) compounds derivatized with acetoacetate groups and/or polyamino compounds derivatized with acetoacetamide groups by themselves or the combination of these compounds crosslinked with an amino-functional crosslinking compound have not been used for bioadhesive applications.

Applicants' invention addresses the use of an acetoacetylated compound and/or a polyamino compound derivatized with acetoacetamide groups, cross-linked with compounds comprising amino groups for medical applications and specifically for applications related to tissue adhesives. The invention provides a tissue adhesive material with improved characteristics for use in surgical procedures as well as other medical applications. The resulting adhesive has improved adhesion and cohesion to biological substrates (e.g., collagen, muscle tissue), crosslinks readily at body temperature, maintains dimensional stability, does not degrade rapidly, is nontoxic to cells and non-inflammatory to tissue. Additionally, the adhesive has good aqueous and air stability and fast gelation time.

Furthermore, unlike the polyethers in the art, poly(hydroxylic) compounds can be easily converted to the acetoacetate derivative and polyamino compounds can be readily converted to the acetoacetamide derivative at virtually any substitution level, resulting in the ability to tailor reactivity with amino-functional crosslinking compounds and the final hydrogel crosslink density. Unlike the activated ester groups in the polyether art, acetoacetate groups and acetoacetamide groups are stable in water indefinitely. The acetoacetate group is easy to add to many hydroxy-containing organic molecules, rendering a large variety of poly(hydroxylic) compounds useful for amine-crosslinked bioadhesive application. Similarly, the acetoacetamide group is easy to add to many amino-containing organic molecules, rendering a variety of polyamino compounds useful for amine-crosslinked bioadhesive application.

SUMMARY OF THE INVENTION

The invention provides a kit comprising:
a) a first component comprising:
a first aqueous solution comprising at least one material selected from the group consisting of
  at least one linear or branched poly(ether) derivatized with acetoacetate groups;
  at least one polysaccharide derivatized with acetoacetate groups wherein said polysaccharide is other than starch, starch derivatives, cellulose, and cellulose derivatives;
  at least one low molecular weight polyol derivatized with acetoacetate groups wherein said polyol has at least two hydroxy groups and has a molecular weight of less than about 300 Daltons;
  at least one hydrolyzed polyvinyl acetate-methyl acrylate copolymer derivatized with acetoacetate groups;
  at least one monosaccharide derivatized with acetoacetate groups;
  at least one reduced monosaccharide derivatized with acetoacetate groups;
  at least one polyether condensation product derivatized with acetoacetate groups wherein said polyether condensation product is produced by reacting at least one core molecule bearing more than one carboxylic acid group thereon with a sufficient amount of at least one polyether terminated with hydroxy groups to produce an esterified polyether with an average of at least two hydroxy end groups;

at least one first polyamino compound derivatized with acetoacetamide groups; and mixtures thereof;

said material each having a weight-average molecular weight of less than about 200,000 Daltons, and an equivalent weight per acetoacetate group or acetoacetamide group of about 100 to about 2000 Daltons;

said first aqueous solution containing at least about 5% by weight of said material; and b) a second component comprising:

at least one of (i) a second aqueous solution of at least one second polyamino compound that may be the same or different from said first polyamino compound;

(ii) at least one 3-aminopropyltrialkoxysilane, 3-aminopropyldialkoxyalkylsilane or 3-aminopropylmonoalkoxydialkylsilane, neat, or in aqueous solution; and (iii) an aqueous solution of said at least one second polyamino compound and at least one 3-aminopropyltrialkoxysilane, 3-aminopropyldialkoxyalkylsilane or 3-aminopropylmonoalkoxydialkylsilane;

wherein said at least one second polyamino compound has an equivalent weight per amino group of about 100 to about 1,000 Daltons, and said second aqueous solution contains from about 5% to about 50% by weight of said at least one second polyamino compound;

provided that if said second component is (i), then said kit may further comprise a third component comprising at least one 3-aminopropyltrialkoxysilane, 3-aminopropyldialkoxyalkylsilane or 3-aminopropylmonoalkoxydialkylsilane, neat, or in aqueous solution; and (c) optionally, a fourth component comprising an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said solution containing from about 2% to about 40% by weight of the oxidized polysaccharide.

In another embodiment, the invention provides a method for applying a coating to an anatomical site on tissue of a living organism comprising:

(a) optionally priming said anatomical site with an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said solution containing from about 2% to about 40% by weight of the oxidized polysaccharide;

(b) applying to said anatomical site a first component comprising an aqueous solution comprising (i) at least one poly(hydroxylic) compound derivatized with acetoacetate groups and/or (ii) a first polyamino compound derivatized with acetoacetamide groups, each of (i) or (ii) having a weight-average molecular weight of less than about 200,000 Daltons and having an equivalent weight per acetoacetate group or acetoacetamide group, respectively, of about 100 to about 2000 Daltons; and (c) applying to said anatomical site a second component comprising at least one of (iii) an aqueous solution of at least one second polyamino compound that may be same or different from said first polyamino compound, (iv) at least one 3-aminopropyltrialkoxysilane, 3-aminopropyldialkoxyalkylsilane or 3-aminopropylmonoalkoxydialkylsilane, neat or in aqueous solution, and (v) an aqueous solution of at least one second polyamino compound and at least one 3-aminopropyltrialkoxysilane, 3-aminopropyldialkoxyalkylsilane or 3-aminopropylmonoalkoxydialkylsilane, wherein said at least one second polyamino compound has an equivalent weight per amino group of about 100 to about 1,000 Daltons; and (d) mixing said components on the surface of said anatomical site; or (e) applying said second component to said anatomical site, followed by said first component, followed by mixing the solutions on the surface of said anatomical site; or (f) premixing said first and second components, and applying the resulting mixture to said anatomical site before said resulting mixture completely cures;

provided that a third component comprising at least one 3-aminopropyltrialkoxysilane, 3-aminopropyldialkoxyalkylsilane or 3-aminopropylmonoalkoxydialkylsilane, neat or in aqueous solution, may be applied to said anatomical site at substantially the same time as said second component is applied to said anatomical site.

In another embodiment, the invention provides a method for bonding at least two anatomical sites together comprising:

(a) optionally priming at least one anatomical site with an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said solution containing from about 2% to about 40% by weight of the oxidized polysaccharide;

(b) applying a first component to at least one anatomical site comprising an aqueous solution comprising (i) at least one poly(hydroxylic) compound derivatized with acetoacetate groups and/or (ii) a first polyamino compound derivatized with acetoacetamide groups, each of (i) or (ii) having a weight-average molecular weight of less than about 200,000 Daltons and having an equivalent weight per acetoacetate group or acetoacetamide group, respectively, of about 100 to about 2000 Daltons;

(c) applying to said at least one anatomical site a second component comprising at least one of (iii) an aqueous solution of at least one second polyamino compound that may be same or different from said first polyamino compound;

(iv) at least one 3-aminopropyltrialkoxysilane, 3-aminopropyldialkoxyalkylsilane or 3-aminopropylmonoalkoxydialkylsilane, neat or in aqueous solution; and (v) an aqueous solution of at least one polyamino compound and at least one 3-aminopropyltrialkoxysilane, 3-aminopropyldialkoxyalkylsilane or 3-aminopropylmonoalkoxydialkylsilane, wherein said polyamino compound has an equivalent weight per amino group of about 100 to about 1,000 Daltons;

(d) mixing said components on the surface of said at least one anatomical site; or (e) applying said second component to said at least one anatomical site, followed by said first component, followed by mixing the solutions on the surface of said at least one anatomical site; or (f) premixing said first and second components, and applying the resulting mixture to said at least one anatomical site before said resulting mixture completely cures;

provided that a third component comprising at least one 3-aminopropyltrialkoxysilane, 3-aminopropyldialkoxyalkylsilane or 3-aminopropylmonoalkoxydialkylsilane, neat or in aqueous solution, may be applied to said at least one anatomical site at substantially the same time as said second component is applied to said at least one anatomical site; and (g) contacting said at least two anatomical sites together.

In another embodiment, the invention provides a composition comprising the reaction product of:

a) a first component comprising:

a first aqueous solution comprising at least one material selected from the group consisting of at least one linear or branched poly(ether) derivatized with acetoacetate groups;

at least one polysaccharide derivatized with acetoacetate groups wherein said polysaccharide is other than starch, starch derivatives, cellulose, and cellulose derivatives;

at least one low molecular weight polyol derivatized with acetoacetate groups wherein said polyol has at least two hydroxy groups and has a molecular weight of less than 300 Daltons;

at least one hydrolyzed polyvinyl acetate-methyl acrylate copolymer derivatized with acetoacetate groups;

at least one monosaccharide derivatized with acetoacetate groups;

at least one reduced monosaccharide derivatized with acetoacetate groups;

at least one polyether condensation product derivatized with acetoacetate groups wherein said polyether condensation product is produced by reacting at least one core molecule bearing more than one carboxylic acid group thereon with a sufficient amount of at least one polyether terminated with hydroxy groups to produce an esterified polyether with an average of at least two hydroxy end groups;

at least one first polyamino compound derivatized with acetoacetamide groups; and mixtures thereof;

said material each having a weight-average molecular weight of less than about 200,000 Daltons, and an equivalent weight per acetoacetate group or acetoacetamide group of about 100 to about 2000 Daltons;

said first aqueous solution containing at least about 5% by weight of said material; and b) a second component comprising:

at least one of (i) a second aqueous solution of at least one second polyamino compound that may be the same or different from said first polyamino compound;

(ii) at least one 3-aminopropyltrialkoxysilane, 3-aminopropyldialkoxyalkylsilane or 3-aminopropylmonoalkoxydialkylsilane, neat, or in aqueous solution; and (iii) an aqueous solution of said at least one second polyamino compound, and at least one 3-aminopropyltrialkoxysilane, 3-aminopropyldialkoxyalkylsilane or 3-aminopropylmonoalkoxydialkylsilane;

wherein said at least one second polyamino compound has an equivalent weight per amino group of about 100 to about 1,000 Daltons, and said second aqueous solution contains from about 5% to about 50% by weight of said at least one second polyamino compound;

provided that if said second component is (i), then said kit may further comprise a third component comprising at least one 3-aminopropyltrialkoxysilane, 3-aminopropyldialkoxyalkylsilane or 3-aminopropylmonoalkoxydialkylsilane, neat, or in aqueous solution; and (c) optionally, a fourth component comprising an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said solution containing from about 2% to about 40% by weight of the oxidized polysaccharide.

Methods for using the polymer tissue adhesive of the invention for topical wound closure, intestinal and vascular anastomoses, sealing corneal incisions, preventing adhesions, and drug delivery are also provided.

Additionally, the following compositions are also provided: a composition comprising dextran derivatized with acetoacetate groups, a composition comprising a linear or branched polyether derivatized with acetoacetate groups, a composition comprising a polyamino compound derivatized with acetoacetamide groups, a composition comprising a polyether condensation product derivatized with acetoacetate groups, a composition comprising a monosaccharide derivatized with acetoacetate groups, a composition comprising a reduced monosaccharide derivatized with acetoacetate groups, a composition comprising a low molecular weight polyol derivatized with acetoacetate groups, and a composition comprising a hydrolyzed polyvinylacetate-methyl acrylate copolymer derivatized with acetoacetate groups.

DETAILED DESCRIPTION OF THE INVENTION

The invention relates to a polymer-based tissue adhesive formed by reacting poly(hydroxylic) compounds derivatized with acetoacetate groups and/or polyamino compounds derivatized with acetoacetamide groups with a crosslinking agent comprising an amino functional group. The polymer adhesive of the invention is useful as an adhesive for medical applications including, but not limited to, topical wound closure, and surgical procedures, such as intestinal anastomosis, venous anastomosis, tissue repair, and ophthalmic procedures. Additionally, the polymer adhesive may have utility in drug delivery, and anti-adhesive applications.

The following definitions are used herein and should be referred to for interpretation of the claims and the specification.

The term "polyether" refers to a polymer having the repeat unit [—O—R]—, wherein R is a hydrocarbyl group having 2 to 5 carbon atoms.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to polyether having a single branch point from which linear arms emanate.

The term "hyperbranched polyether" refers to a highly branched polyether having fewer branches and less regular branching than a dendritic polyether.

The term "poly(hydroxylic)" compound refers to a chemical having at least two hydroxyl groups.

The term "polyamino compound" refers to a chemical having at least two primary amine groups.

The term "oxidized polysaccharide" refers to a polysaccharide that has been reacted with an oxidizing agent to introduce aldehyde groups into the molecule.

The term "dextran aldehyde" refers to dextran that has been reacted with an oxidizing agent to introduce aldehyde groups into the molecule.

The terms "equivalent weight per acetoacetate group", "equivalent weight per acetoacetamide group", "equivalent weight per amino group", and "equivalent weight per aldehyde group" refer to the molecular weight of the compound divided by the number of acetoacetate, acetoacetamide, amino or aldehyde groups, respectively, in the molecule.

The term "% by weight" as used herein refers to the weight percent relative to the total weight of the solution, unless otherwise specified.

The term "anatomical site" refers to any external or internal part of the body of human or animals.

The term "tissue" refers to any tissue, both living and dead, in humans or animals.

The term "hydrogel" refers to a water-swellable polymeric matrix, consisting of a three-dimensional network of macromolecules held together by covalent or non-covalent crosslinks, that can absorb a substantial amount of water to form an elastic gel.

By medical application is meant medical applications as related to humans and for veterinary purposes.

The invention provides a tissue adhesive formed by reacting poly(hydroxylic) compounds derivatized with acetoacetate groups and/or polyamino compounds derivatized with acetoacetamide groups with a crosslinking agent comprising an amino functional group. The reaction forms a hydrogel, which has many desirable characteristics as a tissue adhesive, including, but not limited to, improved adhesion and cohesion to biological substrates (e.g., collagen, muscle tissue), crosslinks readily at body temperature, maintains dimensional stability, does not degrade rapidly, is nontoxic to cells and non-inflammatory to tissue. Additionally, the adhesive has good aqueous and air stability and fast gelation time.

Poly(Hydroxylic) Compounds Derivatized with Acetoacetate Groups

A wide variety of poly(hydroxylic) compounds may be derivatized with acetoacetate groups and used in the invention. Typically, the weight-average molecular weight of useful poly(hydroxylic) compounds is less than about 200,000 Daltons. Suitable examples include, but are not limited to, poly(vinyl alcohol), poly(vinyl alcohol) copolymers, linear or branched polyethers, polysaccharides, monosaccharides, reduced monosaccharides, low molecular weight polyols, hydrolyzed polyvinyl acetate-methacrylate copolymers, polyether condensation products, and mixtures thereof.

In one embodiment, at least one poly(vinyl alcohol) is used as the poly(hydroxylic) compound that is derivatized with acetoacetate groups. Poly(vinyl alcohols) having different molecular weights and varying degrees of hydrolysis are available commercially from companies such as Sigma-Aldrich (St. Louis, Mo.). Poly(vinyl alcohols) suitable for use in the invention have a weight-average molecular weight of from about 1,000 Daltons to about 100,000 Daltons. Preferably, the weight-average molecular weight is from about 10,000 Daltons to about 50,000 Daltons, more preferably, from about 30,000 Daltons to about 50,000 Daltons. Useful poly(vinyl alcohols) have a degree of hydrolysis of from about 50% to about 100% —OH groups. The balance of groups are acetates. Preferably the degree of hydrolysis is from about 60% to about 100%, more preferably from about 80% to about 100%, most preferably from about 95% to about 99%.

In another embodiment, at least one poly(vinyl alcohol) copolymer is used as the poly(hydroxylic) compound that is derivatized with acetoacetate groups. Suitable comonomers for the poly(vinyl alcohol) copolymers include, but are not limited to, ethylene, methyl acrylate, methyl methacrylate, acrylic acid, itaconic acid, maleic acid, fumaric acid, methyl vinyl ether, propylene, 1-butene, and mixtures thereof. Preferably, the copolymer comprises between about 1 mole percent and about 25 mole percent of the comonomer relative to the vinyl alcohol units.

In another embodiment, at least one linear or branched polyether is used as the poly(hydroxylic) compound that is derivatized with acetoacetate groups. Useful linear or branched polyethers have a molecular weight of about 500 Daltons to about 20,000 Daltons. Suitable examples of linear or branched polyethers include, but are not limited to, linear or branched poly(ethylene oxide), linear or branched poly(propylene oxide), linear or branched copolymers of poly(ethylene oxide) and poly(propylene oxide), linear or branched poly(1,3-trimethylene oxide), linear or branched poly(1,4-tetramethylene oxide), star poly(ethylene oxide), comb poly(ethylene oxide), star poly(propylene oxide), comb poly(propylene oxide), and mixtures thereof. Many linear polyethers are available commercially from companies such as Sigma-Aldrich. Many branched polyethers are available from Nektar Transforming Therapeutics (Huntsville, Ala.).

In another embodiment, at least one polysaccharide is used as the poly(hydroxylic) compound that is derivatized with acetoacetate groups. The term "polysaccharide", as used herein, refers to a molecule comprising two or more monosaccharide units. Suitable polysaccharides include, but are not limited to, dextran, agar, alginic acid, hyaluronic acid, sucrose, maltose, lactose, raffinose, and mixtures thereof. The preferred weight-average molecular weight for the polysaccharide is from about 300 Daltons to about 200,000 Daltons, more preferably from about 500 Daltons to about 200,000 Daltons, most preferably from about 10,000 Daltons to about 100,000 Daltons.

In another embodiment, at least one monosaccharide is used as the poly(hydroxylic) compound that is derivatized with acetoacetate groups. Suitable monosaccharides include, but are not limited to, ribose, glucose, mannose, galactose, fructose, sorbose, and mixtures thereof.

In another embodiment, at least one reduced monosaccharide is used as the poly(hydroxylic) compound that is derivatized with acetoacetate groups. Suitable reduced monosaccharides include, but are not limited to, sorbitol, mannitol, iditol, dulcitol, and mixtures thereof.

In another embodiment, at least one low molecular weight polyol is used as the poly(hydroxylic) compound that is derivatized with acetoacetate groups. The polyol has at least two hydroxy groups and has a molecular weight of less than about 300 Daltons. Examples of useful low molecular weight polyols include, but are not limited to, glycerol, trimethylolpropane, pentaerythritol, dipentaerythritol and mixtures thereof.

In another embodiment, at least one hydrolyzed polyvinyl acetate-methyl acrylate copolymer is used as the poly(hydroxylic) compound that is derivatized with acetoacetate groups. Preferably, the methyl acrylate content of the hydrolyzed polyvinyl acetate-methyl acrylate copolymer is from about 1% to about 20% by weight of the copolymer and the polyvinyl acetate is 100% hydrolyzed. The hydrolyzed polyvinyl acetate-methyl acrylate copolymer of the invention has a molecular weight of about 20,000 Daltons to about 80,000 Daltons. An example of a useful poly(vinyl alcohol)-methyl acrylate copolymer is sold under the tradename Elvanol® 80-18 by E.I. du Pont de Nemours and Company (Wilmington, Del.).

In another embodiment, at least one polyether condensation product is used as the poly(hydroxylic) compound that is derivatized with acetoacetate groups. The condensation product is produced by reacting at least one core molecule having more than one carboxylic acid group with a sufficient amount of at least one polyether terminated with hydroxy groups to produce an esterified polyether with an average of at least two hydroxy end groups. Suitable core molecules include, but are not limited to oxalic acid, malonic acid, succinic acid, glutaric acid, adipic acid, benzenedicarboxylic acid, benzenetricarboxylic acid, benzenetetracarboxylic acid, cyclohexanetricarboxylic acid, cyclopentanetetracarboxylic acid, adamantanetetracarboxylic acid, biphenyltetracarboxylic acid, benzophenonetetracarboxylic acid, propanetricarboxylic acid, butanetetracarboxylic acid, and mixtures thereof. Suitable polyethers for use in the polyether condensation product include, but are not limited to linear poly(ethylene oxide), linear poly(propylene oxide), linear copolymers of poly(ethylene oxide) and poly(propylene oxide), linear poly(1,3-trimethylene oxide), and linear poly(1,4-tetramethylene oxide). The preparation of a polyether condensation product formed by reacting polyethylene glycol with tetramethyl cyclopentane-1,2,3,4-tetracarboxylate is described in Example 10. This is a general method that may be used to prepare other polyether condensation products.

Any of the aforementioned poly(hydroxylic) compounds may be derivatized with acetoacetate groups by reaction with diketene. As an example, the derivatization reaction for poly(vinyl alcohol) (PVOH) is as follows:

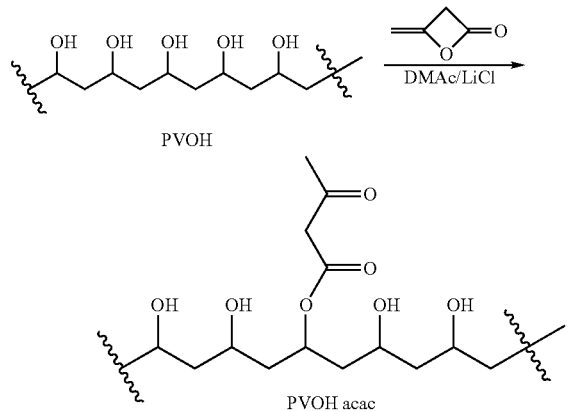

Alternative methods of synthesis, such as ester exchange with t-butyl acetoacetate, are also available. Such alternative methods are within the scope of the present invention.

Preferably, the acetoacetate derivatives of the invention have an equivalent weight per acetoacetate group of about 100 Daltons to about 2,000 Daltons.

Polyamino Compounds Derivatized with Acetoacetamide Groups

A wide variety of polyamino compounds derivatized with acetoacetamide groups may be used either in place of or in combination with the poly(hydroxylic) compounds derivatized with acetoacetamide groups, described above, to react with an amino-functional crosslinking compound to form the tissue adhesive of the invention. The polyamino compounds of the invention have a weight-average molecular weight of less than about 200,000 Daltons, preferably, from about 500 Daltons to about 200,000 Daltons. Suitable polyamino compounds include, but are not limited to, amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), and mixtures thereof. These polyamino compounds are either available commercially or may be prepared using methods known in the art. For example, amino-terminated branched poly(ethylene oxides) and poly(propylene oxides), are available from Nektar Transforming Therapeutics and Huntsman LLC (Houston, Tex.). One example is amino-terminated poly(ethylene oxide)-poly(propylene oxide) sold by Huntsman as XTJ-502. Additionally, amino-terminated linear or branched polyamino compounds may be prepared by replacing the hydroxyl groups on poly(hydroxylic) compounds with amino groups according to the method described by Buckmann et al. (*Makromol. Chem.* 182:1379-1384, 1981). According to that method, the poly(hydroxy) compound is reacted with thionyl bromide to convert the hydroxyl groups to bromines, which are then converted to amines by reaction with ammonia at 100° C. The method is broadly applicable to the preparation of many useful polyamino compounds. Other methods that may used for preparing polyamino compounds are described by Merrill et al. in U.S. Pat. No. 5,830,986, and by Chang et al. in WO 97/30103. Additionally, a branched polyamino compound may be prepared by polymerizing or copolymerizing a vinylamine precursor monomer and converting the polymer or copolymer to a vinylamine-containing polymer or copolymer according to well-known methods. One example is the copolymerization of vinyl acetate and N-vinylformamide, followed by basic hydrolysis of the acetate and formamide groups to yield a vinyl alcohol-vinylamine copolymer (Robeson et al., U.S. Pat. No. 5,397,436).

The polyamino compounds may be derivatized with acetoacetamide groups by reaction with diketene, as described above for the derivatization of the poly(hydroxylic) compounds. The detailed procedure for the derivatization of Hunstman XTJ-502 is given in Example 9. Preferably, the polyamino acetoacetamide derivatives of the invention have an equivalent weight per acetoacetamide group of about 100 Daltons to about 2,000 Daltons.

In the invention, the poly(hydroxylic) compound derivatized with acetoacetate groups and/or the polyamino compound derivatized with acetoacetamide groups are used in the form of an aqueous solution, herein referred to as "the acetoacetate/acetoacetamide solution". The aqueous solution comprises at least one poly(hydroxylic) compound derivatized with acetoacetate groups or at least one polyamino compound derivatized with acetoacetamide groups at a concentration of at least about 5% by weight, preferably about 5% to about 50% by weight, more preferably from about 15% to about 30% by weight. The solution may comprise mixtures of any of the poly(hydroxylic) compounds derivatized with acetoacetate groups and the polyamino compounds derivatized with acetoacetamide groups described above in order to modify the rate of gelation, the mechanical properties of the resulting hydrogel, biocompatibility, biodegradation rate and the like. If a mixture of different acetoacetate compounds and/or acetoacetamide compounds is used, the total concentration of the components is from about 5% to about 50% by weight, preferably from about 15% to about 30% by weight (i.e., the water content of the aqueous solution is preferably from about 70% to about 85% by weight relative to the weight of the aqueous solution). The optimal concentration to be used depends on the application and on the concentration of the amino-functional crosslinking compound used, as described below, and can be readily determined by one skilled in the art using routine experimentation.

For use on living tissue, it is preferred that the acetoacetate/acetoacetamide solution be sterilized to prevent infection. When the substitution level of the acetoacetate/acetoacetamide groups on the polymer is less than or equal to 5 mole percent, the solution may be sterilized with gamma irradiation under a flux of 25 kilograys (kGy). Solutions of polymers having any substitution level of acetoacetate/acetoacetamide may be sterilized by autoclaving at about 121° C. or by ultrafiltration through a 0.2 µm pore membrane.

The acetoacetate/acetoacetamide solution of the invention may also include an oxidized polysaccharide component at a concentration of about 2% to about 20% by weight, preferably from about 2% to about 10% by weight relative to the total weight of the solution. The aldehyde groups of the oxidized polysaccharide are thought to covalently bind to the amine groups on the tissue and to the amino-functional crosslinking compound, thereby increasing the adhesive strength of the tissue adhesive. Polysaccharides useful in the invention include, but are not limited to, dextran, chitin, starch, agar, cellulose, and hyaluronic acid. These polysaccharides are available commercially from sources such as Sigma-Aldrich. In one embodiment, the polysaccharide is dextran. Suitable polysaccharides have a molecular weight from about 1,000 to about 1,000,000 Daltons, and in addition from about 3,000 to about 250,000 Daltons. The polysaccharide is oxidized to introduce aldehyde groups using any suitable oxidizing agent, including but not limited to, periodates, hypochlorites, ozone, peroxides, hydroperoxides, persulfates, and percarbonates. In one embodiment, the polysaccharide is oxidized by reaction with sodium periodate, for example as described by Goldmann et al. (WO 03/35122). The polysaccharide may be reacted with different amounts of periodate to give polysaccharides with different degrees of oxidation and therefore, different amounts of aldehyde groups. The aldehyde content of the oxidized polysaccharide may be determined using methods known in the art. For example, the dialdehyde content of the oxidized polysaccharide may be determined using the method described by Hofreiter et al. (*Anal Chem.* 27:1930-1931, 1955). In that method, the amount of alkali consumed per mole of dialdehyde in the oxidized polysaccharide, under specific reaction conditions, is determined by a pH titration. The equivalent weight per aldehyde group of the oxidized polysaccharide is from about 90 to about 1500 Daltons.

The acetoacetate/acetoacetamide solution of the invention may further comprise various additives depending on the intended application. The additive should be compatible with the acetoacetate and/or acetoacetamide components. Specifically, the additive does not contain primary amine groups that would react with the acetoacetate or acetoacetamide components. For example, the solution may optionally include at least one pH modifier to adjust the pH of the solution. Suitable pH modifiers are well known in the art. The pH modifier may be an acidic or basic compound. Examples of acidic pH modifiers include, but are not limited to carboxylic acids, inorganic acids, and sulfonic acids. Examples of basic pH modifiers include, but are not limited to hydroxides, alkoxides, nitrogen-containing compounds other than primary amines and basic carbonates and phosphates.

The acetoacetate/acetoacetamide solution may optionally include at least one viscosity modifier. The viscosity modifier may be selected from among known viscosity modifiers, including, but not limited to polysaccharides and derivatives thereof, such as starch or hydroxyethylcellulose.

The acetoacetate/acetoacetamide solution may optionally include at least one antimicrobial agent. Suitable antimicrobial preservatives are well known in the art. Examples of suitable antimicrobials include, but are not limited to alkyl parabens, such as methylparaben, ethylparaben, propylparaben, and butylparaben; triclosan; chlorhexidine; cresol; chlorocresol; hydroquinone; sodium benzoate; and potassium benzoate. In one embodiment, the antimocrobial is triclosan.

Additionally, the acetoacetate/acetoacetamide solution may optionally include at least one colorant to enhance the visibility of the solution. Suitable colorants include dyes, pigments, and natural coloring agents. Examples of suitable colorants include, but are not limited to, FD&C and D&C colorants, such as FD&C Violet No. 2, FD&C Yellow No. 6, FD&C Red No. 3, D&C Green No. 6, D&C Green No. 5, D&C Violet No. 2; and natural colorants, such as beetroot red, canthaxanthin, chlorophyll, eosin, saffron, and carmine. In one embodiment, the colorant is FD&C Violet No. 2, D&C Green No. 6, D&C Green No. 5, or D&C Violet No. 2.

The acetoacetate/acetoacetamide solution may also optionally include at least one surfactant. Surfactant, as used herein, refers to a compound that lowers the surface tension of water. The surfactant may be an ionic surfactant, such as sodium lauryl sulfate; or a neutral surfactant, such as polyoxyethylene ethers, polyoxyethylene esters, and polyoxyethylene sorbitan.

Additionally, the acetoacetate/acetoacetamide solution may optionally include anti-inflammatory agents, such as indomethacin, salicylic acid acetate, ibuprophen, sulindac, piroxicam, and naproxen; thrombogenic agents, such as thrombin, fibrinogen, homocysteine, and estramustine; and radio-opaque compounds, such as barium sulfate and gold particles.

Amino-Functional Crosslinking Agent

The poly(hydroxylic) compound derivatized with acetoacetate groups and/or the polyamino compound derivatized with acetoacetamide groups are reacted with an amino-functional crosslinking agent to form the hydrogel network that can be used as a tissue adhesive in medical applications. The amino-functional crosslinking compound comprises two or more primary amine groups, or at least one primary amine group and at least one other functional group capable of reacting with acetoacetate or acetoacetamide groups or with itself. The amino-functional crosslinking agent may be a polyamino compound having an equivalent weight per amino group of about 100 Daltons to about 1,000 Daltons. Suitable polyamino compounds include linear or branched polyamines such as polyethyleneimine. The weight-average molecular weight of linear polyethyleneimine is in the range of from about 100 Daltons to about 5,000 Daltons. A weight-average molecular weight in the range of from about 200 Daltons to about 2,000 Daltons is preferred. For branched polyethyleneimine the weight-average molecular weight is from about 300 Daltons to about 100,000 Daltons. A preferred range of the weight-average molecular weight for branched polyethyleneimine is from about 500 Daltons to about 2,000 Daltons. A further preferred range of the weight-average molecular weight for branched polyethyleneimine is from about 600 Daltons to about 800 Daltons. Suitable polyethyleneimines are available from companies such as Sigma-Aldrich.

Other polyamino compounds include, but are not limited to, 4,9-dioxa-1,12 dodecanediamine, amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), and dendrimeric amino-terminated copoly(ethylenediaminetetrapropionic acid-ethylenediamine) poly(amidoamines) ("Starburst®" dendrimers; e.g., Sigma-Aldrich #412449). Examples of star polyethylene oxide amines, include, but are not limited to star polyethylene glycols having 3, 4, and 8 arms terminated with primary amines (referred to herein as 3, 4 and 8 arm star PEG amines, respectively), and various multi-arm polyethylene glycol amines, available from Nektar Transforming Therapeutics. The 8-arm star PEG amine is available from Nektar Transforming Therapeutics. Examples of suitable amino-terminated branched poly(propylene oxides) include, but are not limited to Jeffamine® T-403 (CAS No. 39423-51-3), Jeffamine® T-3000 (CAS No. 64852-22-8), and Jeffamine® T-5000 (CAS No. 64852-22-8). These polyamino compounds are either available commercially or may be prepared using methods known in the art, as described above.

Also included in the polyamino compounds are the comb polyamines such as poly(vinyl alcohol) derivatized with 4-aminobutyral acetal, poly(vinyl alcohol-vinylamine) copolymer, polylysine and polyallylamine. The weight-average molecular weight of polyvinyl alcohol 4-aminobutyral acetal is in the range of from about 5,000 Daltons to about 100,000 Daltons. A weight-average molecular weight in the range of from about 10,000 Daltons to about 50,000 Daltons is preferred. A weight-average molecular weight in the range of from about 30,000 Daltons to about 50,000 Daltons is further preferred. The polyvinyl alcohol in the polyvinyl alcohol 4-aminobutyral acetal is hydrolyzed in the range of from about 50% of —OH to 100% of —OH groups. The balance groups are acetate. A preferred range is from about 80% to 100%. A further preferred range is from about 95% to about 99%. The polyvinyl alcohol chain is randomly substituted with the 4-aminobutyral acetal groups in the range of from about 1 mole percent to about 25 mole percent. A preferred range of mole percent of the 4-aminobutyral acetal group substitution on the polyvinyl alcohol chain is from about 5% to about 15%. A further preferred range of mole percent of the 4-aminobutyral acetal group substitution on the polyvinyl alcohol chain is from about 8% to about 12%. The proportion of free —NH$_2$ as compared to NH$_3$ salts is in the range of from about 10% to 100%. A preferred range of —NH$_2$ groups is in the range of from about 80% to 100%. A further preferred proportion of free —NH$_2$, is about 100%. The poly(vinyl alcohol) derivatized with 4-aminobutyral acetal may be prepared according to the method of Robeson et al. (U.S. Pat. No. 5,397,436) as described in Example 11.

Poly(vinyl alcohol-vinylamine) copolymer can be prepared by the basic or acidic hydrolysis of poly(vinyl acetate-N-vinylformamide) copolymer. Poly(vinyl acetate-co-N-vinylformamide) can be made by the free-radical copolymerization of vinyl acetate and N-vinylformamide according to Robeson et al., U.S. Pat. No. 5,397,436, as described in Example 12. The weight-average molecular weight of poly(vinyl alcohol-co-vinylamine) is in the range of from about 10,000 Daltons to about 100,000 Daltons. A weight-average molecular weight in the range of from about 30,000 Daltons to about 80,000 Daltons is preferred. A weight average molecular weight of about 50,000 Daltons is further preferred. The polyvinyl alcohol chain is substituted with amino groups in the range of from about 1 mole percent to about 25 mole percent. A preferred range of mole percent of amino group substitution on the polyvinyl alcohol chain is from about 5% to about 20%. A further preferred range of mole percent of the amino group substitution on the polyvinyl alcohol chain is from about 8% to about 15%. The proportion of free —NH$_2$ as compared to NH$_3$ salts is in the range of from about 10% to 100%. A preferred range of —NH$_2$ groups is in the range of from about 80% to 100%.

The weight-average molecular weight of polylysine is in the range of from about 10,000 Daltons to about 100,000 Daltons. A weight-average molecular weight in the range of from about 30,000 Daltons to about 80,000 Daltons is preferred. A weight-average molecular weight of about 60,000 Daltons is further preferred. The proportion of free —NH$_2$ as compared to NH$_3$ salts is in the range of from about 10% to 100%. A preferred range of —NH$_2$ groups is in the range of from about 20% to 80%. A further preferred proportion of free —NH$_2$, is in the range of from about 50% to 60%.

The weight-average molecular weight of polyallylamine is in the range of from about 10,000 Daltons to about 70,000 Daltons. A weight-average molecular weight in the range of from about 10,000 Daltons to about 20,000 Daltons is preferred. A weight-average molecular weight of about 15,000 Daltons is further preferred. The proportion of free —NH$_2$ as compared to NH$_3$ salts is in the range of from about 10% to 100%. A preferred range of —NH$_2$ groups is in the range of from about 20% to 80%. A further preferred proportion of free —NH$_2$, is in the range of from about 40% to 60%.

Also included in the polyamino compounds are linear or branched diaminoalkanes. The diaminoalkane comprises examples such as α,ω-substituted diaminoalkane, β,ω-substituted diaminoalkane, β,(ω-1)-substituted diaminoalkane and the like. The weight-average molecular weight of diaminoalkane is in the range of from about 80 Daltons to about 300 Daltons.

Also included in the polyamino compounds are cyclic diamines such as isophorone diamine(5-amino-1,3,3-trimethylcyclohexanemethylamine), N,N'-bis(3-aminopropyl)piperazine, 1,3-bis(aminomethyl)cyclohexane, 1,4-diaminocyclohexane, and p-xylylenediamine.

Also included in the amino-functional crosslinking agents are polyhydrazides such as adipic dihydrazide, and bis(carboxyhydrazido)polyethers, including not limited to, (hydrazidocarboxymethyl)-terminated linear or branched poly(ethylene oxide), such as poly(carboxyhydrazido) star polyethers; (hydrazidocarboxymethyl)-terminated linear or branched poly(propylene oxide), (hydrazidocarboxymethyl)-terminated linear or branched poly(ethylene oxide)-poly(propylene oxide) copolymer, (hydrazidocarboxymethyl)-terminated linear or branched poly(1,3-trimethylene oxide), (hydrazidocarboxymethyl)-terminated linear or branched poly(1,4-tetramethylene oxide). The hydrazidocarboxymethyl-terminated compounds may be prepared using the method of Zalipsky (ACS Symposium Series 680, American Chemical Society, Washington, D.C., 1997, pp. 318-341).

Additional polyamino compounds include, but are not limited to, spermine, and spermidine.

Also included in the amino-functional crosslinking agents are 3-aminopropyltrialkoxysilanes, 3-aminopropyldialkoxyalkylsilanes and 3-aminopropylmonoalkoxydialkylsilanes, including, but not limited to, 3-aminopropyltrimethoxysilane, 3-aminopropyltriethoxysilane, 3-aminopropyltripropoxysilane, N-(2-aminoethyl)-3-aminopropyltrimethoxysilane, 3-aminopropyldimethoxymethylsilane, 3-aminopropyldiethoxymethylsilane, 3-aminopropyldipropoxymethylsilane, 3-aminopropyldimethoxyethylsilane, 3-aminopropyldiethoxyethylsilane, 3-(methoxydimethylsilyl)propylamine, 3-(ethoxydimethylsilyl)propylamine and mixtures thereof. The mechanism of reaction of these silanes with poly(hydroxylic) compounds derivatized with acetoacetate groups or polyamino compounds derivatized with acetoacetamide groups involves initial attack of the amino group on the acetoacetate or acetoacetamide group; once the stabilization due to the free amino group is gone, the silane group quickly hydrolyzes to form siloxane crosslinks.

Moreover, mixtures of any of the aforementioned amino-functional crosslinking agents may be used In the invention, the amino-functional crosslinking agent is generally used in the form of an aqueous solution. The 3-aminopropyltrialkoxysilanes, 3-aminopropyldialkoxyalkylsilanes or 3-aminopropylmonoalkoxydialkylsilanes may be used in the form of a neat liquid or in an aqueous solution. The aqueous solution comprises at least one amino-functional crosslinking agent at a concentration of about 5% to about 50% by weight, preferably 15% to about 30% by weight relative to the total weight of the solution. The optimal concentration depends on the application and on the concentration of the acetoacetate/acetoacetamide solution used. Preferably, the mole ratio of acetoacetate and/or acetoacetamide groups to amine groups is from about 2:1 to about 1:2. The solution may comprise mixtures of any of the amino-functional crosslinking agents described above in order to modify the rate of gelation, the mechanical properties of the resulting hydrogel, biocompatibility, biodegradation rate and the like. If a mixture of different amino-functional crosslinking agents is used, the total concentration of the components is from about 5% to about 50% by weight, preferably from about 15% to about 30% by weight (i.e., the water content of the aqueous solution is preferably from about 70% to about 85% by weight relative to the weight of the aqueous solution). For example, at least one of the polyamino compounds suitable for use as an amino-functional crosslinking agent may be combined with at least one 3-aminopropyltrialkoxysilane, 3-aminopropyldialkoxyalkylsilane or 3-aminopropylmonoalkoxydialkylsilane in the aqueous solution.

For use on living tissue, it is preferred that the amino-functional crosslinking agent solution be sterilized to prevent infection. The aqueous solution comprising the amino-functional crosslinking agent and the neat 3-aminopropyltrialkoxysilanes, 3-aminopropyldialkoxyalkylsilanes or 3-aminopropylmonoalkoxydialkylsilanes may be sterilized by gamma irradiation under a flux of 25 kGy, autoclaving at about 121° C., or by ultrafiltration through a 0.2 μm pore membrane.

The aqueous solution comprising the amino-functional crosslinking agent may further comprise various additives. Any of the additives described above for the acetoacetate/acetoacetamide solution, with the exception of the oxidized dextran, may be used. Additionally, the amino-functional crosslinking agent solution may comprise a healing promoter, such as chitosan.

In one embodiment, the invention provides a kit comprising an aqueous solution comprising at least one poly(hydroxylic) compound derivatized with acetoacetate groups and/or at least one polyamino compound derivatized with acetoacetamide groups, and a second component comprising an aqueous solution of at least one polyamino compound, or at least one 3-aminopropyltrialkoxysilane, 3-aminopropyldialkoxyalkylsilane or 3-aminopropylmonoalkoxydialkylsilane, neat or in aqueous solution, or an aqueous solution comprising a polyamino compound and at least one 3-aminopropyltrialkoxysilane, 3-aminopropyldialkoxyalkylsilane or 3-aminopropylmonoalkoxydialkylsilane. Each of the solutions may be contained in any suitable vessel, such as a vial or a syringe barrel.

In another embodiment, the invention provides a kit comprising an aqueous solution comprising at least one poly(hydroxylic) compound derivatized with acetoacetate groups and/or at least one polyamino compound derivatized with acetoacetamide groups, a second component comprising an aqueous solution of at least one polyamino compound, and at least one 3-aminopropyltrialkoxysilane, 3-aminopropyldialkoxyalkylsilane or 3-aminopropylmonoalkoxydialkylsilane, neat or in aqueous solution. Each of the solutions may be contained in any suitable vessel, such as a vial or a syringe barrel.

In both of the aforementioned embodiments, the aqueous solution comprising at least one poly(hydroxylic) compound derivatized with acetoacetate groups and/or at least one polyamino compound derivatized with acetoacetamide groups further comprises an oxidized polysaccharide, as described above.

Additionally, the kit may further comprise an aqueous solution comprising an oxidized polysaccharide, contained in any suitable vessel as described above. The oxidized polysaccharide solution may be used to prime the site of application of the adhesive, as described below. The solution comprises an oxidized polysaccharide, as described above, at a concentration of about 2% to about 40% by weight. For use on living tissue, it is preferred that the aqueous solution comprising the oxidized polysaccharide be sterilized to prevent infection. The solution may be sterilized by any method known in the art that does not degrade the polysaccharide, including electron beam irradiation, gamma irradiation, or ultra-filtration through a 0.2 μm pore membrane. Additionally, the oxidized polysaccharide solution may further comprise any of the additives described above.

Method of Application

The acetoacetate/acetoacetamide solution and the aqueous solution comprising the amino-functional crosslinking agent and/or a neat 3-aminopropyltrialkoxysilane, 3-aminopropyldialkoxyalkylsilane or 3-aminopropylmonoalkoxydialkylsilane may be applied to an anatomical site on tissue of a living organism in any number of ways. Once the two solutions are applied to a site, they crosslink to form a hydrogel, a process referred to herein as curing, typically in about 5 seconds to about 5 minutes. Additionally, more than these two distinct solutions may be applied to the site. For example, two different acetoacetate/acetoacetamide solutions comprising different acetoacetate and/or acetoacetamide components may be used in conjunction with an aqueous solution comprising the amino-functional crosslinking agent or a neat 3-aminopropyltrialkoxysilane, 3-aminopropyldialkoxyalkylsilane or 3-aminopropylmonoalkoxydialkylsilane. As another example, the acetoacetate/acetoacetamide solution may be used in conjunction with an aqueous solution comprising the amino-functional crosslinking agent, and a third solution comprising at least one 3-aminopropyltrialkoxysilane, 3-aminopropyldialkoxyalkylsilane or 3-aminopropylmonoalkoxydialkylsilane, as a neat liquid or in an aqueous solution.

In one embodiment, the two solutions are applied to the site sequentially using any suitable means including, but not limited to spraying, brushing with a cotton swab or brush, or extrusion using a pipette, or a syringe. The solutions may be applied in any order, preferably the acetoacetate/acetoacetamide solution is added first. Then, the solutions are mixed on the site using any suitable device, such as a cotton swab or the tip of the pipette or syringe. The method of application and mixing will be dictated by the intended use of the adhesive. For example, spraying may be used to apply the components to function as an antiadhesive to a relatively large surface area, while a syringe may be more appropriate for applying the components to a site for sealing an incision, such as a corneal incision.

In another embodiment, the two solutions are mixed manually before application to the site. The resulting mixture is then applied to the site before it completely cures using a suitable applicator, as described above.

In another embodiment, the two solutions are contained in a double-barrel syringe. In this way the two solutions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47) which is incorporated herein by reference. Additionally, the double barrel syringe may contain a motionless mixer, such as that available from ConProtec, Inc. (Salem, N.H.), at the tip to effect mixing of the two solutions prior to application. For the application of more than two solutions, the double-barrel syringe may be modified to have the required number of barrels, such that each of the solutions is contained in a separate barrel.

In another embodiment, the acetoacetate/acetoacetamide solution and the aqueous solution comprising the amino-functional crosslinking agent are applied to the site in any order, or are premixed and then applied to the site, and a third component comprising at least one 3-aminopropyltrialkoxysilane, 3-aminopropyldialkoxyalkylsilane or 3-aminopropylmonoalkoxydialkylsilane, neat or in aqueous solution, is applied to the site as at substantially the same time as the amino-functional crosslinking agent or as the premixed solution, using any of the methods described above.

In another embodiment, the site is first primed by application of an aqueous solution comprising an oxidized polysaccharide using any of the methods described above. Then, the acetoacetate/acetoacetamide solution and the aqueous solution comprising the amino-functional crosslinking agent and/or at least one 3-aminopropyltrialkoxysilane, 3-aminopropyldialkoxyalkylsilane or 3-aminopropylmonoalkoxydialkylsilane, neat or in aqueous solution, are applied to the site, as described above.

In another embodiment, the tissue adhesive of the invention may be used to bond at least two anatomical sites together. In this embodiment, a mixture of the acetoacetate/acetoacetamide solution and the aqueous solution comprising the amino-functional crosslinking agent and/or at least one neat 3-aminopropyltrialkoxysilane, 3-aminopropyldialkoxyalkylsilane or 3-aminopropylmonoalkoxydialkylsilane, either premixed manually or using a double-barrel syringe applicator, are applied to at least one of the anatomical sites to be bonded using the methods described above. The two or more sites are contacted and held together manually or using some other means, such as a surgical clamp, for a time sufficient for the mixture to cure, typically about 2 to 5 minutes. Alternatively, the two solutions are applied to at least one site sequentially using any suitable means, as described above. The solutions may be applied in any order, preferably the acetoacetate/acetoacetamide solution is added first. Then, the solutions are mixed on the site using any suitable device, such as a cotton swab or the tip of the pipette or syringe, and the two or more sites are contacted and held together, as described above. Additionally, the acetoacetate/acetoacetamide solution and the aqueous solution comprising the amino-functional crosslinking agent may be applied to at least one site in any order, or are premixed and then applied to the site, and a third component comprising at least one 3-aminopropyltrialkoxysilane, 3-aminopropyldialkoxyalkylsilane or 3-aminopropylmonoalkoxydialkylsilane, neat or in aqueous solution, is applied to the site at substantially the same time as the amino-functional crosslinking agent or as the premixed solution, using any of the methods described above. Then, the two or more sites are contacted and held together, as described above. As noted above, more than these two distinct solutions may be applied to at least one of the sites to be bonded. Optionally, at least one of the sites to be bonded is primed with an aqueous solution comprising an oxidized polysaccharide, as described above. Preferably, all sites to be bonded are primed. Then, the acetoacetate/acetoacetamide solution and the aqueous solution comprising the amino-functional crosslinking agent and/or at least one 3-aminopropyltrialkoxysilane, 3-aminopropyldialkoxyalkylsilane or 3-aminopropylmonoalkoxydialkylsilane, neat or in aqueous solution, are applied to the site, as described above. The two or more sites are contacted and held together, as described above.

Medical and Veterinary Applications

The tissue adhesive of the invention has many potential medical and veterinary applications, including, but not limited to topical wound closure, surgical procedures, such as intestinal anastomosis, vascular anastomosis, and ophthalmic procedures; drug delivery, and anti-adhesive applications. For these uses, procedures involving the application of two aqueous solutions, one comprising the acetoacetate and/or acetoacetamide derivative, the other comprising the amine-functional crosslinking compound are described below. The application of three or more solutions may also be used for these purposes using the procedures describe above. Additionally, the site may first be primed with an aqueous solution comprising oxidized dextran, as described above.

The tissue adhesive of the invention may be used for treatment of topical wounds, including but not limited to minor cuts, scrapes, irritations, abrasions, lacerations, burns, sores, and surgical wounds. For topical wound closure, the acetoacetate/acetoacetamide solution and the aqueous solution comprising the amino-functional crosslinking agent are applied to the wound using the methods described above, and the mixture is allowed to cure.

The tissue adhesive of the invention may also be used in surgical procedures, including but not limited to intestinal anastomosis, venous anastomosis, and ophthalmic procedures, such as sealing corneal cataract incisions.

Intestinal anastomosis is a surgical procedure that is well known to skilled surgeons. The procedure, which involves joining two segments of the intestine together after a resection, is described by Sweeney et al. (*Surgery* 131:185-189, 2002). The two segments of the intestine are joined together using sutures or staples. A problem encountered with this procedure is leakage around the sutures or staples. Leakage rates of 5-8% have been reported (Bruce et al. *Br. J. Surg.* 88:1157-1168, 2001). The tissue adhesive of the invention may be used to supplement the sutures or staples used in intestinal anastomoses, providing a better seal that reduces leakage. In this application, the acetoacetate/acetoacetamide solution and the aqueous solution comprising the amino-functional crosslinking agent are applied to the intestine around the sutures or staples, using the methods described above, and the mixture is allowed to cure.

Additionally, the tissue adhesive of the invention may be used in venous anastomosis procedures. This procedure is similar to intestinal anastomosis, described above, and is used for venous grafts. The two segments of blood vessel are joined together using sutures or staples. The tissue adhesive of the invention may be used to supplement the sutures or staples, providing a better seal that reduces leakage. In this application, the acetoacetate/acetoacetamide solution and the aqueous solution comprising the amino-functional crosslinking agent are applied to the blood vessel around the sutures or staples, using the methods described above, and the mixture is allowed to cure.

Temporal clear corneal incisions and scleral tunnel incisions are used during cataract surgery. These procedures are well known to the skilled cataract surgeon. Although these incisions can be sealed with sutures, many surgeons prefer sutureless, self-sealing incisions. However, problems arise with leakage through the sutureless incisions, causing endophthalmitis (Sarayba et al. Amer. *J. Opthamol.* 138:206-210, 2004, and Kim et al. *J. Cataract Refract. Surg.* 21:320-325, 1995). The tissue adhesive of the invention may be used to seal both clear corneal incisions and scleral tunnel incisions to prevent leakage. In this application, the acetoacetate/acetoacetamide solution and the aqueous solution comprising the amino-functional crosslinking agent are applied to the site of the incision in the eye, using the methods described above, and the mixture is allowed to cure.

The tissue adhesive of the invention may also be used to prevent adhesions between adjacent anatomical sites following surgery or injury to internal organs. The acetoacetate/acetoacetamide solution and the aqueous solution comprising the amino-functional crosslinking agent are applied to one anatomical site using the methods described above. The first site is prevented from contacting any adjacent site manually or using some other means, such as a surgical clamp, until the mixture cures, typically about 2 to 5 minutes. After curing, the hydrogel is no longer adhesive, and serves as a barrier preventing post-surgical adhesions.

The tissue adhesive of the invention may also be used for drug delivery to a selected anatomical site. In this application, at least one of the aqueous solutions further comprises a pharmaceutical drug or therapeutic agent. Suitable pharmaceutical drugs and therapeutic agents are well known in the art. An extensive list is given by Kabonov et al. in U.S. Pat. No. 6,696,089, which is incorporated herein by reference (in particular, columns 16 to 18). Examples include, but are not limited to antibacterial agents, antimicrobial agents, antiviral agents, antifungal agents, anti-cancer agents, vaccines, radiolabels, anti-inflammatories, anti-glaucomic agents, local anesthetics, anti-neoplastic agents, antibodies, hormones, and the like. In this application, the acetoacetate/acetoacetamide solution and the aqueous solution comprising the amino-functional crosslinking agent are applied to the desired anatomical site using the methods described above. After the hydrogel cures, the drug or therapeutic agent is released to the desired anatomical site. The rate of release depends on the degree of water swelling of the hydrogel, which can be controlled by the extent of crosslinking, which in turn is determined by the concentrations of the acetoacetate/acetoacetoamide solution and the aqueous solution comprising the amino-functional crosslinking agent used, as well as their respective degrees of functional group substitution. The concentration of reagents needed to obtain the proper rate of drug release for any particular application can be readily determined by one skilled in the art using routine experimentation.

Additionally, the tissue adhesive of the invention may be useful for other medical applications. These applications include, but are not limited to an adhesive to hold an implant in place, an adhesive used on tissue to block air, moisture, fluid or microbial migration, and an adhesive to replace or supplement sutures or staples in other surgical procedures, such as cholecystectomy, ostomy port, appendectomy, bariatrics, retinal reattachment, Cesarean closure, abdominal hysterectomy, and the closure of trauma punctures, and ruptured membranes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "acac" means acetoacetate, "DMAc" means dimethyl acetamide, "DMAP" means dimethylaminopyridine, "Da" means Dalton(s), "kDa" means kiloDalton(s), "min" means minute(s), "hr" means hour(s), "sec" means second(s), "mL" means milliliter(s), "L" means liter(s), "µL" means microliter(s), "cm" means centimeter(s), "$cm^{-1}$" means reciprocal centimeter(s), "eq wt" means equivalent weight, "$^1$H NMR" means proton NMR spectroscopy, "IR" means infrared spectroscopy, "mm" means millimeter(s), "µm" means micrometer(s), "mol" means mole(s), "mmol" means millimole(s), "g" means gram(s), "mg" means milligram(s), "mw" means molecular weight, "Mw" means weight-average molecular weight, "Mn" means number-average molecular weight, "M" means molar concentration, "N" means normality, "psig" means pounds per square inch gauge, "v/v" means volume to volume ratio, "wt %" means percent by weight, "mol %" means mole percent, "w/v %" means weight/volume percent, "PAA" means polyallylamine, "PEI" means polyethyleneimine, "PEG" means polyethylene glycol (also known as polyethyleneoxide), "THF" means tetrahydrofuran, "PVOH" means polyvinylalcohol, "PEEO acac" means pentaerythritol ethoxylate acetoacetate, "RB" means round-bottom, "RT" means room temperature, "MWCO" means molecular weight cut off, "UV" means ultraviolet, "ppm" means parts per million, "Pa" means pascal(s), "kPa" means kilopascal(s), "aq" means aqueous, and a reference to "Aldrich" or a reference to "Sigma" means the said chemical or ingredient was obtained from Sigma-Aldrich, St. Louis, Mo.

Example 1

Preparation of Fully-Hydrolyzed Polyvinylalcohol Acetoacetate

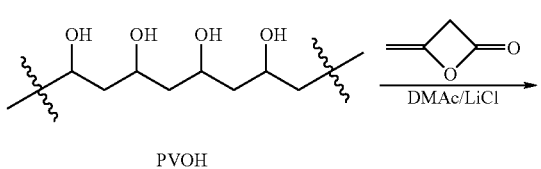

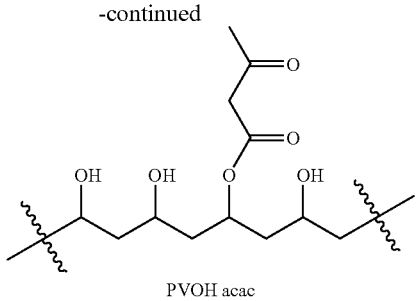

PVOH acac

1-A. Polyvinylalcohol (PVOH; Aldrich #36,313-8; 99% hydrolyzed; Mw=31,000-50,000 Da) was dried in the oven with a nitrogen sweep at 70° C. under 350 mm of Hg for 3 days. A weight loss of 3.7% was observed. A mixture of the dried polyvinylalcohol (25.0 g; 570 mmol OH), LiCl (3 g), N,N-4-dimethylaminopyridine (0.10 g) and dry DMAc (150 mL) was stirred in an oil bath maintained at 90° C., in a 500-mL RB flask under nitrogen for 1 hr to give a hazy, colorless solution. The solution was cooled to 70° C. and then stirred as 7.5 mL (8.2 g; 97 mmol) 85% diketene (Aldrich #42,236-3) was added.

The resulting orange solution was stirred at 70° C. for 2 hr. Then the polymer solution was added with stirring to a mixture of 250 mL methanol and 750 mL acetone in a Waring blender. The solvent was suction-filtered off the fibrous polymer suspension and the polymer was blended with 1 L fresh 1:3 methanol-acetone and the resulting suspension was filtered. The polymer was stirred overnight with 1 L acetone and then was suction-filtered, rinsed once with acetone and dried under suction under a nitrogen blanket to yield 25.1 g polyvinylalcohol acetoacetate. $^1$H NMR (D$_2$O): by ratio of the 2.35-ppm acetoacetate CH$_3$ peak to the 1.7-ppm backbone methylene hydrogen (H$_2$CCHOH) peak the polymer contained 11.8 mol % acetoacetate groups (eq wt=460).

1-B. Polyvinylalcohol (PVOH; 20.0 g; Aldrich #34,840-6; 99% hydrolyzed; Mw=13,000-23,000 Da; 450 mmol OH) was dissolved in 150 mL dry N,N-dimethylacetamide (DMAc) containing 6 g LiCl along with 100 mg of N,N-4-dimethylaminopyridine (DMAP) in a 200-mL RB flask under nitrogen with stirring and heating in a 90° C. oil bath to give a hazy, colorless solution.

The solution was divided into two approximately equal portions in two RB flasks. Portion one (1) was heated under nitrogen in a 60° C. oil bath and Portion 2 (2) in a 70° C. oil bath. The solutions were stirred as 2.0 mL (2.2 g; 26 mmol) 85% diketene was added to each. The resulting orange solutions were then stirred at 70° C. for 2 hr. The reaction solutions were each slowly poured into 500 mL methanol with rapid stirring, resulting in filterable fine suspensions of particulate polymer. The methanol was suction-filtered off and the polymers were stirred with 200-mL portions of fresh methanol and the resulting suspensions were filtered. The polymers were stirred overnight with 200 mL fresh methanol and then suction-filtered and air-dried under a nitrogen blanket. The yield was as follows:
polyvinylalcohol acetoacetate 1: 10.7 g
polyvinylalcohol acetoacetate 2: 10.0 g
$^1$H NMR (D$_2$O) 1: 4.1 mol % acac (eq wt=1160)
$^1$H NMR (D$_2$O) 2: 4.4 mol % acac (eq wt=1085).

1-C. Polyvinylalcohol (20.0 g; Mw=13,000-23,000 Da; 99% hydrolyzed; 450 mmol OH) was dissolved in 150 mL dry DMAc containing 5 g LiCl along with 100 mg of DMAP in a 500-mL RB flask under nitrogen with stirring and heating in a 90° C. oil bath for 1 hr to give a hazy, colorless solution. The solution was cooled to 70° C. and then stirred as 3.0 mL (3.3 g; 39 mmol) diketene was added; the resulting orange solution was stirred at 70° C. for 2 hr and then was precipitated into 1 L methanol. The methanol was suction-filtered off and the polymer was washed twice with fresh methanol and the resulting suspension was filtered and dried under suction with a nitrogen blanket overnight to yield 18.8 g polyvinylalcohol acetoacetate. $^1$H NMR (D$_2$O): 3.0 mol % acac (eq wt=1550).

1-D. Polyvinylalcohol (20.0 g; Mw=13,000-23,000 Da; 99% hydrolyzed; 450 mmol OH) was dissolved in 150 mL dry DMAc containing 5 g LiCl along with 100 mg of DMAP in a 500-mL RB flask under nitrogen with stirring and heating in a 90° C. oil bath for 1 hr to give a hazy, colorless solution. The solution was cooled to 70° C. and then stirred as 5.0 mL (5.5 g; 59 mmol) diketene was added. The resulting orange solution was stirred at 70° C. for 2 hr and then was precipitated into 1 L methanol. The methanol was suction-filtered off and the polymer was washed twice with fresh methanol and allowed to stir in methanol for 64 hr. The suspension was filtered and dried under suction with a nitrogen blanket followed by holding under vacuum (20 mm Hg) overnight with a nitrogen bleed through a syringe needle through a septum to yield 18.6 g polyvinylalcohol acetoacetate. $^1$H NMR (D$_2$O): 5.9 mol % acac (eq wt=830).

Example 2

Preparation of 88%-Hydrolyzed Polyvinylalcohol Acetoacetate

Partially-hydrolyzed polyvinylalcohol (20.00 g; Aldrich #36,317-0; Mw=13000-23000 Da; 87-89% hydrolyzed) was dried for 5 days at 50° C. under 300 mm Hg vacuum with a nitrogen bleed. Weight loss was 5.3% (1.05 g). The 19-g (380 mmol OH) sample was dissolved in 150 mL dry DMAc containing 5 g LiCl along with 100 mg of N,N-4-dimethylaminopyridine in a 500-mL RB flask under nitrogen. The mixture was stirred and heated in a 90° C. oil bath for 1 hr to give a hazy, colorless solution. The solution was cooled to 70° C. and then stirred as 2.9 mL (3.2 g; 38 mmol) diketene was added. The resulting orange solution was stirred at 70° C. for 3 hr and then was added to a mixture of 1 L methanol and 700 mL diethyl ether. The polymer suspension settled and the solvent was decanted off and replaced with 250 mL fresh ether. This was stirred and decanted and replaced with 500 mL fresh ether. The suspension was stirred, decanted and then suction-filtered. The solids were washed with 200 mL acetone and were suction-filtered and air-dried under a nitrogen blanket to yield 19.2 g 88%-hydrolyzed polyvinylalcohol acetoacetate.

$^1$H NMR (D$_2$O): 6.6 mol % acac (eq wt=830), from the ratio of the acetoacetate CH$_3$ (2.32 ppm) to the acetate CH$_3$ (2.1 ppm), where the acetate content was determined to be 11.7 mol % from the NMR spectrum of the parent PVOH.

Example 3

Preparation of 80%-Hydrolyzed Polyvinylalcohol Acetoacetate

Partially-hydrolyzed polyvinylalcohol (20.00 g; Aldrich #36,062-7; Mw=9000-10000 Da; 80% hydrolyzed) was dried for 5 days at 50° C. under 300 mm Hg vacuum with a nitrogen bleed. A weight loss was 3.4% (0.68 g) was observed. The 19.3-g (350 mmol OH) sample was dissolved in 150 mL dry DMAc containing 5 g LiCl along with 100 mg of N,N-4-dimethylaminopyridine in a 500-mL RB flask under nitrogen with stirring and heating in a 90° C. oil bath for 1 hr to give a hazy, colorless solution. The solution was cooled to 70° C. and then stirred as 2.7 mL (3.0 g; 35 mmol) diketene was added. The resulting orange solution was stirred at 70° C. for 3 hr and then was poured into 1200 mL acetone. The polymer suspension settled and the solvent was decanted off and the slurry was quickly suction-filtered. The damp cake was washed on the funnel with 500 mL acetone and was then stirred with 500 mL fresh acetone overnight. The suspension was gravity-filtered and the solids were then suction-filtered and air-dried under a nitrogen blanket to yield 16.0 g 80%-hydrolyzed polyvinylalcohol acetoacetate.

$^1$H NMR (D$_2$O): 7.5 mol % acac (eq wt=770), from the ratio of the acetoacetate CH$_3$ (2.32 ppm) to the acetate CH$_3$ (2.1 ppm), where the acetate content was determined to be 18.2 mol % from the NMR spectrum of the parent PVOH.

Example 4

Preparation of Elvanol Acetoacetate

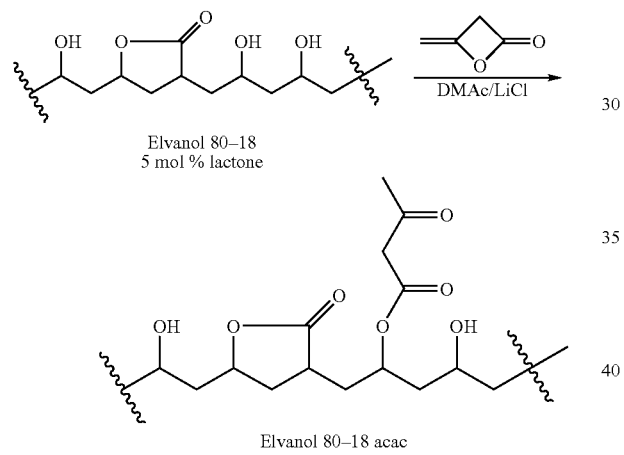

Elvanol 80–18
5 mol % lactone

Elvanol 80–18 acac

Elvanol 80-18 polyvinylalcohol (E.I. du Pont de Nemours and Company, Wilmington, Del.; Mw=80,000 Da, Mn=40,000 Da; contains 5 mol % methyl acrylate which converts to lactone on basic methanolysis) was dried in a 50° C. oven at 350 mm Hg under a nitrogen purge for 3 days. The sample weight loss was 2.8%. The dried Elvanol 80-18 (20.0 g; 400 mmol OH) was dissolved in 200 mL dry DMAc along with 5 g LiCl and 100 mg of N,N-4-dimethylaminopyridine in a 500-mL RB flask under nitrogen with stirring and heating in a 80° C. oil bath to give a clear solution. If the bath temperature was allowed to go to over 100° C., the clear solution became hazy, possibly due to crosslinking through interchain esterification of the lactone groups. The bath was cooled to 70° C. and then stirred as 4.0 mL (4.4 g; 52 mmol) 85% diketene was added; the resulting orange solution was stirred at 70° C. for 2 hr and then was precipitated by blending into 1 L methanol in a blender.

The methanol was suction-filtered off and the polymer blended with 500 mL fresh methanol and the resulting suspension was suction filtered. The polymer powder was then stirred overnight with 500 mL acetone, suction-filtered and air-dried under a nitrogen blanket to yield 20.5 g Elvanol 80-18 acetoacetate.

$^1$H NMR (D$_2$O): by ratio of the 2.35-ppm acac CH$_3$ peak to the 4.1-ppm backbone methine hydrogen (HCOH) peak the polymer contained 9.8 mol % acetoacetate groups (eq wt=530).

Example 5

Preparation of Dextran Acetoacetate

Polysaccharide Derivatized with acac Groups

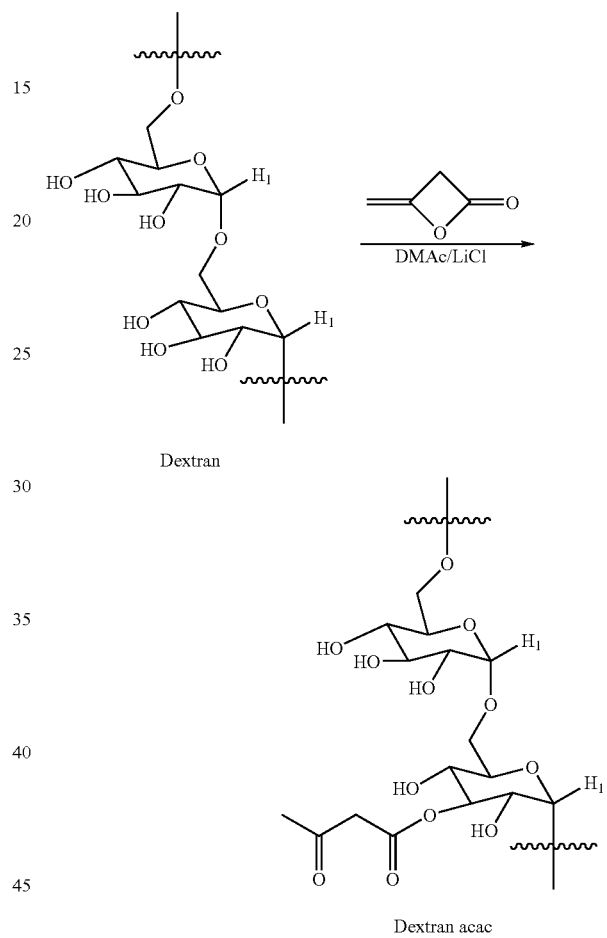

Dextran

Dextran acac

Dextran (10.0 g; Sigma D1662; Mw=40,000) was dried at 50° C./300 mm Hg in a vacuum oven with a nitrogen purge for 10 days; weight loss was 7%. The dry dextran (9.3 g; unit Mw=162.14 Da; OH eq wt=54; 172 mmol OH) was dissolved in 120 mL dry DMAc containing 6 g LiCl along with 100 mg of N,N-4-dimethylaminopyridine in a 500-mL RB flask under nitrogen with stirring and heating in a 120° C. oil bath to give a solution. The solution was cooled to 70° C. and then stirred as 2.0 mL (2.2 g; 26 mmol) diketene was added. The resulting orange solution was stirred at 70° C. overnight and then was precipitated into 1 L methanol.

The methanol was suction-filtered off, and the polymer was stirred with 400 mL fresh methanol for 30 min, and the resulting suspension was filtered. The polymer was stirred with 400 mL fresh methanol overnight and then was suction-filtered and suction-dried under a nitrogen blanket to yield 9.9 g dextran 40K (40,000 Mw) acetoacetate as a cake which could be easily crushed to fine, off-white powder.

$^1$H NMR (D$_2$O): 26 mol % acac (eq wt=710) by ratio of the H$_1$ protons (4.8-5.3 ppm) to the 2.35-ppm acac CH$_3$. Mol % acetoacetate is based on glucopyranosyl units, not free OH's, so 26 mol % means about a quarter of the sugar units bear an acac group.

Example 6

Preparation of Sorbitol Acetoacetate

Reduced Monosaccharide Derivatized with acac Groups

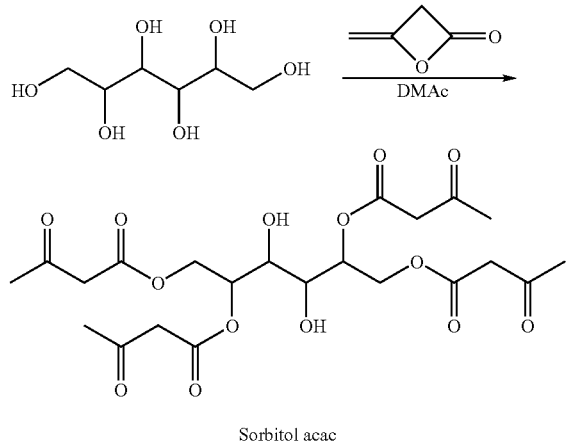

Sorbitol acac

Sorbitol (5.0 g; 165 mmol OH) was taken up in 25 mL dry DMAc in a 100-mL RB flask with a condenser and nitrogen inlet. The solution was stirred as 20 mg 4-dimethyl-aminopyridine (DMAP) was added followed by 9 mL (120 mmol) 85% diketene. The solution was stirred under nitrogen in an oil bath at 70° C. for 3 hr.

The red solution was added to 300 mL diethyl ether with stirring. The mixture was chilled and the ether was decanted off. The liquid residue was stirred with 100 mL fresh ether, chilled and decanted again. The liquid product was placed in a roto-evaporator to remove dissolved ether and then was held under vacuum at RT overnight to yield 12.8 g sorbitol acetoacetate with a degree of substitution of about 3.7 acac groups per sorbitol (eq wt-130).

Example 7

Preparation of Pentaerythritol Ethoxylate Acetoacetate

Low Molecular Weight Polyol Derivatized with acac Groups

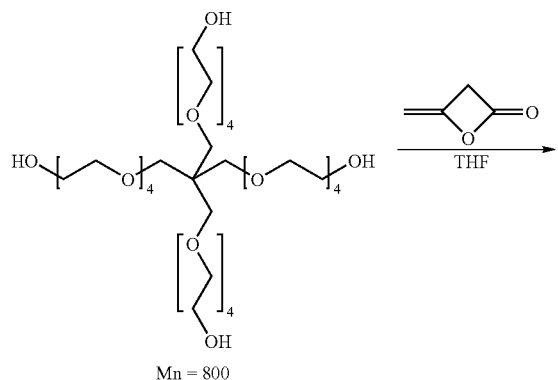

Mn = 800

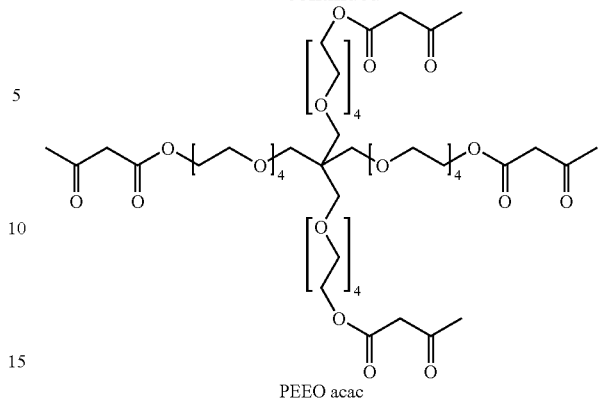

PEEO acac

A mixture of 10.0 g (50 mmol OH) pentaerythritol ethoxylate (15/4 EO/OH; Mn=797 Da; Aldrich #41,873-0) and 20 mg of N,N-4-dimethylaminopyridine was dissolved in 50 mL anhydrous THF in a 200-mL RB flask with a condenser under nitrogen. The solution was stirred as 5.6 mL (6.1 g; 73 mmol) 85% diketene was added. The solution became hot as the diketene reacted. The orange solution was stirred at reflux in a 80° C. oil bath for 2 hr. Then, 1 mL (30 mmol) methanol was added and the mixture was stirred for 15 min and filtered through a 2.5 cm bed of activity 1 basic alumina. The filtrate was placed in a roto-evaporator in a hot water bath and held under high vacuum for 1 hr to yield 9.6 g clear light brown liquid pentaerythritol ethoxylate acetoacetate (PEEO acac). $^1$H NMR (CDCl$_3$): the tetraol appeared to be totally acetoacetylated (eq wt=285).

Example 8

Preparation of Star PEG Tetraacetoacetate

Branched Polyether Derivatized with acac Groups

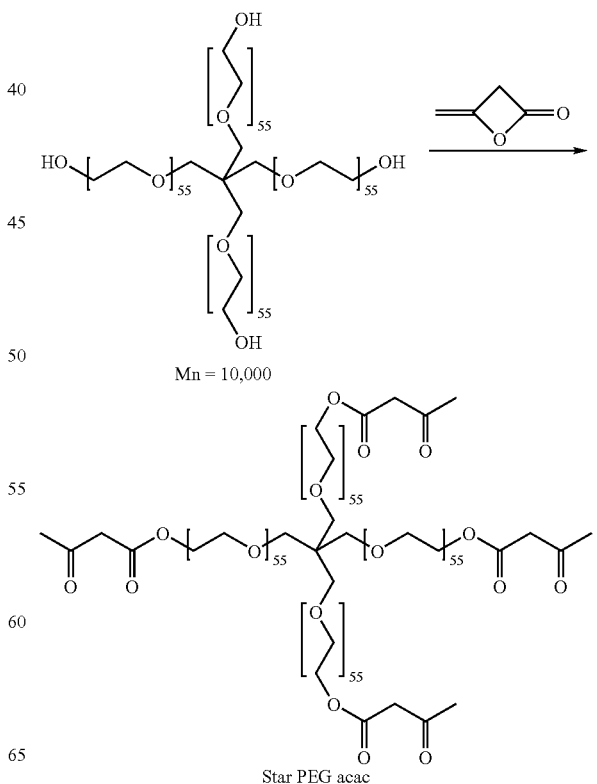

Star PEG acac

A solution of 1.0 g 4-armed star PEG 10K (0.4 mmol OH; Mn=10,000 Da; Shearwater Polymers Inc, now Nektar Transforming Therapeutics, Huntsville, Ala.)) in 10 mL THF in a scintillation vial was stirred with 0.5 mL diketene and 30 mg 4-dimethylaminopyridine (DMAP) in an oil bath at 50° C. for 2 hr. The solution was added to 100 mL ether and chilled in an ice bath. The precipitate was suction filtered, washed several times with ether and dried under suction under a nitrogen blanket to yield 0.86 g star PEG tetraacetoacetate. NMR (CDCl$_3$) indicated 95% conversion to acetoacetate ends (eq wt=2,500) by comparison of the integral of the original terminal hydroxymethyene peak at 3.62 ppm with the integral of the product terminal acetoacetatomethylene peak at 4.30 ppm.

Example 9

Preparation of Amino-Terminated Polyethyleneoxide-Polypropyleneoxide Acetoacetamide (XTJ-502 acac)

Polyamino Compounds Derivatized with Acetoacetamide Groups

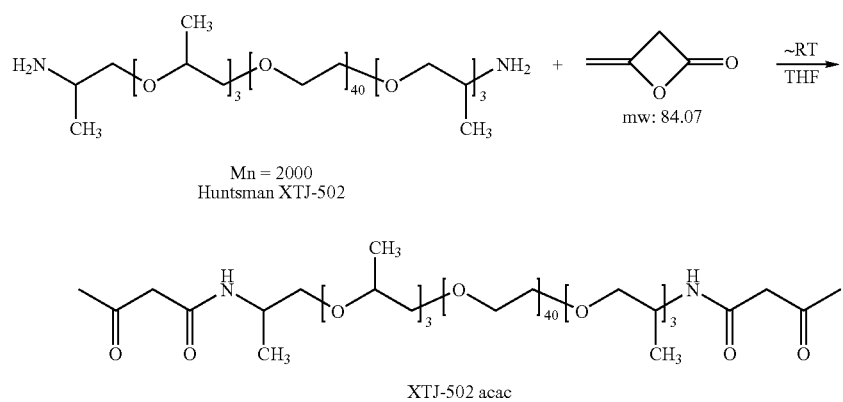

XTJ-502 acac

A solution of 1.00 mL (1.1 g; 13 mmol) 85% diketene in 5 mL THF was stirred under nitrogen at RT as a solution of 2.00 g polyethyleneoxide-polypropyleneoxide diamine (Huntsman XTJ-502, Huntsman LLC, Houston, Tex.; Mn=2000 Da; 2.0 mmol NH$_2$) and 20 mg dimethylaminopyridine in 9 mL THF was added dropwise via syringe over 8 min (~2 drops/sec). The flask quickly grew hot during the first mL or so of diamine addition, so a water cooling bath was used for the remainder of the addition. If the reaction was allowed to get too warm, chain extension resulted from coupling of underivatized amino ends with acac ends. The red mixture was allowed to stand at RT for 24 hr. The product was precipitated by stirring with 125 mL chilled ether; filtration and high vacuum drying yielded the acetoacetamide derivative XTJ-502 acac.

$^1$H NMR (CDCl$_3$) showed two closely-spaced pairs of acac CH$_3$ peaks at 2.264 and 2.266 (total: about 5H) and at 2.272 and 2.274 ppm (total about 1H). Eq wt=1200.

Example 10

Preparation of Branched Polyester-Polyether Acetoacetate

Condensation Product Derivatized with acac Groups

A branched polyester-polyether acetoacetate was prepared by reacting tetramethyl cyclopentane-1,2,3,4-tetracarboxylate with poly(ethylene glycol) and then reacting the resulting branched polyester-polyether with diketene.

Preparation of Tetramethyl Cyclopentane-1,2,3,4-tetracarboxylate

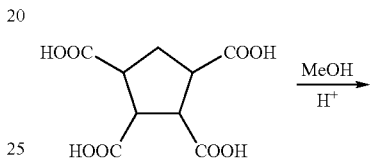

-continued

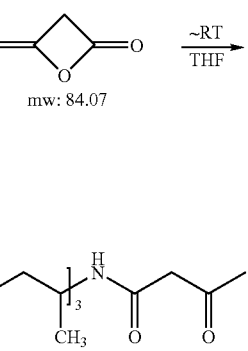

A mixture of 10 g cyclopentane-1,2,3,4-tetracarboxylic acid (Aldrich; #C112100), 100 mL reagent methanol and 1 mL acetyl chloride was stirred at reflux for 3 hr. The solution was evaporated to dryness in a roto-evaporator and held under high vacuum for 15 min to afford a yellow oil, which was taken up in 50 mL dichloromethane. This solution was filtered through a bed of basic alumina to remove acidic impurities and the filtrate was clarified with a syringe filter. The clear, colorless solution was placed in a roto-evaporator and held under high vacuum overnight to yield 6.6 g (54%) tetramethyl cyclopentane-1,2,3,4-tetracarboxylate as a clear viscous liquid. IR: 1736 cm$^{-1}$ (ester). $^1$H NMR (CDCl$_3$): 2.43 ppm (m, 1H); 2.80 (m, 1H); 3.10 (m, 2H); 3.40 (m, 2H); 3.69 (s, 12H, COOCH$_3$).

Preparation of Branched Polyester-Polyether

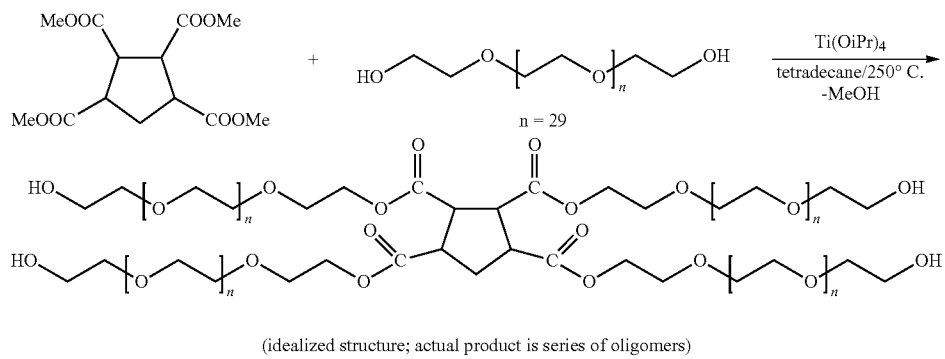

(idealized structure; actual product is series of oligomers)

A mixture of 20.0 g (Mn=1360 Da; 4.4 equivalents) polyethylene glycol PEG 1500 (Aldrich; #202436), 1.0 g (3.31 mmol) tetramethyl cyclopentane-1,2,3,4-tetracarboxylate, 5 drops titanium tetraisopropoxide and 30 mL tetradecane was combined in a 100-mL round bottom flask with side arm thermocouple well, condenser and Dean-Stark trap. The reaction mixture was bubbled with nitrogen 5 min to remove oxygen from the system before heating and the mixture was magnetically stirred and heated to reflux (85 V heating mantle) under nitrogen. It took 30 min to heat from RT to 240° C., at which point a timer was started. Real reflux began at 250° C., about 5 min after the timer was started. At 15 min the polymer melt began to look more viscous, so the heating mantle was removed; at this point 0.3 mL of methanol had distilled.

The mixture was cooled, the tetradecane was decanted, and the branched polyester-polyether polymer was crushed in a mortar and washed with several changes of hexane, suction-filtered dry and held under high vacuum at RT.

$^1$H NMR (CDCl$_3$) indicated 88% conversion to cyclopentane PEG tetraester; there will be 0.9 mol excess PEG (per cyclopentane PEG tetraester) present as well. ICI viscosity (100° C.; allow polymer melt to stand at temperature under spindle for 5 min; then start spindle rotating and take reading after 15 sec): 21 poise.

Preparation of Branched Polyester-Polyether Acetoacetate

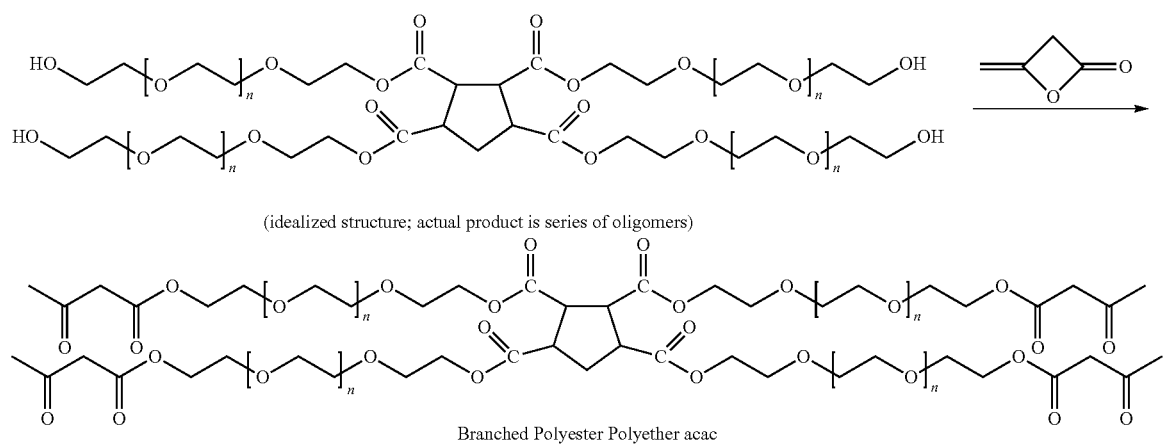

A solution of 2.0 g branched polyester polyether (1.6 mmol OH) in 10 mL THF in a scintillation vial was stirred with 0.5 mL diketene and 30 mg 4-dimethylaminopyridine (DMAP) in an oil bath at 50° C. for 2 hr. The solution was cooled and added to 100 mL ether and the suspension was chilled in an ice bath. The precipitate was suction filtered, washed several times with ether and dried under suction under a nitrogen blanket to yield 1.8 g branched polyester polyether acetoacetate (eq wt=1670). By NMR (CDCl$_3$), the free OH ends were about 95% converted to acetoacetates: 2.27 ppm (s, a); 3.48 (s, b); 3.64 (s, e); 3.71 (t, d, d'); 4.22 (t, c'); 4.30 (t, c).

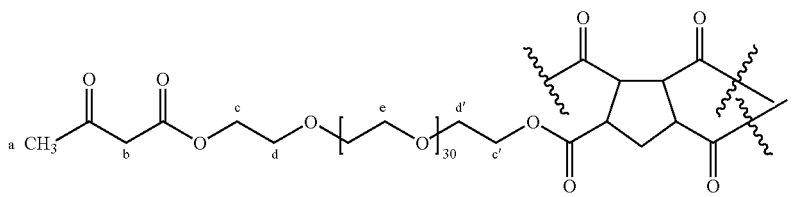

Example 11

Preparation of Polyvinylalcohol 4-Aminobutyral Acetal

Reference: U.S. Pat. No. 5,397,436; See Also WO 03/35122

Intermediate for Example 15, 21, 34, and 35

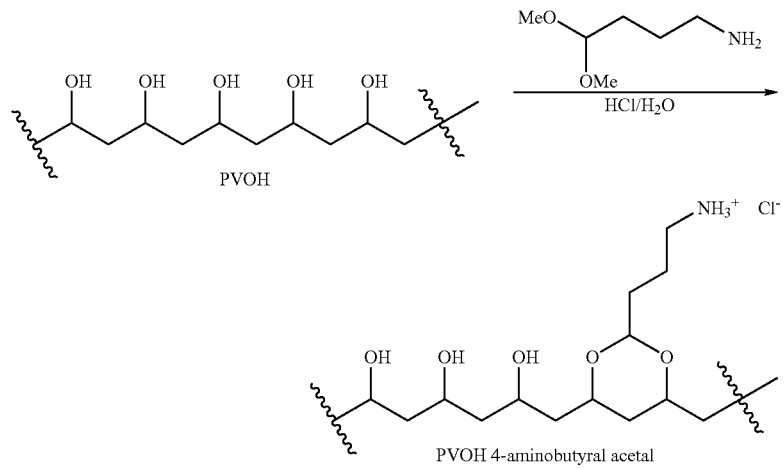

A mixture of undried polyvinylalcohol (50 g; Aldrich #36, 313-8; Mw=31,000-50,000; 1.14 mol OH) and 280 mL water was stirred in a 90° C. oil bath in a 500-mL RB flask under nitrogen to give a solution. The solution was cooled to 75° C. and 18 g (180 mmol) concentrated hydrochloric acid was added, followed by 20 g (21 mL; 150 mmol) 4-aminobutyraldehyde dimethyl acetal (TCI America, Portland, Oreg.; #A1364; mw=133.19). The solution was stirred at 75° C. for 6 hr and then was cooled and divided into two equal portions of 150 mL each.

One 150-mL portion was stirred as 6 g (57 mmol; 104 mmol base) sodium carbonate was added and stirred 1 hr until gas evolution stopped. The solution was poured into an ~45 cm section of Spectra/Por® MWCO 3500 dialysis membrane (Spectrum Laboratories, Inc., Rancho Dominguez, Calif.) and the membrane was clamped on both ends and hung in a large beaker of deionized water with stirring for 24 hr; the water was changed the next morning at 8:00 am, at 11:00 am and again at 2:00 pm. Then at 5:00 pm, the solution was frozen in two portions and placed on a lyophilizer over the weekend to yield 22.8 g polyvinylalcohol 4-aminobutyral acetal. $^1$H NMR (D$_2$O): 2.78 ppm (br s, C$\underline{H}_2$NH$_2$, 83%); 3.02 ppm (t, C$\underline{H}_2$NH$_3^+$, 17%); the product had 83% free amine and 17% amine salt. By ratio of the backbone CH$_2$ integral (minus overlapping aminoacetal peaks) at 1.5-2 ppm to the combined C$\underline{H}_2$NH$_2$/$_3$ integrals, the product contained 12.9 mol % amine (eq wt=420). The pH of an aqueous solution was 10.

The remaining 150 mL of solution was precipitated in a blender into 1000 mL acetone. The polymer, which precipitated into a rubber ball, was cut up into small pieces, stirred overnight with acetone, filtered dry and held under vacuum with a nitrogen bleed for 2 days. This product (44.3 g) which contained about 20 wt % acetone, was taken up in 200 mL deionized water, filtered through a Millipore cellulose prefilter and dialyzed in a Spectra/Por® 3500 MWCO membrane tube against slowly flowing deionized water for 6 hr. The solution was stirred overnight with 6.0 g (57 mmol; 113 mmol base) sodium carbonate and then was again dialyzed against flowing deionized water for 2 hr followed by lyophilization to yield 30.8 g polyvinylalcohol 4-aminobutyral acetal. $^1$H NMR (D$_2$O): 73% free amine and 27% amine salt; 13.2 mol % amine (eq wt=415).

Example 12

Preparation of Poly(vinylalcohol-vinylamine) Copolymer

Reference: U.S. Pat. No. 5,397,436; See Also WO 02/072361

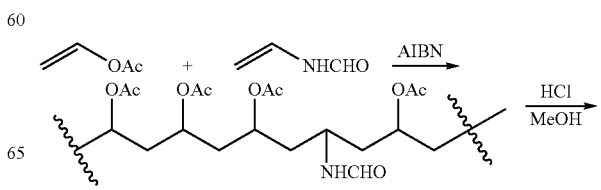

-continued

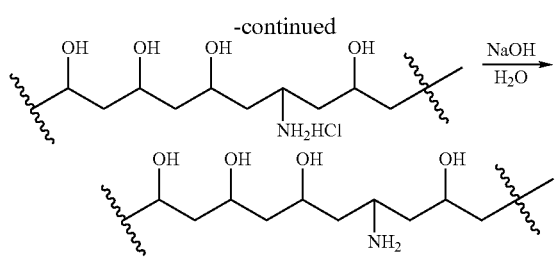

Vinyl acetate (Aldrich # V503) was filtered through a ¼ inch (0.6 cm) layer of basic alumina to remove inhibitor; N-vinylformamide (Aldrich #447331) was used as received. A solution of 0.2 g of sodium dodecylbenzenesulfonate (Aldrich #289957) and 0.2 g of sodium dihydrogen phosphate in 80 mL of deionized water was placed in a 250-mL, 4-neck RB flask with condenser and nitrogen inlet, thermometer, dropping funnel and magnetic stirrer. The flask was swept with nitrogen and was stirred in a 72° C. water bath until the solution temperature was 65° C.; then 0.1 g of AIBN (2,2'-azobisisobutyronitrile; Aldrich #441090) initiator was added. A solution of 40 g vinyl acetate, 4 g N-vinylformamide and 0.3 g AIBN was placed in the dropping funnel and 5 mL of this monomer solution was added to the flask with stirring.

Five-milliliter aliquots of monomer were added every 20 min until 20 mL had been added (at 1 hr); then the mixture was stirred at 70° C. for 1 hr more. After this the remainder of the monomer was added at a rate of 5 mL every 20 min. After the monomer addition was completed at 4 hr, the mixture was stirred at 70° C. for an additional 3 hr and then allowed to cool to RT. The product was a suspension of filterable tiny (100-1000 μm) polymer beads. The beads were filtered and washed several times with hot water and then allowed to stand in water for 2 days. The beads were again filtered and dried overnight at 70° C. in a vacuum oven at 350 mm Hg with a nitrogen sweep to yield 39.0 g poly(vinyl acetate-co-vinylformamide). The polymer was slightly soft at 70° C. but hard and glassy at room temperature. $^1$H NMR (DMSO-d6): by ratio of the 3.80-ppm N-vinylformamide methine peak (a; 1.24) to the 4.78-ppm vinyl acetate methine peak (b; 13.40), the polymer has 8.5 mol % N-vinylformamide incorporation (hydrolyzed $NH_2$ eq wt~520).

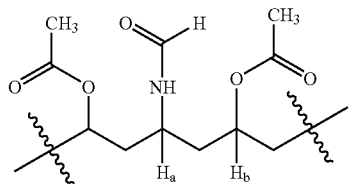

The poly(vinyl acetate-co-vinylformamide) copolymer (25.1 g) was stirred at reflux with 200 mL of methanol containing 6 mL of concentrated HCl and 5 mL of water for 5 hr, yielding a clear solution which was allowed to stand at RT overnight. The solution became a rubbery gel; this was blended with several changes of acetone to precipitate the hydrolyzed polymer HCl salt, which was dried under nitrogen in the vacuum oven at 75° C. (yield: 15 g). By $^1$H NMR (DMSO-d6) about 20% of the acetates (proton peaks~2 ppm) still remained unhydrolyzed, so the product was stirred at reflux with a mixture of 150 mL methanol and 5 mL concentrated HCl overnight. The methanol was filtered off, and the rubbery, methanol-insoluble product was stirred with 100 mL DI water at 90° C.; this solution was filtered first through a screen to remove a small amount of gel and then through a Millipore cellulose prefilter under pressure. The filtered solution was basified to pH 9.0 with 10% NaOH and the basic solution was dialyzed overnight against deionized water in a Membracel 3.5K MWCO dialysis membrane tube. Lyophilization yielded 8.7 g poly(vinylalcohol-co-vinylamine).

Example 13

Polyvinylalcohol Acetoacetate-Polyamine Hydrogels

Hydrogel disks were made from various PVOH acetoacetate/polyamine combinations and the properties were determined as a function of PVOH Mw, acac content, amine type and acac:amine stoichiometry. The results are shown in Tables 1-5 below.

Aqueous Solutions:
  25 wt % PVOH acac (Mw=13-32K; 3.5 mol % acac; eq wt=1350)
  25 wt % PVOH acac (Mw=13-32K; 10.0 mol % acac; eq wt=525)
  25 wt % PVOH acac (Mw=13-32K; 11.4 mol % acac; eq wt=470)
  20 wt % PVOH acac (Mw=31-50K; 4.2 mol % acac; eq wt=1140)
  20 wt % PVOH acac (Mw=31-50K; 5.4 mol % acac; eq wt=900)
  20 wt % PVOH acac (Mw=31-50K; 9.0 mol % acac; eq wt=575)
  20 wt % PVOH acac (Mw=31-50K; 12.4 mol % acac; eq wt=440)
  50 wt % DODDA: 4,9-dioxadodecane-1,12-diamine (Aldrich #22,244-7)
  25 wt % DAN: 1,9-diaminononane (Aldrich #18,712-7)
  25 wt % PEI 600: polyethyleneimine, Mn=600 Da/Mw=800 Da (Aldrich #40,871-9)
  25 wt % BAPT: poly-1,4-butanediol (polyTHF; n=9) with 3-aminopropyl ends
  25 wt % BAPP: N,N'-bis(3-aminopropyl)piperazine (Aldrich #23,948-8)
  25 wt % ED-600: Huntsman XTJ-500 (Jeffamine ED-600); PEG 500 with 2-aminopropyl ends
  25 wt % T-403: Huntsman Jeffamine T-403; propylene oxide-trimethylolpropane adduct (n~5) with 2-aminopropyl ends
  20 wt % LPEI 420: linear polyethyleneimine, Mn=423 Da (Aldrich #46,853-3)
  10 wt % ADH: adipic dihydrazide (Aldrich #21,782-4)

Hydrogel Disks:
  The Luer fitting end was cut off a plastic disposable 10-mL syringe so that the end was open. The syringe plunger was withdrawn to about 2.5 cm below the open end and a 2-3 mm thick silicone rubber disk of the same diameter as the inside diameter of the syringe barrel was inserted and pressed down onto the top of the plunger. This disk insert provides a flat bottom in the syringe barrel. The syringe was held upright and the reactive polymer solutions (PVOH acac and amine) were added to the syringe and mixed vigorously with a thin spatula until the mixture began to thicken. The syringe was then allowed to stand upright for 15 min as the mixture completed crosslinking; the open barrel end was covered with aluminum foil to prevent the hydrogel from drying out during this time. After 15 min, the plunger was carefully pushed out to eject the hydrogel disk, which was cut off with razor blade. The disks were about 1.4 cm in diameter and 2-3 mm thick.

Mechanical Tests:

Modulus:
  hard: comparable to a pencil eraser;
  stiff: comparable to a gum eraser;
  firm: comparable to cured acrylic caulk;
  soft: comparable to a Jello "jiggler" or foamed rubber.

A very rough correlation of the "modulus" designations with the Shore A hardness scale is as follows:
  Hard: Shore A~40
  Stiff: Shore A~30
  Firm: Shore A~10-20
  Soft: Shore A<5

Stretch: hold hydrogel disk in fingers and pull, roughly estimate elongation to break:
  <10%, >10%, 25%, >25%

Bend: bend hydrogel disk in fingers:
  snap<45°, snap<90°, snap<180°, bend 180° without breaking 24-hr Swell: weigh as-molded disk, soak 24 hr in deionized water, pat dry and re-weigh;
  Swell=(final wt−initial wt)/initial wt Roll test: roll a piece of hydrogel disk between finger and thumb with some pressure:
  gel does not break (pass) or else crumbles (fail)

TABLE 1

Gelation of PVOH acac (3.5% acac/Mw = 13-23 kDa) with Various Polyamines

| Exp # | Amine | PVOH acac eq wt | acac:NH$_2$ | Expresses water on crosslinking? | Modulus | Stretch % | Bend disk | 24 hr Swell | Roll test |
|---|---|---|---|---|---|---|---|---|---|
| 1 | DODDA  | 1350 | 1:1.5 | no | very soft | >25 | 180°  | 1.3 | pass |
| 2 | PEI 600 | 1350 | 1:1.5 | no | soft      | <10 | <180° | 0.3 | fail |
| 3 | BAPT   | 1350 | 1:1.5 | no | very soft | <10 | 180°  | 0.3 | fail |
| 4 | T-403  | 1350 | 1:1.5 | no | very soft | >10 | 180°  | 1.8 | pass |

TABLE 2

Gelation of PVOH acac (10-11 mol % acac/Mw = 13-23 kDa) with Various Polyamines

| Exp # | Amine | PVOH acac eq wt | acac:NH$_2$ | Expresses water on crosslinking? | Modulus | Stretch % | Bend disk | 24 hr Swell | Roll test |
|---|---|---|---|---|---|---|---|---|---|
| 1 | DODDA  | 470 | 2.5:1 | no  | soft  | 10  | <180° | 1.2  | fail |
| 2 | DODDA  | 525 | 1.8:1 | yes | stiff | <10 | <180° | −0.1 | fail |
| 3 | PEI 600 | 470 | 2.5:1 | yes | stiff | 0   | <90°  | 0.4  | fail |
| 4 | PEI 600 | 525 | 1.8:1 | yes | stiff | <10 | <90°  | 0.1  | fail |
| 5 | BAPT   | 470 | 2.5:1 | no  | soft  | 10  | 180°  | 0.4  | pass |
| 6 | BAPT   | 525 | 1.8:1 | yes | soft  | <10 | 180°  | 0.4  | —    |
| 7 | T-403  | 470 | 2.5:1 | no  | soft  | >10 | 180°  | 0.9  | fail |

TABLE 3

Gelation of PVOH acac (4-5 mol % acac/Mw = 31-50 kDa) with Various Polyamines

| Exp # | Amine | PVOH acac eq wt | acac:NH$_2$ | Expresses water on crosslinking? | Modulus | Stretch % | Bend disk | 24 hr Swell | Roll test |
|---|---|---|---|---|---|---|---|---|---|
| 1 | DODDA   | 1140 | 1:1.2 | no | soft      | >10 | 180°  | 0.9 | pass |
| 2 | DAN     | 1140 | 1:1.2 | no | soft      | 10  | 180°  | 0.3 | fail |
| 3 | PEI 600 | 1140 | 1:1.2 | no | soft      | 10  | <180° | 0.2 | fail |
| 4 | PEI 600 | 900  | 1:1.2 | no | soft      | >10 | <180° | 0.1 | fail |
| 5 | PEI 600 | 900  | 1.6:1 | no | soft      | 25  | 180°  | 0.8 | pass |
| 6 | BAPT    | 1140 | 1:1.2 | no | soft      | 25  | 180°  | 0.3 | fail |
| 7 | BAPP    | 1140 | 1:1.2 | no | soft      | 25  | 180°  | 1.6 | pass |
| 8 | BAPP    | 900  | 1:1.2 | no | soft      | 25  | 180°  | 0.5 | pass |
| 9 | T-403   | 1140 | 1:1.2 | no | very soft | >25 | 180°  | 1.3 | pass |

TABLE 4

Gelation of PVOH acac (9 mol % acac/Mw = 31-50 kDa) with Various Polyamines

| Exp # | Amine | PVOH acac eq wt | acac:NH$_2$ | Expresses water on crosslinking? | Modulus | Stretch % | Bend disk | 24 hr Swell | Roll test |
|---|---|---|---|---|---|---|---|---|---|
| 1 | DAN | 575 | 1.5:1 | yes | soft | 10 | 180° | 0.1 | fail |
| 2 | PEI 600 | 575 | 1.5:1 | yes | stiff | 0 | <180° | 0.2 | fail |
| 3 | PEI 600 | 575 | 2:1 | no | stiff | <10 | <180° | 0.4 | fail |
| 4 | BAPT | 575 | 1.2:1 | yes | very soft | >10 | 180° | 0.1 | fail |
| 5 | BAPP | 575 | 1.5:1 | no | soft | 10 | <180° | 0.7 | fail |

TABLE 5

Gelation of PVOH acac (12 mol % acac/Mw = 31-50 kDa) with Various Polyamines

| Exp # | Amine | PVOH acac eq wt | acac:NH$_2$ | Gel time min | Expresses water on crosslinking? | Modulus | Stretch % | Bend disk | Roll test |
|---|---|---|---|---|---|---|---|---|---|
| 1 | ADH | 440 | 1:1 | 2:35 | yes | firm | <10 | >90° | fail |
| 2 | ADH | 440 | 2:1 | 2:20 | yes | firm | 10 | <180° | fail |
| 3 | LPEI 420 | 440 | 1:1 | 0:30 | yes | firm | <10 | <180° | fail |
| 4 | LPEI 420 | 440 | 2:1 | 0:25 | yes | soft | 10 | <180° | fail |

This example demonstrates the ability of aqueous mixtures of polyvinylalcohol acetoacetate and various crosslinking amines to react quickly to form hydrogels, which could function as bioadhesives.

Example 14

Polyvinylalcohol Acetoacetate-Polyethyleneimine 600 Hydrogels

Polyethyleneimine (Mn=600 Da; PEI 600; Aldrich #40,871-9) was used to crosslink polyvinylalcohol acetoacetate to form hydrogels. See Example 13 for a description of making hydrogel disks and mechanical testing. The hydrogel disks were soaked in pH 7.4 Tris buffer, (HOCH$_2$)$_3$CNH$_2$, for 16 days and some mechanical properties were redetermined. The results are described in Tables 6-7.

Aqueous Solutions:

20 wt % PVOH acac (Mw=31-50K; 10.4 mol % acac; eq wt=510)

20 wt % PEI 600 (polyethyleneimine Mn=600 Da, Aldrich #40,871-9; eq wt~150)

TABLE 6

Gelation of PVOH acac with Polyethyleneimine 600

| Exp # | acac:NH$_2$ | Gel Time min | Expresses water on crosslinking? | Modulus | Stretch % | Bend disk | 24 hr Swell | Roll test |
|---|---|---|---|---|---|---|---|---|
| 1 | 3:1 | 0:35 | yes | firm | 10 | <180° | 0.5 | fail |
| 2 | 2.5:1 | 0:35 | yes | firm | 10 | <180° | 0.2 | fail |
| 3 | 2:1 | 0:35 | yes | firm | 10 | <180° | 0 | fail |
| 4 | 1.5:1 | 0:35 | yes | stiff | 0 | <90° | −0.2 | fail |
| 5 | 1:1 | 0:35 | yes | stiff | 0 | <45° | −0.3 | fail |

TABLE 7

Soak Hydrogel Disks in pH 7.2 Tris ((HOCH$_2$)$_3$CNH$_2$) Buffer for 16 Days

| Exp# | Hydrogel Properties after Soaking |
|---|---|
| 1 | nearly dissolved |
| 2 | very flabby - almost liquid |
| 3 | highly swollen but held shape and could be handled; no strength |
| 4 | swollen; not strong but could be bent double and stretched >10% |
| 5 | firm swollen rubber, snap <45° bend, a little stretch |

This example demonstrates the ability of aqueous mixtures of various stoichiometry of polyvinylalcohol acetoacetate and polyethyleneimine to react quickly to form hydrogels which could function as bioadhesives and which maintain good mechanical properties on long exposure to water.

Example 15

Elvanol 80-18 Acetoacetate-Polyethyleneimine Hydrogels

A 9 wt % solution of the Elvanol 80-18 acetoacetate of Example 4 was made up in water. This solution was reacted with various proportions of polyethyleneimine 600 (PEI Mn=600 Da; Aldrich #40,871-9) in aqueous solution to make hydrogel disks as described in Example 13. The gel times were all on the order of 30-50 sec. The parent polyvinylalcohol Elvanol 80-18 with no acetoacetate groups will also crosslink with polyallylamine through its lactone groups to make a soft hydrogel. However, the acetoacetylated polymer was much more reactive and made stronger hydrogels. Results are shown in Table 8.

Aqueous Solutions:

9 wt % Elvanol 80-18 acac (eq wt=530; Mw=40-80,000; Elvanol 80-18 also contains 5 mol % lactone, eq wt=910)

25 wt % PEI 600 (Aldrich #40,871-9; Mn=600 Da; $NH_2$ eq wt~150)

Hydrogels:

The Luer fitting end was cut off a plastic disposable 3-mL syringe so that the end was open. The syringe was held upright and the plunger was withdrawn to about 2.5 cm below the open end and the reactive polymer solutions (PVOH acac and PVOH amine) were added to the syringe and mixed vigorously with a thin spatula for 5 sec. Then the syringe was inverted and the plunger was quickly depressed to extrude the liquid contents onto a sheet of PTFE-coated aluminum foil. The hydrogel "puddle" was allowed to cure for 3 min and then was lifted off the sheet with a spatula. The hydrogels were tack-free in 1-2 min.

TABLE 9

Gelation of PVOH acac (12 mol % acac/Mw = 31-50K) with Polyvinylalcohol 4-Aminobutyral Acetal

| Exp # | PVOH Amine | acac:$NH_2$ | Gel Time min | Expresses water on crosslinking? | Modulus | Stretch % | Bend disk | 24 hr Swell | Roll test |
|---|---|---|---|---|---|---|---|---|---|
| 1 | 20 wt % | 2:1 | 0:10 | yes | soft | <10 | 180° | 0.9 | fail |
| 2 | 20 wt % | 3:1 | 0:10 | yes | soft | 10 | <180° | 0.9 | fail |
| 3 | 15 wt % | 2:1 | 0:10 | yes | soft | 10 | 180° | 0.8 | fail |
| 4 | 15 wt % | 3:1 | 0:12 | yes | soft | <10 | 180° | 1.6 | fail |

TABLE 8

Gelation of Elvanol 80-18 acac with PEI 600

| Exp # | μL Elvanol acac | μL PEI 600 | acac:$NH_2$ | Physical Properties | After soaking 90 hr in pH 7.4 Tris buffer |
|---|---|---|---|---|---|
| 1 | 400 | 41 | 1:1 | stiff rubber | soft rubber |
| 2 | 400 | 31 | 1:0.75 | firm rubber | soft rubber |
| 3 | 400 | 21 | 1:0.5 | firm rubber | soft rubber |
| 4 | 400 | 16 | 1:0.4 | firm rubber | very soft rubber |

This example demonstrates the ability of aqueous mixtures of lactone-containing polyvinylalcohol acetoacetate and polyethyleneimine to react quickly to form hydrogels, which could function as bioadhesives.

Example 16

Polyvinylalcohol Acetoacetate-Polyvinylalcohol 4-Aminobutyral Acetal ("PVOH Amine") Hydrogels The polyvinylalcohol 4-aminobutyral acetal ("PVOH amine") of Example 11 was used to crosslink polyvinylalcohol acetoacetate to form hydrogels. These hydrogels are described in Table 9. See Example 13 for a description of hydrogel mechanical testing.

Aqueous Solutions:

20 wt % PVOH acac (Mw=31-50K; 12.4 mol % acac; eq wt=440)

20 wt % PVOH amine: PVOH 4-aminobutyral acetal (Mw=31-50K; 83% free $NH_2$, eq wt=420)

15 wt % PVOH amine: PVOH 4-aminobutyral acetal (Mw=31-50K; 83% free $NH_2$, eq wt=420)

A tiny amount of Rhodamine B dye was added to the PVOH 4-aminobutyral acetal solutions to observe completeness of mixing; striations and non-uniformity in the color of the cured hydrogel will reveal poor or incomplete mixing.

This example demonstrates the ability of aqueous mixtures of polyvinylalcohol acetoacetate and polyvinylalcohol 4-aminobutyral acetal to react quickly to form hydrogels, which could function as bioadhesives.

Example 17

Polyvinylalcohol Acetoacetate-3-Aminopropyltrimethoxysilane Hydrogels

3-Aminopropyltrimethoxysilane (APS) was used to crosslink polyvinylalcohol acetoacetate of various Mw and acac content to form hydrogels. See Example 13 for a description of making hydrogel disks and mechanical testing. The hydrogel disks were soaked in pH 7.4 Tris buffer, $(HOCH_2)_3CNH_2$, for 6 days and some mechanical properties were redetermined. The results are described in Tables 10-11.

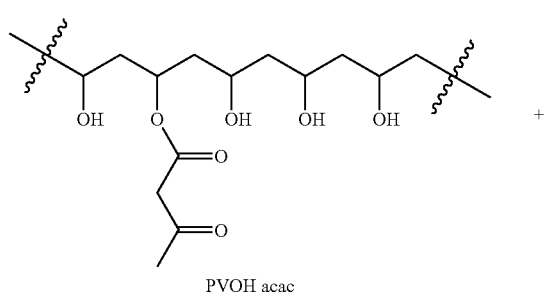

PVOH acac

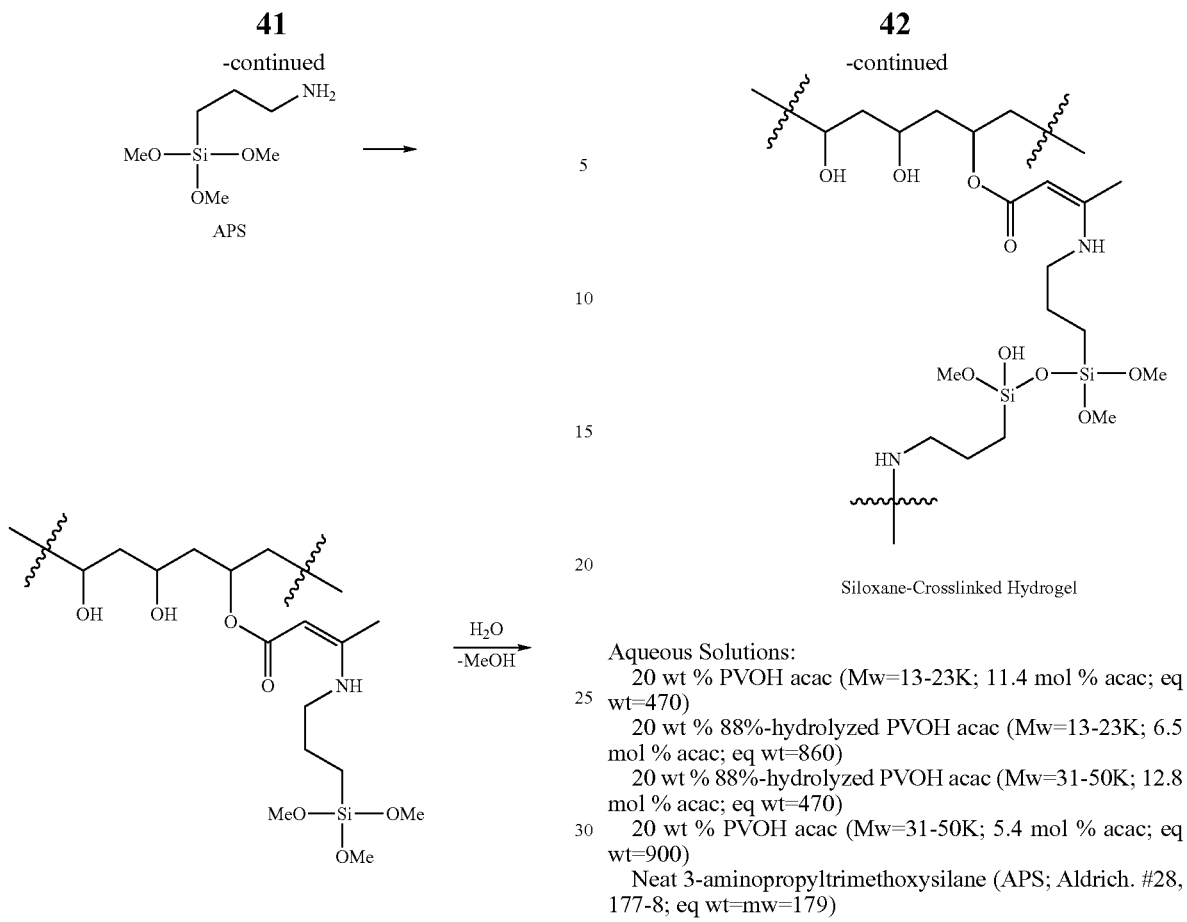

Aqueous Solutions:
20 wt % PVOH acac (Mw=13-23K; 11.4 mol % acac; eq wt=470)
20 wt % 88%-hydrolyzed PVOH acac (Mw=13-23K; 6.5 mol % acac; eq wt=860)
20 wt % 88%-hydrolyzed PVOH acac (Mw=31-50K; 12.8 mol % acac; eq wt=470)
20 wt % PVOH acac (Mw=31-50K; 5.4 mol % acac; eq wt=900)
Neat 3-aminopropyltrimethoxysilane (APS; Aldrich. #28,177-8; eq wt=mw=179)

TABLE 10

Gelation of PVOH acac with 3-Aminopropyltrimethoxysilane

| Exp # | PVOH acac eq wt | PVOH Mw, K | acac:NH₂ | Gel Time min | Expresses water on crosslinking? | Modulus | Stretch % | Bend disk | 24 hr Swell | Roll test |
|---|---|---|---|---|---|---|---|---|---|---|
| 1 | 470 | 13-23 | 1:1 | 0:20 | yes | hard | 0 | <45° | −0.1 | fail |
| 2 | 470 | 13-23 | 2:1 | 0:50 | yes | firm | <10 | <180° | 0 | fail |
| 3 | 470 | 13-23 | 3.3:1 | 1:43 | no | soft | >10 | <180° | 0.4 | fail |
| 4 | 860 | 13-23 | 1:1 | 0:55 | yes | stiff | <10 | <90° | 0 | fail |
| 5 | 860 | 13-23 | 2:1 | 2:10 | no | soft | <10 | <180° | 0.6 | fail |
| 6 | 860 | 13-23 | 3.3:1 | 3:10 | no | soft | >25 | 180° | 1.5 | pass |
| 7 | 470 | 31-50 | 1:1 | 0:25 | yes | hard | 0 | <45° | −0.1 | fail |
| 8 | 470 | 31-50 | 2:1 | 0:25 | yes | firm | <10 | <180° | 0.1 | fail |
| 9 | 470 | 31-50 | 3.3:1 | 0:25 | yes | soft | <10 | <180° | 0.1 | fail |
| 10 | 900 | 31-50 | 1:1 | 0:40 | yes | firm | <10 | <180° | 0 | fail |
| 11 | 900 | 31-50 | 2:1 | 1:00 | no | soft | 25 | 180° | 0.6 | fail |
| 12 | 900 | 31-50 | 3.3:1 | 2:25 | no | soft | >25 | 180° | 1.4 | pass |

TABLE 11

Soak Hydrogel Disks in pH 7.2 Tris ((HOCH$_2$)$_3$CNH$_2$) Buffer for 6 Days

| Exp # | Hydrogel Properties after Soaking |
|---|---|
| 1 | hard rubber, snap 45° bend |
| 2 | firm rubber, snap 90° bend |
| 3 | swollen and flabby, coherent but little strength |
| 4 | soft swollen rubber, bend 180°, 10% stretch |
| 5 | dissolved at 5 days |
| 6 | dissolved |
| 7 | hard rubber, snap 45° bend |
| 8 | firm swollen rubber, bend >90° |
| 9 | soft rubber, bend 180°, weak |
| 10 | soft swollen rubber, bend 180° |
| 11 | very flabby and swollen, no strength |
| 12 | dissolved |

3-Aminopropyltriethoxysilane (APES) also crosslinked PVOH acac. Gelation times were 2-3× longer than with the corresponding methoxy silane APS. Otherwise the hydrogel properties were similar. Use of the ethoxy silane is therefore a way of increasing mixing and working time before gelation. Additionally, lower-functionality 3-aminopropylalkoxysilanes, such as 3-aminopropyldiethoxymethylsilane and even 3-(ethoxydimethylsilyl)propylamine, effectively crosslinked polyvinylalcohol acetoacetate.

This example demonstrates the ability of aqueous mixtures of polyvinylalcohol acetoacetate and 3-aminopropyltrimethoxysilane to react quickly to form hydrogels, which could function as bioadhesives.

Example 18

Sorbitol Acetoacetate-Polyamine Hydrogels

Sorbitol acetoacetate of Example 6 (eq wt=130; 0.8 g) was taken up in 2.4 g of water and the hazy solution was clarified by syringe filtration. This solution, about 20 wt % solids, was used for the following hydrogelation reactions:

17-A. Equal volumes (about 50 μL) of a 10 wt % solution of aqueous polyallylamine (100% free NH$_2$; eq wt=57) and sorbitol acetoacetate solution were mixed on a microscope slide. The mixture solidified in 15 sec to a stiff hydrogel.

17-B. Equal volumes (about 50 μL) of a 25 wt % aqueous solution of polyethyleneimine 2000 (eq wt=160) and sorbitol acetoacetate solution were mixed on a microscope slide. The mixture solidified in 1.5 min to a stiff hydrogel.

17-C. Equal volumes (about 50 μL) of a 25 wt % aqueous solution of polyethyleneimine 10000 (eq wt=170) and sorbitol acetoacetate solution were mixed on a microscope slide. The mixture solidified in 30 sec to a stiff hydrogel.

17-D. 100 μL of a 35 wt % solution of an 8-arm star PEG amine (from Shearwater Polymers, now Nektar Transforming Therapeutics; Mn=10,000 Da; NH$_2$ eq wt=1250 Daltons) and 20 μL sorbitol acetoacetate solution were mixed on a microscope slide. The mixture gelled over an hour to a soft, rubbery hydrogel.

This example demonstrates the ability of aqueous mixtures of sorbitol acetoacetate and various polyamines to react quickly to form hydrogels which could function as bioadhesives.

Example 19

Star PEG Acetoacetate-Polyamine Hydrogels

Star PEG acetoacetate of Example 8 (eq wt=2500; 0.2 g) was taken up in 0.6 g of water. This solution, about 25 wt % solids, was used for the following hydrogelation reactions:

18-A. A mixture of 10 μL of a 10 wt % solution of aqueous polyallylamine (Mw=15000 Da; 100% free NH$_2$; eq wt=57) and 30 μL (acac:NH$_2$~1:6) star PEG acetoacetate solution was stirred on a microscope slide. The mixture solidified in 3 min to a soft, rubbery hydrogel.

18-B. A mixture of 3 μL neat 3-aminopropyltrimethoxysilane (APS; Mw=179 Da) and 50 μL (acac:NH$_2$~1:3) star PEG acetoacetate solution was stirred on a microscope slide. The mechanism of hydrogelation with APS involves initial attack of the amino group on the PEG acac group; once the stabilization due to the free amino group is gone, the trimethoxysilane group quickly hydrolyzes to form siloxane crosslinks. The mixture solidified in 6 min to a soft, rubbery hydrogel, which could be taken off the slide with a razor blade and stretched 50%.

This example demonstrates the ability of aqueous mixtures of 4-arm star PEG acetoacetate and crosslinking amines to react quickly to form hydrogels, which could function as bioadhesives.

Example 20

Pentaerythritol Ethoxylate Acetoacetate-Polyamine Hydrogels

A 25 wt % solution of pentaerythritol ethoxylate acetoacetate (PEEO acac) of Example 7 was made up in water. This solution was reacted with equimolar quantities (acac:NH$_2$=1) of various polyamines in aqueous solution and the gel times were determined. These results are shown in Table 12.

TABLE 12

Gelation of PEEO acac with Various Amines

| Exp # | Aqueous Amine | μL PEEO acac | μL Amine | Gel time |
|---|---|---|---|---|
| 1 | 10 wt % Polyallylamine (Mw = 15 kDa; 100% free NH$_2$) | 100 | 50 | 55 sec |
| 2 | 25 wt % Polyethyleneimine 600 | 100 | 50 | 5.25 min |
| 3 | neat 3-Aminopropyltrimethoxysilane | 100 | 16 | 1.75 min |
| 4 | 30 wt % 8-Arm Star PEG 10K amine (Shearwater Polymers) | 50 | 180 | 48 min |

This example demonstrates the ability of aqueous mixtures of pentaerythritol ethoxylate acetoacetate and crosslinking amines to react quickly to form hydrogels, which could function as bioadhesives.

Example 21

Amino-Terminated Polyethyleneoxide-Polypropyleneoxide Acetoacetamide (XTJ-502 acac)-Polyallylamine Hydrogels A 25 wt % solution of XTJ-502 acac of Example 9 was made up in water. This solution was reacted with polyallylamine in aqueous solution and the gel times were determined.

20-A. Twenty microliters of 25 wt % aqueous XTJ-502 acac was combined with 20 µL of 25 wt % polyallylamine (Mw=15 kDa; 44% free $NH_2$). The mixture formed a hydrogel in about a minute.

20-B. Twenty microliters of 25 wt % aqueous XTJ-502 acac was combined with 10 µL of 25 wt % polyallylamine (Mw=15 kDa; 44% free $NH_2$). The mixture became a stiff gel in about 3 min.

This example demonstrates the ability of aqueous mixtures of polyether bis(acetoacetamide) and polyallylamine to react quickly to form hydrogels which could function as bioadhesives.

Example 22

Sealing an Incision in an Ex Vivo Swine Uterine Horn Using a Polyvinylalcohol Acetoacetate Hydrogel The efficacy of polyvinylalcohol acetoacetate hydrogels as a bioadhesive was demonstrated by sealing an incision in a section of swine uterine horn against hydrostatic pressure. The experiments were run in triplicate. The results are shown in Table 13.

Aqueous Solutions:
- 20 wt % PVOH acac (Mw=31-50 kDa; 10.4 mol % acac; eq wt=510)
- 20 wt % PEI 600 (polyethyleneimine Mn=600 Da, Aldrich #40, 871-9; eq wt~150)
- 20 wt % PVOH amine: polyvinylalcohol 4-aminobutyral acetal made according to Example 11 (Mw=31-50 kDa; eq wt=630)
- Neat APS: 3-aminopropyltrimethoxysilane (Aldrich #28, 177-8; mw=179.3 Da; D=1.016)
- 15 wt % PVOH-VNH2: poly(vinylalcohol-co-vinylamine) made according to Example 12 (eq wt=520)
- 20 wt % dextran aldehyde (Mw=10,000 Da; 48% conversion of saccharide rings to dialdehydes by periodate oxidation of dextran according to method of WO 03/35122)

Sealing an Incision in a Swine Uterine Horn:

An approximately 7.5 cm section of clean, fresh swine uterine horn, obtained from a local abattoir, was fitted on one end with a metal nozzle with a feed line from a syringe pump and was clamped on the other end with a hemostat; the nozzle was held in place with a nylon tie. A puncture cut was made in the center of the intestine section using a #11 scalpel, which gave an approximately 3 mm cut. Adhesive solution was applied over the puncture from a cut-off 3 mL syringe in the following manner. The Luer end of a 3 mL disposable syringe was cut off, the plunger was lowered about 2.5 cm and the PVOH acac and amine solutions were introduced into the barrel and stirred vigorously with a thin spatula for 10-15 sec or until the mixture began to thicken. The viscous fluid mixture was then delivered onto the tissue surface by pushing out with the plunger and quickly spreading with the spatula. This method allowed the application of two reactants in any volume ratio. If a 1:1 volume ratio of reactants was acceptable, a 2-barrel syringe with a static mixer tip could be used. Such syringe mixers are available from MixPac Systems AG, Rotkreuz, Switzerland. Care had to be taken to deliver the liquid when it had sufficiently thickened to avoid a run off but the onset of gelation had not yet occurred such that it would spread over the tissue and adhere to form a smooth, even patch. The adhesive patch was allowed to cure at RT for 3-5 min before testing. Subsequently, the sealed intestine was immersed in a dish of water and was pressurized with dyed water from a syringe pump (Model No. 22, Harvard Apparatus, Holliston, Mass.) at a rate of about 0.1 psig/3 sec until the bioadhesive seal began to visibly leak dyed water; at which time the leakage pressure was recorded. Alternatively, the intestine section was held in the air and pressurized with water until water began to drip from the site. This alternative procedure was used in Experiment #18.

In half of the experiments, the damp tissue surface was first "primed" by swabbing the area with a cotton Q-tip wet with 20 wt % dextran aldehyde solution. The dextran aldehyde was made by periodate oxidation of dextran according to the method of WO 03/35122.

TABLE 13

Sealing an Incision in a Swine Uterine Horn with PVOH acac Hydrogel

| Exp # | PVOH acac µL | Amine | Amine µL | acac:$NH_2$ | Dextran aldehyde primer? | Leak psig (n = 3) |
|---|---|---|---|---|---|---|
| 1 | 200 | PEI 600 | 20 | 3:1 | no | 1.67 ± 1.15 |
| 2 | 200 | PEI 600 | 20 | 3:1 | yes | 1.47 ± 0.63 |
| 3 | 200 | PEI 600 | 24 | 2.5:1 | no | 1.00 ± 0.87 |
| 4 | 200 | PEI 600 | 24 | 2.5:1 | yes | 1.37 ± 0.29 |
| 5 | 200 | PEI 600 | 30 | 2:1 | no | 1.83 ± 0.68 |
| 6 | 200 | PEI 600 | 30 | 2:1 | yes | 1.93 ± 0.65 |
| 7 | 200 | PEI 600 | 40 | 1.5:1 | no | 1.27 ± 0.55 |
| 8 | 200 | PEI 600 | 40 | 1.5:1 | yes | 2.13 ± 0.60 |
| 9 | 200 | PEI 600 | 60 | 1:1 | no | 1.70 ± 0.79 |
| 10 | 200 | PEI 600 | 60 | 1:1 | yes | 2.20 ± 0.62 |
| 11 | 200 | PVOH amine | 100 | 2.5:1 | no | 0.53 ± 0.12 |
| 12 | 200 | PVOH amine | 100 | 2.5:1 | yes | 1.17 ± 0.91 |
| 13 | 200 | PVOH amine | 150 | 1.7:1 | no | 0.63 ± 0.35 |
| 14 | 200 | APS | 6 | 2.4:1 | no | 0.13 ± 0.15 |

TABLE 13-continued

Sealing an Incision in a Swine Uterine Horn with PVOH acac Hydrogel

| Exp # | PVOH acac μL | Amine | Amine μL | acac:NH$_2$ | Dextran aldehyde primer? | Leak psig (n = 3) |
|---|---|---|---|---|---|---|
| 15 | 200 | APS | 6 | 2.4:1 | yes | 1.90 ± 0.53 |
| 16 | 200 | PVOH amine + APS | 100 + 3 | 1.6:1 | no | 1.43 ± 0.23 |
| 17 | 200 | PVOH amine + APS | 50 + 6 | 1.6:1 | no | 1.57 ± 0.15 |
| 18 | 600 | PVOH-VNH2 | 600 | 1:1 | no | 1.23 ± 0.06 |

1 psi = 6.895 kPa

This example demonstrates the ability of aqueous mixtures of various stoichiometry of polyvinylalcohol acetoacetate and various crosslinking amines to react quickly to form hydrogels, which function as bioadhesives. This example also illustrates the improvement in hydrogel adhesion to biological tissue brought about by "priming" the tissue surface with dextran aldehyde.

Example 23

Sealing a Sutured Incision in an Ex Vivo Swine Uterine Horn Using Polyvinylalcohol Acetoacetate-4,9-Dioxa-1,12-dodecanediamine (DODDA) Hydrogel The efficacy of polyvinylalcohol acetoacetate-DODDA hydrogel as a bioadhesive was demonstrated by sealing a sutured incision in a section of swine uterine horn against hydrostatic pressure. The results are shown in Table 14.
Aqueous Solutions:
  25 wt % PVOH acac (Mw=13-23 kDa; 5.2 mol % acac; eq wt=930)
  25 wt % PVOH acac (Mw=13-23 kDa; 11.4 mol % acac; eq wt=470)
  Neat 4,9-dioxa-1,12-dodecanediamine (Aldrich #22, 744-7; D=0.96; eq wt=102)
Sealing a Sutured Cut in a Swine Uterine Horn:
  A scalpel cut was made around one-half the circumference of an approximately 10 cm section of clean swine uterine horn; this cut was then closed with interrupted sutures using 5-0 Vicryl suture line (Ethicon Inc., Summerville, N.J.). The sutured intestine was fitted on one end with a metal nozzle with a feed line for water from a syringe pump and was clamped on the other end with a hemostat; the nozzle was held in place with a nylon tie. The suture line was blotted with a paper towel and then the adhesive was applied over the sutures using a spatula; the ingredients were premixed in a vial for the indicated time (25-50 sec) before application. After application the adhesive patch was allowed to cure at RT for 10 min. Then the sealed intestine was immersed in water and was pressurized with colored water from a syringe pump at a rate of about 0.1 psig/3 sec until the bioadhesive seal began to leak, at which point the pressure was recorded. The results are recorded in Table 14. Failure was adhesive rather than cohesive.

TABLE 14

Sealing an Incision in a Sutured Swine Uterine Horn with PVOH acac-DODDA Hydrogel

| Exp # | PVOH acac eq wt | PVOH acac | DODDA | Mix time | Cure time | Leak psig | Failure Mode |
|---|---|---|---|---|---|---|---|
| 1 | 930 | 0.4 mL | 15 μL | 50 sec | 10 min | 2.7 | Leak under adhesive |
| 2 | 470 | 0.5 mL | 20 μL | 25 sec | 10 min | 2.4 | Leak under adhesive |

1 psi = 6.895 kPa

This example demonstrates the ability of aqueous mixtures of polyvinylalcohol acetoacetate and 4,9-dioxa-1,12-dodecanediamine to react quickly to form hydrogels which function as bioadhesives.

Example 24

Sealing an Incision in an Ex Vivo Swine Uterine Horn Using a Combination of Polyvinylalcohol Acetoacetate and Polyallylamine (PAA)

The efficacy of polyvinylalcohol acetoacetate-polyallylamine (PAA) hydrogel as a bioadhesive was demonstrated by sealing an incision in a section of swine uterine horn against hydrostatic pressure. The results are shown in Table 15 below.
Aqueous Solutions:
  25 wt % PVOH acac (Mw=13-23 kDa; 5 mol % acetoacetate; eq wt=960)
  25 w/v % Polyallylamine (22 mol % NH$_2$): A solution of 2.0 g polyallylamine-HCl (Mn~15,000 Da; Aldrich #28, 321-5) was made up to 5.0 mL in water (4.28 M). A 1.0-mL aliquot was neutralized with 0.050 mL 50 wt % aqueous NaOH (Density=1.5; ~0.9 mmol NaOH) and 0.25 mL water was added to give a solution that was 0.7 M in NH$_2$ and 3.26 M in PAA (22 mol % free NH$_2$).
  25 w/v % Polyallylamine (44 mol % NH$_2$): A solution of 2.0 g polyallylamine-HCl was made up to 5.0 mL solution in water (4.28 M). A 2.0-mL aliquot (0.8 g PAA HCl; 8.6 mmol) was neutralized with 0.20 mL 50 wt % aqueous NaOH (Density=1.5; ~3.8 mmol NaOH) and 0.5 mL water was added to give a solution that was 1.38 M in NH$_2$ and 3.11 M in PAA (44 mol % free NH$_2$).
Sealing an Incision in a Swine Uterine Horn:
  The same technique was used to seal an incision in a swine uterine horn as was described in Example 22, with the following variation: because gelation was typically so fast (a few sec), equal volumes of the two solutions were quickly squirted together simultaneously with Eppendorf pipettes on and around the puncture (about a ~0.5-1 cm radius), followed by mixing with the ends of the pipette tips until gelation made mixing impossible. After application the adhesive patch was allowed to cure at RT for 2 min and then was hydrostatically pressure-tested as before.

TABLE 15

Sealing an Incision in a Swine Uterine Horn with PVOH acac-PAA Hydrogel

| Exp # | PVOH acac | PAA % $NH_2$ | PAA | Mix time | Cure time | Leak psig | Failure Mode |
|---|---|---|---|---|---|---|---|
| 1 | 0.05 mL | 22 | 0.05 mL | ~5 sec | 2 min | 1.9 | Leak through adhesive |
| 2 | 0.05 mL | 44 | 0.05 mL | ~5 sec | 2 min | 2.4 | Leak through adhesive |

1 psi = 6.895 kPa

Adhesion was very good in both cases. The failure was cohesive. This example demonstrates the ability of an aqueous mixture of polyvinylalcohol acetoacetate and polyallylamine to react quickly to form a hydrogel, which functions as a bioadhesive.

Example 25

Sealing a Sutured Incision in an Ex Vivo Swine Uterine Horn Using a Combination of Polyvinylalcohol Acetoacetate and Polyallylamine (PAA)

The efficacy of polyvinylalcohol acetoacetate-polyallylamine (PAA) hydrogel as a bioadhesive was demonstrated by sealing an incision in a section of swine uterine horn against hydrostatic pressure. In this case a mixing syringe was used to combine the reactants at the incision site. The results are shown in Table 16 below.
Aqueous Solutions:
  25 w/w % PVOH acac (Mw=13-23 kDa; 4.2 mol % acac; eq wt=1040)
  14 w/v % Polyallylamine (PAA; Mw=15 kDa; 21% $NH_2$; eq wt=410)
Sealing a Sutured Cut in a Swine Uterine Horn:
  A scalpel cut was made around one-half the circumference of an approximately 15 cm section of clean, fresh swine uterine horn; this cut was then closed with interrupted sutures using 5-0 Vicryl suture line. Two suture techniques were used: "outer", in which the only outer layer of tissue was drawn together (8-9 sutures) and "inner", in which just the inner layer of muscle was drawn together (6-7 sutures). The sutured intestine was fitted on one end with a metal nozzle with a feed line for water from a syringe pump and was clamped on the other end with a hemostat; the nozzle was held in place with a nylon tie. The suture line was dried by dabbing with a paper towel and then the adhesive was applied over the sutures using a simple two-syringe Y-mixer with a 20 gauge needle. Equal amounts (0.15-0.20 mL each) of each of the two component solutions (PVOH acac and polyallylamine) were used. The two solutions were coinjected slowly to allow some viscosity build in the syringe mixer so the solutions wouldn't run off the intestine; then the syringe needle was used to stir the applied bioadhesive mixture until it had become rather thick (~10 sec). After application the adhesive patch was allowed to cure at RT for 2 min. Then the sealed intestine was pressurized with water from the syringe at a rate of about 0.1 psig/3 sec until the bioadhesive seal began to leak water, at which point the pressure was recorded. Failures were typically cohesive; i.e., the water penetrated the hydrogel itself rather than leaked from under it. In several cases the intestinal tissue itself began to leak due to tearing before the adhesive failed.

TABLE 16

Sealing an Incision in a Swine Uterine Horn with PVOH acac-PAA Hydrogel

| Exp # | PVOH acac | PAA % $NH_2$ | PAA | Suture | Cure time | Leak psig | Failure Mode |
|---|---|---|---|---|---|---|---|
| 1 | 0.15 mL | 21 | 0.15 mL | outer | 2 min | 2.6 ± 0.6 (n = 8) | Leak through adhesive |
| 2 | 0.15 mL | 44 | 0.15 mL | inner | 2 min | 2.9 ± 0.9 (n = 3) | Leak through adhesive |

1 psi = 6.895 kPa

This example demonstrates the ability of an aqueous mixture of polyvinylalcohol acetoacetate and polyallylamine to form a hydrogel which functions as a bioadhesive.

Example 26

Sealing an Incision in an Ex Vivo Swine Uterine Horn Using a Combination of Branched Polyester Polyether Acetoacetate and Polyallylamine (PAA)

The efficacy of branched polyester polyether acetoacetate (Example 10)—polyallylamine (PAA) hydrogel as a bioadhesive was demonstrated by sealing an incision in a section of swine uterine horn against hydrostatic pressure. The results are shown in Table 17 below.
Aqueous Solutions:
  30 wt % Branched polyester PEG acac of Example 10 (eq wt=1670)
  40 wt % Polyallylamine: A solution of 2.0 g polyallylamine-HCl (Mw~15000 Da; Aldrich #28, 321-5) was made up to 5.0 mL solution in water (4.28 M). A 2.0-mL aliquot was neutralized with 0.20 mL 50% aqueous NaOH (Density=1.5; ~1.9 mmol NaOH) to give a solution that was 1.72 M in $NH_2$ and 3.89 M in PAA (44 mol % free $NH_2$).
Sealing an Incision in a Swine Uterine Horn:
  A 20 cm section of clean swine uterine horn was fitted on one end with a metal plug with a feed line fitting for water feed from a syringe pump and on the other end with a metal plug with a threaded hole which could be sealed with a machine screw; the plugs were held in place with nylon ties around the outside of the intestine. A cut was made in the center of the length of intestine through the intestine wall into the interior by puncturing with a #22 scalpel. The cut on the outside of the intestine was at least as wide as the scalpel blade (nearly a centimeter) while the hole through the inside wall was probably 2-3 millimeters.

The intestine was filled with water via the syringe pump until water began to leak from the open hole in the end plug and also from the scalpel puncture in the intestinal wall. The pump was then turned off and the end plug was sealed with the machine screw. The location of the scalpel cut was dried by dabbing with a paper towel.

The polyallylamine and branched polyester PEG acac solutions were mixed together in a vial for 15 seconds (by 30 seconds this mixture was too viscous to pipette) and then the mixture was spread over the intestinal incision and allowed to cure for 2 min. Testing was done by pressurizing the sealed intestine with water from the syringe pump at a rate of about 0.1 psi/2-3 sec until the bioadhesive seal began to leak, at which point the pressure was recorded.

TABLE 17

Sealing an Incision in a Swine Uterine Horn with Branched Polyester PEG acac-PAA Hydrogel

| Exp # | Branched Polyester PEG acac | PAA | Cure time | Leak psig | Failure Mode |
|---|---|---|---|---|---|
| 1 | 0.10 mL | 0.05 mL | 2 min | 1.84 | Leak through adhesive |
| 2 | 0.10 mL | 0.05 mL | 2 min | 1.90 | Leak through adhesive |

1 psi = 6.895 kPa

Adhesion was very good in both cases; failure was cohesive. This example demonstrates the ability of an aqueous mixture of a branched polyether polyol acetoacetate and polyallylamine to react quickly to form a hydrogel which functions as a bioadhesive.

Example 27

Sealing a Slit in Regenerated Collagen Sheet with Polyvinylalcohol Acetoacetate-Polyallylamine Adhesive The efficacy of polyvinylalcohol acetoacetate-polyallylamine (PAA) hydrogel as a bioadhesive was demonstrated by sealing a slit in a damp regenerated collagen sheet against hydrostatic pressure. The results are shown in Table 18 below.
Regenerated Collagen Sheet Substrate:
  Commercial collagen (collagen I) sausage casing (31-mm diameter; The Sausage Source, Hillsborough, N.H.) was slit lengthwise to give a 9 cm wide strip. The strip was degreased by soaking in 2 changes of methylene chloride over an hour. The strip was then soaked in isopropanol for 20 hr followed by washing four times with deionized water and finally soaked in deionized water for 6 hr. The skin was rolled up onto a glass tube and stored damp in the freezer in a sealed polyethylene bag.
Burst Tester:
  The burst tester consisted of a 25-mm steel in-line flat filter holder with a Luer fitting, in which was mounted a circle of damp collagen sheet. The circle had been cut out from a larger sheet of collagen using a 2.65 cm arc punch. After mounting the collagen circle in the filter, a 2-mm slit was punched in the center of the sheet with a sharpened spatula point.

The slit in the damp collagen sheet was sealed with a 2-component reactive adhesive in the following manner. The solutions were applied with Eppendorf pipettes. One of the solutions was placed to one side of the slit about 1 mm away and the other solution was applied about 1 mm away on the other side of the slit. The two solutions were then dragged together with a spatula and gently mixed on top of the slit as well as possible before gelation began (typically 10 sec or less). When the mixture had started to gain significant viscosity, mixing was stopped and the mixture was allowed to cure for 2 min.

The sealed collagen sheet was hydrostatically tested 2 min after mixing. The sample was pressurized with water by means of a syringe pump at a rate of about 0.1 psig/sec until the seal leaked. The sample/filter holder assembly was oriented face down to make sure the collagen was always being pressurized with water rather than an air bubble. The system pressure at failure was determined with an Omega recording pressure gauge. Failure mode was judged to be adhesive if the leak appeared to be coming from under the gel, between the intact gel mass and collagen membrane. Cohesive failure was attributed when the leak appeared to break through the gel mass. Two or 3 trials were run of each composition.
Aqueous Solutions:
  25 wt % Polyvinylalcohol acetoacetate (Mw=13-23 kDa; 5.9 mol % acac; eq wt=830)
  15 wt % Polyallylamine (Mw=15 kDa; 21% $NH_2$; eq wt=410)
  10 wt % Polyallylamine (Mw=15 kDa; 21% $NH_2$; eq wt=410)
  15 wt % Polyallylamine (Mw=15 kDa; 60% $NH_2$; eq wt=120)
  10 wt % Polyallylamine (Mw=15 kDa; 60% $NH_2$; eq wt=120)
  5 wt % Polyallylamine (Mw=15 kDa; 60% $NH_2$; eq wt=120)
  10 wt % Polyallylamine (Mw=15 kDa; 100% $NH_2$; eq wt=57)
  5 wt % Polyallylamine (Mw=15 kDa; 100% $NH_2$; eq wt=57)

TABLE 18

Sealing a Slit in Collagen with PVOH acac-PAA Hydrogel

| Exp # | PVOH acac | PAA | PAA % $NH_2$ | PAA wt % | acac:$NH_2$ | PVOH:PAA | Burst, psig (n = 2, 3) | High, psig |
|---|---|---|---|---|---|---|---|---|
| 1 | 40 µL | 20 µL | 21 | 15 | 1.64 | 1:0.3 | 2.3 ± 0.7 | 2.8 |
| 2 | 30 µL | 30 µL | 21 | 10 | 1.23 | 1:0.4 | 2.1 ± 0.3 | 2.3 |
| 3 | 30 µL | 30 µL | 21 | 15 | 0.83 | 1:0.6 | 3.3 ± 0.7 | 3.9 |
| 4 | 30 µL | 30 µL | 60 | 5 | 0.72 | 1:0.2 | 1.9 ± 1.3 | 2.9 |
| 5 | 40 µL | 20 µL | 60 | 10 | 0.72 | 1:0.2 | 1.8 ± 0.9 | 2.5 |
| 6 | 30 µL | 20 µL | 60 | 10 | 0.54 | 1:0.3 | 1.8 ± 1.5 | 3.5 |

TABLE 18-continued

Sealing a Slit in Collagen with PVOH acac-PAA Hydrogel

| Exp # | PVOH acac | PAA | PAA % NH2 | PAA wt % | acac:NH$_2$ | PVOH:PAA | Burst, psig (n = 2, 3) | High, psig |
|---|---|---|---|---|---|---|---|---|
| 7 | 40 μL | 20 μL | 60 | 15 | 0.48 | 1:0.3 | 2.9 ± 2.2 | 4.4 |
| 8 | 30 μL | 30 μL | 60 | 10 | 0.36 | 1:0.4 | 2.9 ± 0.9 | 3.5 |
| 9 | 20 μL | 40 μL | 60 | 5 | 0.36 | 1:0.4 | 2.4 ± 0.7 | 3.0 |
| 10 | 30 μL | 30 μL | 60 | 10 | 0.36 | 1:0.4 | 1.5 ± 1.1 | 2.6 |
| 11 | 30 μL | 30 μL | 100 | 5 | 0.34 | 1:0.2 | 1.5 ± 0.2 | 1.7 |
| 12 | 40 μL | 20 μL | 100 | 10 | 0.34 | 1:0.2 | 2.1 ± 0.6 | 2.8 |
| 13 | 30 μL | 20 μL | 100 | 10 | 0.26 | 1:0.3 | 1.8 ± 0.7 | 2.6 |
| 14 | 30 μL | 30 μL | 60 | 15 | 0.24 | 1:0.6 | 1.8 ± 0.6 | 2.2 |
| 15 | 20 μL | 40 μL | 100 | 5 | 0.17 | 1:0.4 | 1.7 ± 0.5 | 2.2 |
| 16 | 30 μL | 30 μL | 100 | 10 | 0.17 | 1:0.4 | 2.7 ± 0.8 | 3.6 |

1 psi = 6.895 kPa

The tests were mostly run in triplicate; the results are arranged in order of increasing amine:acac ratio. Failure mode was generally cohesive: water burst through the gel mass rather than leaked under it. The low values tended to be adhesive failures while the high values were cohesive failures. This example demonstrates the ability of aqueous mixtures of various stoichiometry of polyvinylalcohol acetoacetate and polyallylamine to react quickly to form hydrogels which function as bioadhesives.

Example 28

Lap Shear Tensile Bond Strength of Polyvinylalcohol Acetoacetate-Polyallylamine (PAA) Adhesive on Regenerated Collagen Sheet The efficacy of polyvinylalcohol acetoacetate-polyallylamine (PAA) hydrogel as a bioadhesive was demonstrated by bonding together two damp strips of regenerated collagen sheet and testing the tensile lap shear strength of the bond. The results are shown in Table 19 below.

Gluing Technique:

The collagen sheet substrate is described in Example 27. The damp collagen sheet was laid on top of a polyethylene sheet which had been premarked in 1 cm-wide stripes with a marking pen. The collagen-polyethylene laminate was then cut along the marked lines with scissors to give 1-cm wide× 9-cm long collagen test strips which were kept adhered by capillary action to their polyethylene backing for handling. The collagen was always maintained damp during adhesive application, curing and testing. First, two collagen strips were laid side by side, polyethylene down, and the mating surface areas of the wet strips (a 1-cm square area at one end of each strip) were quickly and lightly dabbed with a paper tissue to remove gross water droplets. Then 5 μL of each of the two adhesive component solutions were dispensed via Eppendorf pipettes onto one strip and quickly mixed on the surface with a spatula for 2-3 sec. Then the end of the other collagen strip was quickly overlapped 1 cm and lightly pressed onto the first adhesive-painted surface to make an approximately 1-cm$^2$ lap joint. The bonded collagen strips were kept moist between damp paper towels for 5 min and then the polyethylene backing was removed and the sample was tensile-tested.

Tensile Testing:

A Com-Ten Industries 95 VD tensile tester (Com-Ten Industries, Pinellis Park, Fla.) with a 100-lb load cell was used for tensile testing. The sample clamps were lined with thin copper sheet to avoid tearing the collagen substrate. The samples were loaded damp and tested immediately to avoid drying out. Each sample was pulled to failure at a rate of 1.0 cm/min (0.4 inch per min). The results are summarized in Table 19 (1 psi=70.4 g/cm$^2$).

Aqueous Solutions:

25 wt % Polyvinylalcohol acetoacetate (Mw=13-23 kDa; 4.4 mol % acac; eq wt==1085)

33 wt % Polyvinylalcohol acetoacetate (Mw=13-23 kDa; 4.4 mol % acac; eq wt==1085)

15 wt % Polyallylamine (Mw=15 kDa; 21% NH$_2$; eq wt=410)

10 wt % Polyallylamine (Mw=15 kDa; 21% NH$_2$; eq wt=410)

15 wt % Polyallylamine (Mw=15 kDa; 60% NH$_2$; eq wt=120)

10 wt % Polyallylamine (Mw=15 kDa; 60% NH$_2$; eq wt=120)

15 wt % Polyallylamine (Mw=15 kDa; 100% NH$_2$; eq wt=57)

10 wt % Polyallylamine (Mw=15 kDa; 100% NH$_2$; eq wt=57)

TABLE 19

PVOH acac-PAA Lap Shear Tensile Test on Collagen

| Exp # | PVOH acac | PVOH wt % | PAA | PAA % NH$_2$ | PAA wt % | acac:NH$_2$ | PVOH:PAA | Tensile, g/cm$^2$ (n = 3) |
|---|---|---|---|---|---|---|---|---|
| 1 | 5 μL | 33 | 5 μL | 21 | 10 | 1.39 | 1:0.27 | 168 ± 26 |
| 2 | 5 μL | 25 | 5 μL | 21 | 10 | 1.05 | 1:0.36 | 171 ± 76 |
| 3 | 5 μL | 33 | 5 μL | 21 | 15 | 0.88 | 1:0.42 | 180 ± 41 |
| 4 | 5 μL | 25 | 5 μL | 21 | 15 | 0.68 | 1:0.56 | 179 ± 10 |
| 5 | 5 μL | 33 | 5 μL | 60 | 10 | 0.40 | 1:0.27 | 143 ± 29 |
| 6 | 5 μL | 25 | 5 μL | 60 | 10 | 0.31 | 1:0.36 | 170 ± 98 |
| 7 | 5 μL | 33 | 5 μL | 60 | 15 | 0.26 | 1:0.42 | 67 ± 8 |

TABLE 19-continued

PVOH acac-PAA Lap Shear Tensile Test on Collagen

| Exp # | PVOH acac | PVOH wt % | PAA | PAA % NH$_2$ | PAA wt % | acac:NH$_2$ | PVOH:PAA | Tensile, g/cm$^2$ (n = 3) |
|---|---|---|---|---|---|---|---|---|
| 8 | 5 μL | 25 | 5 μL | 60 | 15 | 0.20 | 1:0.56 | 147 ± 27 |
| 9 | 5 μL | 33 | 5 μL | 100 | 10 | 0.19 | 1:0.27 | 127 ± 44 |
| 10 | 5 μL | 25 | 5 μL | 100 | 10 | 0.15 | 1:0.36 | 131 ± 61 |
| 11 | 5 μL | 33 | 5 μL | 100 | 15 | 0.12 | 1:0.42 | 262 ± 108 |
| 12 | 5 μL | 25 | 5 μL | 100 | 15 | 0.09 | 1:0.56 | 274 ± 100 |

The tests were run in triplicate; the results are arranged in order of decreasing acac:amine ratio. The best results were at high solids and high amine level. This example demonstrates the ability of aqueous mixtures of various stoichiometry of polyvinylalcohol acetoacetate and polyallylamine to react quickly to form hydrogels which function as bioadhesives.

Example 29

Lap Shear Tensile Bond Strength of Dextran Acetoacetate-Polyallylamine Adhesive on Regenerated Collagen Sheet A 2-component bioadhesive made from dextran acetoacetate and polyallylamine (PAA) of various degrees of neutralization was used to bond collagen strips as described in Example 28. The results are shown in Table 20.

Aqueous Solutions:
25 wt % Dextran 40K acac (Mw=40 kDa; 26 mol % acac; eq wt=710)
25 wt % Dextran 40K acac (Mw=40 kDa; 11 mol % acac; eq wt=1550)
10 wt % Polyallylamine (Mw=15 kDa; 20% NH$_2$; eq wt=410)
10 wt % Polyallylamine (Mw=15 kDa; 60% NH$_2$; eq wt=120)
10 wt % Polyallylamine (Mw=15 kDa; 100% NH$_2$; eq wt=57)

TABLE 20

Dextran acac-PAA Lap Shear Tensile Test on Collagen

| Exp # | Dextran acac | Dextran eq wt | PAA | PAA % NH$_2$ | acac:NH$_2$ | Trial #1 Tensile, g/cm$^2$ | Trial #2 Tensile, g/cm$^2$ |
|---|---|---|---|---|---|---|---|
| 1 | 10 μL | 710 | 10 μL | 20 | 1.43 | <50 | 109 |
| 2 | 10 μL | 710 | 10 μL | 60 | 0.42 | <50 | 171 |
| 3 | 10 μL | 710 | 10 μL | 100 | 0.20 | 197 | 81 |
| 4 | 10 μL | 1550 | 10 μL | 20 | 0.67 | 197 | 123 |
| 5 | 10 μL | 1550 | 10 μL | 60 | 0.20 | 95 | 86 |
| 6 | 10 μL | 1550 | 10 μL | 100 | 0.09 | 184 | 149 |

This example demonstrates the ability of aqueous mixtures of various stoichiometry of dextran acetoacetate and polyallylamine to react quickly to form hydrogels which function as bioadhesives.

Example 30

Lap Shear Tensile Bond Strength of Polyvinylalcohol Acetoacetate-Polyethyleneimine on Regenerated Collagen Sheet Damp regenerated collagen strips were bonded together with polyvinylalcohol acetoacetate and polyethyleneimine (PEI) and the lap shear tensile strength was determined as in Example 28. A 1-cm$^2$ area at the end of a 1 cm-wide×9 cm-long strip of damp collagen sheet was painted using quantities of each of the PVOH acac and PEI solutions indicated in Table 21 below. The solutions were mixed with a small spatula for 15 sec before overlapping a second collagen strip 1 cm at the end, lightly pressing and squirming the joint to establish a bond. The bonded collagen strips were kept moist between damp paper towels for 5 min and then tensile tested at 1.0 cm/min (0.4 inch per min). The results are summarized in Table 21 (1 psi=70.4 g/cm$^2$).

Aqueous Solutions:
25 w/w % Polyvinylalcohol acetoacetate (Mw=13-23 kDa; 4.4 mol % acac; eq wt=1085)
25 wt % PEI 600 (Aldrich #40,871-9; Mn=600 Da; NH$_2$ eq wt~150)
33 wt % PEI 600 (Aldrich #40,871-9; Mn=600 Da; NH$_2$ eq wt~150)
25 wt % PEI 2000 (Aldrich #40,870-0; Mn=2000 Da; NH$_2$ eq wt~160)
33 wt % PEI 2000 (Aldrich #40,870-0; Mn=2000 Da; NH$_2$ eq wt~160)

TABLE 21

PVOH acac-Polyethyleneimine Lap Shear Tensile Test on Collagen

| Exp # | PVOH acac | PEI | PEI Mw Da | PEI wt % | acac:NH$_2$ | PVOH:PAA | Tensile, g/cm$^2$ (n = 3) |
|---|---|---|---|---|---|---|---|
| 1 | 15 μL | 4 μL | 2000 | 25 | 0.55 | 1:0.27 | 325 ± 12 |
| 2 | 15 μL | 4 μL | 600 | 25 | 0.52 | 1:0.27 | 341 ± 66 |
| 3 | 15 μL | 5 μL | 2000 | 25 | 0.44 | 1:0.33 | 333 ± 14 |
| 4 | 15 μL | 5 μL | 600 | 25 | 0.41 | 1:0.33 | 252 ± 51 |
| 5 | 10 μL | 5 μL | 2000 | 25 | 0.29 | 1:0.50 | 302 ± 13 |
| 6 | 10 μL | 5 μL | 600 | 25 | 0.28 | 1:0.50 | 299 ± 39 |
| 7 | 15 μL | 4 μL | 2000 | 33 | 0.42 | 1:0.35 | 280 ± 18 |

TABLE 21-continued

PVOH acac-Polyethyleneimine Lap Shear Tensile Test on Collagen

| Exp # | PVOH acac | PEI | PEI Mw Da | PEI wt % | acac:NH$_2$ | PVOH:PAA | Tensile, g/cm$^2$ (n = 3) |
|---|---|---|---|---|---|---|---|
| 8  | 15 μL | 4 μL | 600  | 33 | 0.39 | 1:0.35 | 200 ± 33 |
| 9  | 15 μL | 5 μL | 2000 | 33 | 0.34 | 1:0.44 | 262 ± 38 |
| 10 | 15 μL | 5 μL | 600  | 33 | 0.31 | 1:0.44 | 255 ± 31 |
| 11 | 10 μL | 5 μL | 2000 | 33 | 0.22 | 1:0.66 | 211 ± 83 |
| 12 | 10 μL | 5 μL | 600  | 33 | 0.21 | 1:0.66 | 141 ± 54 |

Results are arranged in order of decreasing acac:amine ratio for the two different concentrations of PEI; examples 1-6 used 25 wt % PEI while examples 7-12 used 33 wt % PEI. In about one-third of the experiments, the collagen strip broke before the lap bond. This example demonstrates the ability of aqueous mixtures of various stoichiometry of polyvinylalcohol acetoacetate and polyethyleneimine to react quickly to form hydrogels which function as bioadhesives.

Example 31

Lap Shear Tensile Bond Strength of Polyvinylalcohol Acetoacetate-Polylysine on Regenerated Collagen Sheet

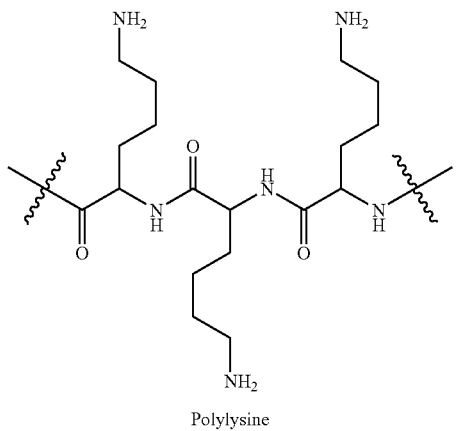 [SMILES: *NC(CCCCN)C(=O)NC(CCCCN)C(=O)NC(CCCCN)C(*)=O]

Polylysine

Damp regenerated collagen strips were bonded together with polyvinylalcohol acetoacetate-polylysine and the lap shear tensile strength was determined as in Example 28. A 1-cm$^2$ area at the end of a 1 cm-wide×9 cm-long strip of damp collagen sheet was painted using quantities of each of the polyvinylalcohol acetoacetate and polylysine solutions indicated in Table 22 below. The solutions were mixed well with a small spatula for 15 sec before overlapping a second collagen strip 1 cm at the end, lightly pressing and squirming the joint to establish a bond. The bonded collagen strips were kept moist between damp paper towels for 5 min and then tensile tested at 1.0 cm/min (0.4 inch per min). The results are summarized in Table 22 (1 psi=70.4 g/cm$^2$).

Aqueous Solutions:

Polylysine solution: A 25 wt % solution of polylysine hydrobromide (100 mg=61 mg free polylysine; Sigma P-9011; lot 40K51321; Mw=50,000-60,000 Da; repeat unit mw: 209.08 Da; 0.48 mmol lysine HBr units) was made up by adding 0.30 mL water to a 100-mg bottle of polylysine HBr and magnetically stirring in the capped bottle with a flea stir bar for 10 min. This solution is about 1.2 M in lysine units (lysine repeat unit mw: 128.17 Da) and contains ~17 wt % polylysine. To this polylysine HBr solution was added 25 μL of 50 wt % aq NaOH solution (Density=1.5; ~0.47 mmol NaOH; 98% neutralization; 1.1 M NH$_2$). The solution became a gel, so 25 μL (0.10 mmol) of 4M HCl in dioxane was added and the mixture was stirred and warmed on a hot plate for 10 min; the mixture remained a gel. Another 25 μL of 4M HCl/dioxane was added and the mixture was stirred at RT for 30 min; it was now a softer gel. Finally 50 μL of deionized water was added and the mixture was stirred for 30 min more, producing a clear solution which contains about 13 wt % free polylysine and which has about 60% free NH$_2$ (about 0.8 M NH$_2$) and 40% amine HCl salt (NH$_2$ eq wt=240).

25 w/w % Polyvinylalcohol acetoacetate (Mw=13-23 kDa; 4.4 mol % acac; eq wt=1085)

33 w/w % Polyvinylalcohol acetoacetate (Mw=13-23 kDa; 4.4 mol % acac; eq wt=1085)

13 wt % Polylysine (Mw=50-60 kDa; 60% free NH$_2$; eq wt=240)

TABLE 22

PVOH acac-Polylysine Lap Shear Tensile Test on Collagen

| Exp # | PVOH acac | PVOH acac wt % | Polylysine | acac:NH$_2$ | PVOH:pLysine | Tensile, g/cm$^2$ (high) |
|---|---|---|---|---|---|---|
| 1 | 10 μL | 33 | 5 μL  | 1.11 | 1:0.2 | 181 |
| 2 | 10 μL | 25 | 5 μL  | 0.83 | 1:0.3 | 0   |
| 3 | 8 μL  | 33 | 8 μL  | 0.56 | 1:0.4 | 171 |
| 4 | 8 μL  | 25 | 8 μL  | 0.42 | 1:0.5 | 83  |
| 5 | 5 μL  | 33 | 10 μL | 0.28 | 1:0.9 | 433 |
| 6 | 5 μL  | 25 | 10 μL | 0.21 | 1:1.0 | 256 |

The tests were run in triplicate and the results are arranged in order of decreasing acac:amine ratio. The highest value is reported for each condition. This example demonstrates the ability of aqueous mixtures of various stoichiometry of polyvinylalcohol acetoacetate and polylysine to react quickly to form hydrogels which function as bioadhesives.

Example 32

Lap Shear Tensile Bond Strength of Polyvinylalcohol Acetoacetate-Polyamidoamine PAMAM Starburst® Dendrimer on Regenerated Collagen Sheet Collagen strips were bonded together with PVOH acac-PAMAM Starburst® Dendrimer and the lap shear tensile strength was determined. A 1-cm² area at the end of a 1 cm-wide×9 cm-long strip of damp collagen sheet was painted using quantities of each of the polyvinylalcohol acetoacetate and PAMAM solutions indicated in Table 23 below. The solutions were mixed well for 15 sec before overlapping a second collagen strip 1 cm at the end, lightly pressing and squirming the joint to establish a bond. The bonded collagen strips were kept moist between damp paper towels for 5 min and then tensile tested at 1.0 cm/min (0.4 inch per min). The results are summarized in Table 23 (1 psi=70.4 g/cm²).

Aqueous Solutions:

25 w/w % Polyvinylalcohol acetoacetate (Mw=13-23 kDa; 4.4 mol % acac; eq wt=1085)

33 w/w % Polyvinylalcohol acetoacetate (Mw=13-23 kDa; 4.4 mol % acac; eq wt=1085)

20 wt % Gen 1 PAMAM: A 2.00-g aliquot of a 20 wt % solution of PAMAM Starburst® Generation 1 Dendrimer (Aldrich #41,238-4; Mn=1430 Da; 8 NH$_2$ groups per molecule; NH$_2$ eq wt=180) in methanol was placed in a rotoevaporator and then held under high vacuum for 48 hr to remove solvent. The concentrate was taken up in 1.60 g water to give a 20 wt % solution.

20 wt % Gen 4 PAMAM: A 2.00-g aliquot of a 10 wt % solution of PAMAM Starburst® Generation 4 Dendrimer (Aldrich #41,244-9; Mn=14215 Da; 64 NH$_2$ groups per molecule; NH$_2$ eq wt=222) in methanol was placed in a rotoevaporator and then held under high vacuum for 48 hr. The concentrate was taken up in 0.80 g water to give a 20 wt % solution.

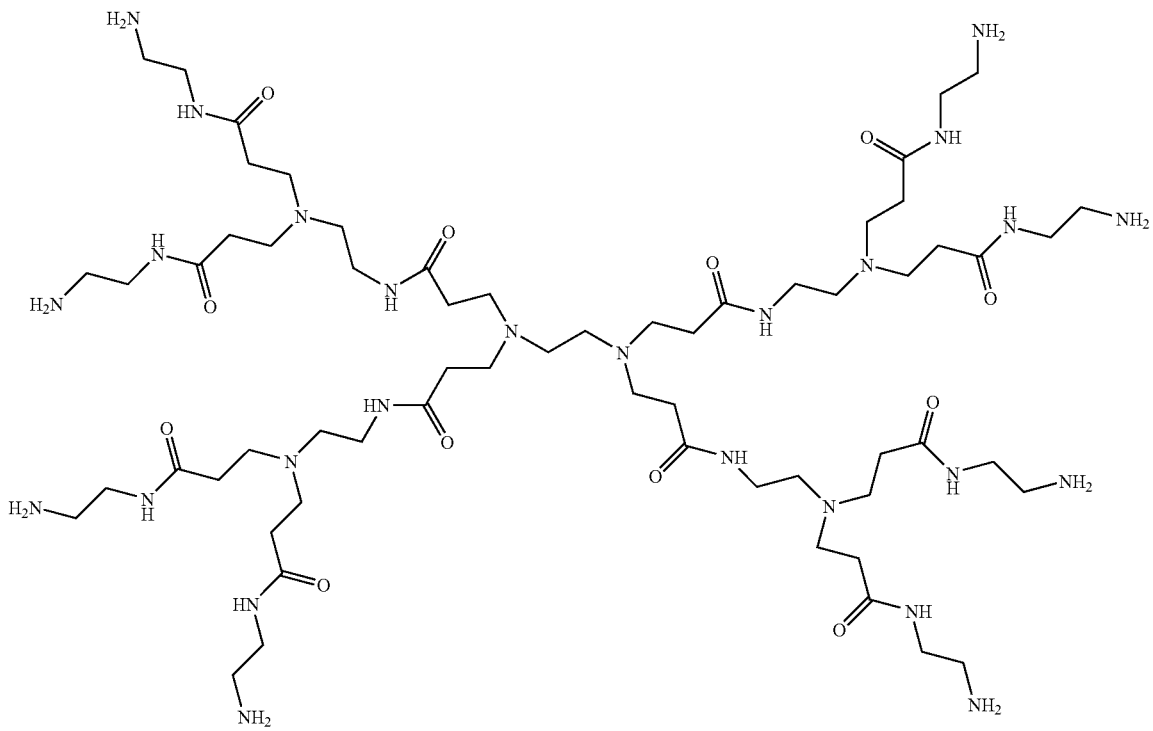

Gen 1 PAMAM Starburst™ Dendrimer

TABLE 23

| | | | | | | Tensile, |
| | PVOH | PVOH | | PAMAM | | g/cm² |
| Exp # | acac | acac wt % | PAMAM | Gen | acac:NH₂ | PVOH:PAMAM | (high) |
|---|---|---|---|---|---|---|---|
| 1 | 5 µL | 33 | 5 µL | 1 | 0.27 | 1:0.61 | 379 |
| 2 | 5 µL | 33 | 10 µL | 1 | 0.14 | 1:1.21 | 120 |
| 3 | 10 µL | 33 | 5 µL | 4 | 0.68 | 1:0.30 | 285 |
| 4 | 10 µL | 25 | 5 µL | 4 | 0.52 | 1:0.40 | 181 |
| 5 | 5 µL | 33 | 5 µL | 4 | 0.34 | 1:0.61 | 271 |
| 6 | 5 µL | 25 | 5 µL | 4 | 0.26 | 1:0.80 | 83 |
| 7 | 5 µL | 33 | 10 µL | 4 | 0.17 | 1:1.21 | 271 |
| 8 | 5 µL | 25 | 10 µL | 4 | 0.13 | 1:1.60 | 253 |

The experiments were run in triplicate and the results are arranged in order of decreasing acac:amine ratio for the two PAMAM samples; the high value is reported in each case. Experiments 1 and 2 were run with Gen 1 PAMAM while experiments 3-8 were run with Gen 4 PAMAM. This example demonstrates the ability of aqueous mixtures of various stoichiometry of polyvinylalcohol acetoacetate and dendrimeric polyamidoamine to react quickly to form hydrogels, which function as bioadhesives.

Example 33

Lap Shear Tensile Bond Strength of Polyvinylalcohol Acetoacetate and 4,9-Dioxa-1,12-Dodecanediamine (DODDA) on Regenerated Collagen Sheet

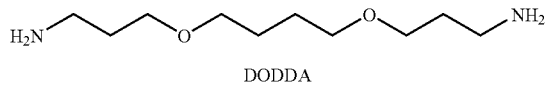 [SMILES: NCCCOCCCCOCCCN]

DODDA

Collagen strips were bonded together with PVOH acac and 4,9-dioxa-1,12-dodecanediamine (DODDA) and the lap shear tensile strength was determined. A 1-cm² area at the end of a 1 cm-wide×9 cm-long strip of damp collagen sheet was painted using quantities of each of the polyvinylalcohol acetoacetate and 4,9-dioxa-1,12-dodecanediamine solutions indicated in Table 24 below. The solutions were mixed well for 15 sec before overlapping a second collagen strip 1 cm at the end, lightly pressing and squirming the joint to establish a bond. The bonded collagen strips were kept moist between damp paper towels for 5 min and then tensile tested at 1.0 cm/min (0.4 inch per min). The results are summarized in Table 24 (1 psi=70.4 g/cm²).

Aqueous Solutions:
25 wt % PVOH acac (Mw=13-23 kDa; 3.5 mol % acac; eq wt=1350)
25 wt % PVOH acac (Mw=13-23 kDa; 10.0 mol % acac; eq wt=525)
25 wt % (88% hydrolyzed) PVOH acac (Mw=13-23 kDa; 6.5 mol % acac; eq wt=860)
25 wt % (80% hydrolyzed) PVOH acac (Mw=9-10 kDa; 7.4 mol % acac; eq wt=840)
20 wt % DODDA (4,9-dioxa-1,12-dodecanediamine; Aldrich #22,744-7; mw 204.32 Da; D=0.96; eq wt=102)

TABLE 24

PVOH acac-DODDA Lap Shear Tensile Test on Collagen

| Exp # | PVOH acac | PVOH acac eq wt | PVOH % hydrolyzed | DODDA | acac:NH₂ | PVOH:DODDA | Average g/cm² |
|---|---|---|---|---|---|---|---|
| 1* | 15 µL | 1350 | 99 | 2.0 µL | 1.0 | 10:1 | 60 ± 80 |
| 2† | 15 µL | 1350 | 99 | 2.0 µL | 1.0 | 10:1 | 236 ± 56 |
| 3 | 15 µL | 1350 | 99 | 4.0 µL | 0.5 | 6:1 | 45 ± 35 |
| 4 | 15 µL | 525 | 99 | 4.0 µL | 1.0 | 6:1 | 244 ± 70 |
| 5 | 15 µL | 525 | 99 | 7.5 µL | 0.5 | 4:1 | 190 ± 165 |
| 6 | 15 µL | 860 | 88 | 2.3 µL | 1.0 | 9:1 | 169 ± 46 |
| 7 | 15 µL | 860 | 88 | 4.5 µL | 0.5 | 5:1 | 305 ± 112 |
| 8 | 15 µL | 840 | 80 | 2.4 µL | 1.0 | 9:1 | 25 |
| 9† | 15 µL | 840 | 80 | 2.4 µL | 1.0 | 9:1 | 215 |
| 10 | 15 µL | 840 | 80 | 5.0 µL | 0.5 | 5:1 | 219 ± 73 |

*10-min cure time
†dampen collagen with pH 10 buffer before gluing

Most experiments were run in triplicate; the results are arranged in order of decreasing acac:amine ratio for the four different PVOH acac samples. Making the collagen surface basic (pH 10 buffer pre-treatment) greatly improved adhesion; compare experiments 1 vs. 2 and 8 Vs 9. It is thought that the base creates free $NH_2$ groups on the collagen protein surface to react with PVOH acetoacetate groups. This example demonstrates the ability of aqueous mixtures of various stoichiometry of polyvinylalcohol acetoacetate and 4,9-dioxa-1,12-dodecanediamine to react quickly to form hydrogels which function as bioadhesives.

Example 34

Sterilization of Aqueous Polyvinylalcohol Acetoacetate Solutions

Aqueous solutions (20-25 wt %) of polyvinylalcohol acetoacetate were sterilized by gamma irradiation under a flux of 25 kGy ($2.5 \times 10^6$ rad). The solutions were contained in glass vials or in sealed disposable syringes during irradiation. When the acetoacetate content was 5 mol % or less, the PVOH acac was stable to gamma irradiation. However, PVOH acac with higher acac content was found to crosslink under gamma irradiation, giving solutions that were more viscous or even rubbery.

A PVOH acetoacetate (12 mol % acac content) solution of 20 wt % could be thermally sterilized by autoclaving in an appropriate heat-resistant container such as a glass vial with a solid cap and a PTFE-faced silicone rubber cap liner at 121° C. for 15 min at temperature, plus heat up and cool down time totaling about 45 min. The solution was sterile and the viscosity remained the same as before sterilization. The solution reacted normally with amine crosslinkers to form hydrogels.

Aqueous PVOH 4-aminobutyral acetal solution (20 wt %), aqueous polyethyleneimine 600 (20-25 wt %), aqueous polyallylamine solutions (10-20 wt %) and neat 3-aminopropyltrimethoxysilane could be either gamma-sterilized under a flux of 25 kGy or thermally sterilized at 121° C. as described above.

This example illustrates the ease of sterilization of polyvinylalcohol acetoacetate solutions.

Example 35

Biocompatibility of Polyvinylalcohol Acetoacetate-Polyamine Hydrogels in Cell Cultures The safety of polyvinylalcohol acetoacetate-based hydrogels was demonstrated by challenging cell cultures with PVOH acac hydrogels derived from various crosslinking amines.

34-A. PVOH acac:

The testing was done using Chinese hamster ovary (CHO-K1) cell cultures according to ISO10993-5:1999, except that the cells were directly challenged with the materials. The Chinese hamster ovary (CHO-K1) cells were obtained from the American Type Culture Collection (ATCC), Manassas, Va., and were grown in F12-K medium supplemented with 10% fetal bovine serum.

The Chinese hamster ovary (CHO-K1) cell culture was challenged with an aqueous solution (12 wt %) of polyvinylalcohol acetoacetate (Mw=13-23 kDa; 5.4 mol % acac; eq wt=900). CHO-K1 cells were seeded in a culture plate at 55,000 cells per well and incubated with 1 mL culture medium for 24 hr; then 100 µL of PVOH acac solution was added, giving a final concentration of 11.8 mg/mL PVOH acac in the culture medium. The cytotoxicity was determined using the tetrazolium-based colorimetic assay (MTT), as described by Sgouras et al. (*Journal of Materials Science: Materials in Medicine* 1:61-68, 1990). As determined by this assay, there was no observable toxic effect on the cells.

A similar result was obtained with a 10 wt % solution of PVOH acac of lower eq wt. and higher Mw (Mw=31-50 kDa; 9.0 mol % acac; eq wt=575).

34-B. PVOH acac-PEI 600 Hydrogel:

The testing was done using NIH3T3 mouse fibroblast cell cultures according to ISO10993-5:1999. The NIH3T3 mouse fibroblast cells were obtained from ATCC and were grown in Dulbecco's modified essential medium (DMEM), supplemented with 10% fetal calf serum.

The NIH3T3 mouse fibroblast cell culture was challenged with a hydrogel made by combining 3 parts 25 wt % PVOH acac (Mw=13-23 kDa; 10.0 mol % acac; eq wt=525) with 1 part 25 wt % PEI 600 (polyethyleneimine Mn=600 Da, Aldrich #40, 871-9; eq wt~150). The hydrogel was coated on the bottom of a well in a polystyrene culture plate such that about ¼ of the well bottom was covered. The well was then sterilized under UV light and seeded with 50,000-100,000 NIH3T3 cells. The cells grew normally confluent and coated the well bottom, growing up to the edges of the hydrogel; they did not overgrow the hydrogel however. This demonstrates a lack of pronounced cytotoxicty on the part of the PVOH acac-PEI hydrogel.

A similar result was obtained with a hydrogel made from PVOH acac of higher eq wt (Mw=13-23 kDa; 3.5 mol % acac; eq wt=1350) with a 3:1 ratio of 25 wt % PVOH acac to 25 wt % PEI 600 as before. A similar result was also obtained with a hydrogel made from PVOH acac of higher Mw (Mw=31-50 kDa; 9.0 mol % acac; eq wt=575) with a 5:1 ratio of 25 wt % PVOH acac to 25 wt % PEI 600.

The following testing was done using J774 Macrophage cultures according to ISO10993-5:1999. The J774 Macrophage cells were obtained from ATCC and were grown in DMEM supplemented with 10% fetal bovine serum.

The J774 mouse peritoneal macrophage cell culture was challenged with a hydrogel made by combining 10 parts 20 wt % PVOH acac (Mw=31-50 kDa; 10.4 mol % acac; eq wt=510) with 1 part 20 wt % PEI 600 (polyethyleneimine Mn=600 Da, Aldrich #40,871-9; eq wt~150). The hydrogel was coated on the bottom of a well in a polystyrene culture plate such that about ¼ of the well bottom was covered. The well was then sterilized under UV light and seeded with J774 cells. The cell culture was then analyzed for TNF-α, an indicator of inflammatory response, using an ELISA assay, as described by Lara et al. (*Journal of Dental Research* 82(6): 460-465, 2003). The TNF-α titer was similar to the negative control (a blank well), indicating the non-inflammatory nature of the PVOH acac-PEI hydrogel.

34-C. PVOH acac-APS Hydrogel:

An NIH3T3 mouse fibroblast cell culture was challenged with a hydrogel made by combining 50 parts 20 wt % PVOH acac (Mw=31-50 kDa; 5.4 mol % acac; eq wt=900) with 1 part neat 3-aminopropyltrimethoxysilane (APS; Aldrich #28, 177-8; eq wt=mw=179 Da). The hydrogel was coated on the bottom of a well in a polystyrene culture plate such that about ¼ of the well bottom was covered. The well was then sterilized under UV light and seeded with 50,000-100,000 NIH3T3 cells. The cells grew normally confluent and coated the well bottom, growing up to the edges of the hydrogel; they did not overgrow the hydrogel however. This demonstrates a lack of pronounced cytotoxicty on the part of the PVOH acac-APS hydrogel.

A J774 mouse peritoneal macrophage cell culture was challenged with a hydrogel made by combining 10 parts 20 wt % PVOH acac (Mw=31-50 kDa; 10.4 mol % acac; eq wt=510) with 1 part neat 3-aminopropyltrimethoxysilane (APS; Aldrich #28,177-8; eq wt=mw=179 Da). The hydrogel was coated on the bottom of a well in a polystyrene culture plate such that about ¼ of the well bottom was covered. The well was then sterilized under UV light and seeded with J774 cells. The cell culture was then analyzed for TNF-α, an indicator of inflammatory response, as described above. The TNF-α titer was similar to the negative control (a blank well), indicating the non-inflammatory nature of the PVOH acac-APS hydrogel.

34-D. PVOH acac-PVOH 4-Aminobutyral Acetal Hydrogel:

An NIH3T3 mouse fibroblast cell culture was challenged with a hydrogel made by combining 4 parts 20 wt % PVOH acac (Mw=31-50 kDa; 10.4 mol % acac; eq wt=510) with 5 parts 20 wt % PVOH 4-aminobutyral acetal (Mw=31-50 kDa; eq wt=630). The hydrogel was coated on the bottom of a well in a polystyrene culture plate such that about ¼ of the well bottom was covered. The well was then sterilized under UV light and seeded with 50,000-100,000 NIH3T3 cells. The cells grew normally confluent and coated the well bottom, growing up to the edges of the hydrogel; they did not overgrow the hydrogel however. This demonstrates a lack of pronounced cytotoxicty on the part of the PVOH acac-PVOH amine hydrogel.

A J774 mouse peritoneal macrophage cell culture was challenged with a hydrogel made by combining 4 parts 20 wt % PVOH acac (Mw=31-50 kDa; 10.4 mol % acac; eq wt=510) with 5 parts 20 wt % PVOH 4-aminobutyral acetal (Mw=31-50 kDa; eq wt=630). The hydrogel was coated on the bottom of a well in a polystyrene culture plate such that about ¼ of the well bottom was covered. The well was then sterilized under UV light and seeded with J774 cells. The cell culture was then analyzed for TNF-α, an indicator of inflammatory response, as described above. The TNF-α titer was similar to the negative control (a blank well), indicating the non-inflammatory nature of the PVOH acac-PVOH amine hydrogel.

34-E. PVOH acac-Poly(Vinyl Alcohol-Co-Vinylamine):

An NIH3T3 mouse fibroblast cell culture was challenged with a hydrogel made by combining 1 part 20 wt % PVOH acac (Mw=31-50 kDa; 5.4 mol % acac; eq wt=900) with 1 part 15 wt % PVOH-VNH2 (8.5 mol % $NH_2$ eq wt=520). The hydrogel was coated on the bottom of a well in a polystyrene culture plate such that about ¼ of the well bottom was covered. The well was then sterilized under UV light and seeded with 50,000-100,000 NIH3T3 cells. The cells grew normally confluent and coated the well bottom, growing up to the edges of the hydrogel; they did not overgrow the hydrogel however. This demonstrates a lack of pronounced cytotoxicty on the part of the PVOH acac-PVOH-VNH2 hydrogel.

This example illustrates the safety of polyvinylalcohol acetoacetate-based hydrogels.

Example 36

Painting Rabbit Intestines In Vivo with Polyvinylalcohol Acetoacetate Hydrogels

The safety of polyvinylalcohol acetoacetate-based hydrogels was further demonstrated by "painting" a patch of hydrogel onto the small intestine of a living rabbit. The animal was sewn up and fed normally and was sacrificed 3 days later. The intestinal and adjoining tissues under and around the hydrogel adhesive patch were examined for inflammation.

Application Technique:

Albino New Zealand rabbits (9 months old; ~4 kg in weight) were fasted overnight. Prior to surgery, the animals were treated with buprenorphine, and then anaesthetized with a mixture of ketamine and xylazine. A standard laparotomy procedure was performed to isolate a section of the duodenum of the small intestine. A single "marker" stitch of blue-dyed polypropylene suture material was placed in the small intestine in the outer layer of intestinal tissue about 10 cm distal from the stomach. This was done to aid in locating the hydrogel patch at necropsy. A patch of hydrogel about 1 cm×2 cm was applied to the small intestine about 5 cm distal from the stomach in the following manner. The plunger of a sterile 3 mL disposable syringe with the Luer end cut off was lowered about ½ inch and the sterile PVOH acac and crosslinking amine solutions were introduced into the barrel and stirred vigorously with a thin spatula for 10 sec or until the mixture began to gain noticeable viscosity. The viscous fluid mixture was then delivered onto the tissue surface by pushing out with the plunger and quickly spreading with the spatula. The patch was allowed to cure for 2-3 min and then the peritoneum and abdomen were closed in layers using standard surgical procedure. The intestine surface was covered about 75% of the way around, leaving the mesentery uncovered.

35-A. PVOH acac-PEI 600 Hydrogel:

The tissue surface was "primed" by lightly rubbing with a cotton swab that was wetted with 20 wt % aqueous dextran aldehyde (48% conversion of saccharide rings to dialdehydes; Mw=10 kDa) before adhesive application. Then a mixture of 0.20 mL 20 wt % aqueous PVOH acac (Mw=31-50 kDa; 9.0 mol % acac; eq wt=575) and 20 µL 20 wt % aqueous PEI 600 (polyethyleneimine Mn=600 Da; Aldrich #40,871-9; EW~150) was applied to the area as described above and allowed to cure for 2 min before closing. Five rabbits were treated in this way.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed good adhesion of the hydrogel adhesive in all cases and no observable inflammation. There were very few fibrous adhesions, generally on the surface around the margins of the adhesive patch, and these were small; there was no attachment to adjacent tissue. There was also no apparent swelling or deterioration of the polymer coating. In all cases, intestinal peristalsis could easily move past the adhesive site.

35-B. PVOH acac-APS Hydrogel:

The tissue surface was "primed" by lightly rubbing with a cotton swab that was wetted with 20 wt % aqueous dextran aldehyde (48% conversion of saccharide rings to dialdehydes; Mw=10 kDa) before adhesive application. Then a mixture of 0.20 mL 20 wt % aqueous PVOH acac (Mw=31-50 kDa; 10.4 mol % acac; eq wt=510) and 6 µL neat 3-aminopropyltrimethoxysilane (APS, Aldrich #28,177-8) was applied to the area as described above and allowed to cure for 2 min before closing. Five rabbits were treated in this way.

At necropsy 3 days later, the adhesive application site was examined for gross tissue responses and the presence of the adhesive, as described above. There was good adhesion of the hydrogel in all cases and no observable inflammation. There were no fibrous adhesions. There was also little swelling or deterioration of the polymer coating.

35-C. PVOH acac-PVOH 4-Aminobutyral Acetal Hydrogel:

The tissue surface was "primed" by lightly rubbing with a cotton swab that was wetted with 20 wt % aqueous dextran aldehyde (48% conversion of saccharide rings to dialdehydes; Mw=10 kDa) before adhesive application. Then a mixture of 0.20 mL 20 wt % aqueous PVOH acac (Mw=31-50 kDa; 10.4 mol % acac; eq wt=510) and 0.15 mL 20 wt % Na$_2$CO$_3$-neutralized polyvinylalcohol 4-aminobutyral acetal (Mw=31-50 kDa; eq wt=630) was applied to the area as described above (after mixing vigorously for about 30-45 sec) and allowed to cure for 3 min before closing. Five rabbits were treated in this way.

At necropsy 3 days later, the adhesive application site was examined for gross tissue responses and the presence of the adhesive, as described above. There was good adhesion of the hydrogel in all cases and no apparent inflammation. There were some fibrous adhesions in the latter three experiments that appeared to involve the marker stitch. Possibly the stitch contacted and stuck in the soft adhesive, giving rise to fibrous adhesion formation. There was little swelling or deterioration of the polymer coating.

This example further illustrates the safety of polyvinylalcohol acetoacetate-based hydrogels.

Example 37

Sealing a Rabbit Enterotomy In Vivo with a Polyvinylalcohol Acetoacetate-Polyethyleneimine Hydrogel The safety and efficacy of a polyvinylalcohol acetoacetate-polyethyleneimine hydrogel was further demonstrated by sealing around the suture line of an enterotomy incision in the small intestine of a living rabbit. Albino New Zealand rabbits (~4 kg) were used as above in Example 36. A 5-mm incision was made about 10 cm distal from the stomach and the incision was closed with two 5-0 Vicryl sutures. The tissue surface on and around the sutures was "primed" by lightly rubbing with a cotton swab that was wetted with 20 wt % aqueous dextran aldehyde (48% conversion of saccharide rings to dialdehydes; Mw=10 kDa) before adhesive application. Then a mixture of 0.30 mL 20 wt % aqueous PVOH acac (Mw=31-50 kDa; 10.4 mol % acac; eq wt=510) and 30 μL 20 wt % aqueous PEI 600 (polyethyleneimine Mn=600 Da; Aldrich #40,871-9; EW~150) was applied to the area, as described above in Example 36, and allowed to cure for 3 min before closing. Five rabbits were treated in this way.

Significant bleeding caused difficulty in applying the hydrogel adhesive in some cases; in one rabbit in particular; continual bleeding washed away the dextran aldehyde primer before the adhesive could be applied. Bleeding was eventually stopped by the adhesive in all cases, but in at least one case it compromised the bioadhesive patch.

Over the next 3 days all 5 rabbits survived, fed and passed feces normally. Examination at necropsy after 3 days revealed good hydrogel adhesion and little visible tissue inflammation in 4 of 5 rabbits. The incision site in the fifth rabbit was inflamed, weak and unhealed; this was attributed to poor adhesive curing due to excessive bleeding at the application site. It is to be expected that if the blood vessels in this fifth rabbit were cauterized, this site would have been adequately sealed as well.

This example demonstrates the safety and efficacy of the PVOH acac-PEI hydrogel bioadhesive for sealing sutures in intestinal incisions.

What is claimed is:
1. A method for applying a coating to an anatomical site on tissue of a living organism comprising:
(a) optionally priming said anatomical site with an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said aqueous solution containing from about 2% to about 40% by weight of the oxidized polysaccharide;
(b) applying to said anatomical site a first component comprising an aqueous solution comprising
(i) at least one poly(hydroxylic) compound derivatized with acetoacetate groups selected from the group consisting of
at least one poly(vinyl alcohol) derivatized with acetoacetate groups;
at least one poly(vinyl alcohol) copolymer derivatized with acetoacetate groups wherein said poly(vinyl alcohol) copolymer comprises between about 1 mole percent and about 25 mole percent of the comonomer relative to the vinyl alcohol units;
at least one linear or branched poly(ether) derivatized with acetoacetate groups;
at least one polysaccharide derivatized with acetoacetate groups;
at least one low molecular weight polyol derivatized with acetoacetate groups wherein said low molecular weight polyol has at least two hydroxy groups and has a molecular weight of less than about 300 Daltons;
at least one hydrolyzed polyvinyl acetate-methyl acrylate copolymer derivatized with acetoacetate groups;
at least one monosaccharide derivatized with acetoacetate groups;
at least one reduced monosaccharide derivatized with acetoacetate groups;
at least one polyether condensation product derivatized with acetoacetate groups wherein said polyether condensation product is produced by reacting at least one core molecule bearing more than one carboxylic acid group thereon with a sufficient amount of at least one polyether terminated with hydroxy groups to produce an esterified polyether with an average of at least two hydroxy end groups; and mixtures thereof
and/or
(ii) a first polyamino compound derivatized with acetoacetamide groups selected from group consisting of amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), and mixtures thereof;
each of (i) or (ii) having a weight-average molecular weight of less than about 200,000 Daltons and having an equivalent weight per acetoacetate group or acetoacetamide group, respectively, of about 100 to about 2000 Daltons; and
(c) applying to said anatomical site a second component comprising at least one of
(iii) an aqueous solution of at least one second polyamino compound, wherein said at least one second polyamino compound has an equivalent weight per amino group of about 100 to about 1,000 Daltons

(iv) at least one 3-aminopropyltrialkoxysilane, 3-aminopropyldialkoxyalkylsilane or 3-aminopropylmonoalkoxydialkylsilane, neat or in aqueous solution, and (v) an aqueous solution of at least one second polyamino compound and at least one 3-aminopropyltrialkoxysilane, 3-aminopropyldialkoxyalkylsilane or 3-aminopropylmonoalkoxydialkylsilane; and (d) mixing said components on the surface of said anatomical site; or (e) applying said second component to said anatomical site, followed by said first component, followed by mixing the solutions on the surface of said anatomical site; or (f) premixing said first and second components, and applying the resulting mixture to said anatomical site before said resulting mixture completely cures;

wherein the acetoacetate and/or acetoacetamide groups of step (b) react at ambient temperature with the amine groups of step (c) to form a hydrogel.

2. The method as recited in claim 1, wherein said poly (vinyl alcohol) has a weight-average molecular weight in the range of from about 10,000 Daltons to about 50,000 Daltons.

3. The method as recited in claim 1, wherein the degree of hydrolysis of said poly(vinyl alcohol) is from about 60% to about 100% OH groups, the balance being acetate groups.

4. The method as recited in claim 1, wherein said at least one second polyamino compound is selected from the group consisting of amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), linear or branched poly (ethyleneimine), poly(allylamine), poly(lysine), poly(vinyl alcohol) derivatized with 4-aminobutyral acetal groups, poly (vinyl alcohol-co-vinylamine), linear or branched diaminoalkanes in the weight average molecular weight range of from about 80 Daltons to about 300 Daltons, 4,9-dioxa-1,12-dodecanediamine, N,N'-bis(3-aminopropyl)piperazine, 5-amino-1,3,3-trimethylcyclohexanemethylamine, 1,3-bis(aminomethyl)cyclohexane, 1,4-diaminocyclohexane, xylylenediamine, adipic dihydrazide, (hydrazidocarboxymethyl)-terminated linear or branched poly(ethylene oxide), (hydrazidocarboxymethyl)-terminated linear or branched poly(propylene oxide), (hydrazidocarboxymethyl)-terminated linear or branched poly(ethylene oxide)-poly(propylene oxide) copolymer, (hydrazidocarboxymethyl)-terminated linear or branched poly(1,3-trimethylene oxide), (hydrazidocarboxymethyl)-terminated linear or branched poly(1,4-tetramethylene oxide), spermine, spermidine, dendrimeric amino-terminated copoly(ethylenediaminetetrapropionic acid-ethylenediamine) poly(amidoamines), and mixtures thereof.

5. The method as recited in claim 1, wherein the concentration of poly(hydroxylic) compound derivatized with acetoacetate groups in the aqueous solution of (b) is from about 15% to about 30% by weight.

6. The method as recited in claim 1, wherein the concentration of said second polyamino compound in the aqueous solution of (c) is about 15% to about 30% by weight.

7. The method as recited in claim 1, wherein the weight-average molecular weight of said oxidized polysaccharide is from about 3,000 to about 250,000 Daltons.

8. The method as recited in claim 1, wherein said oxidized polysaccharide is selected from the group consisting of dextran, chitin, starch, agar, cellulose, and hyaluronic acid.

9. The method as recited in claim 1, wherein said aqueous solutions and said at least one neat 3-aminopropyltrialkoxysilane, 3-aminopropyldialkoxyalkylsilane or 3-aminopropylmonoalkoxydialkylsilane are sterilized.

10. The method as recited in claim 1, wherein said aqueous solution of (b) further comprises at least one oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said aqueous solution containing from about 2% to about 20% by weight of the oxidized polysaccharide.

11. The method as recited in claim 10, wherein said oxidized polysaccharide is selected from the group consisting of dextran, chitin, starch, agar, cellulose, and hyaluronic acid.

12. The method as recited in claim 1 wherein said anatomical site is on an intestine or blood vessel and the method is used in an anastomosis procedure.

13. The method as recited in claim 1 wherein at least one of said aqueous solutions further comprises a pharmaceutical drug or therapeutic agent and said method is used for drug delivery to the anatomical site.

14. A method for bonding at least two anatomical sites together comprising:

(a) optionally priming at least one anatomical site with an aqueous solution comprising an oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said aqueous solution containing from about 2% to about 40% by weight of the oxidized polysaccharide;

(b) applying a first component to at least one anatomical site comprising an aqueous solution comprising (i) at least one poly(hydroxylic) compound derivatized with acetoacetate groups selected from the group consisting of at least one poly(vinyl alcohol) derivatized with acetoacetate groups;

at least one poly(vinyl alcohol) copolymer derivatized with acetoacetate groups wherein said poly(vinyl alcohol) copolymer comprises between about 1 mole percent and about 25 mole percent of the comonomer relative to the vinyl alcohol units;

at least one linear or branched poly(ether) derivatized with acetoacetate groups;

at least one polysaccharide derivatized with acetoacetate groups;

at least one low molecular weight polyol derivatized with acetoacetate groups wherein said polyol has at least two hydroxy groups and has a molecular weight of less than about 300 Daltons;

at least one hydrolyzed polyvinyl acetate-methyl acrylate copolymer derivatized with acetoacetate groups;

at least one monosaccharide derivatized with acetoacetate groups;

at least one reduced monosaccharide derivatized with acetoacetate groups;

at least one polyether condensation product derivatized with acetoacetate groups wherein said polyether condensation product is produced by reacting at least one core molecule bearing more than one carboxylic acid group thereon with a sufficient amount of at least one polyether terminated with hydroxy groups to produce an esterified polyether with an average of at least two hydroxy end groups; and mixtures thereof and/or (ii) a first polyamino compound derivatized with acetoacetamide groups, amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), and mixtures thereof each of (i) or (ii) having a weight-average molecular weight of less than about 200,000 Daltons and having an equivalent weight per acetoacetate group or acetoacetamide group, respectively, of about 100 to about 2000 Daltons;

(c) applying to said at least one anatomical site a second component comprising at least one of (iii) an aqueous solution of at least one second polyamino compound, wherein said polyamino compound has an equivalent weight per amino group of about 100 to about 1,000 Daltons;

(iv) at least one 3-aminopropyltrialkoxysilane, 3-aminopropyldialkoxyalkylsilane or 3-aminopropylmonoalkoxydialkylsilane, neat or in aqueous solution; and (v) an aqueous solution of at least one polyamino compound and at least one 3-aminopropyltrialkoxysilane, 3-aminopropyldialkoxyalkylsilane or 3-aminopropylmonoalkoxydialkylsilane;

(d) mixing said components on the surface of said at least one anatomical site; or (e) applying said second component to said at least one anatomical site, followed by said first component, followed by mixing the solutions on the surface of said at least one anatomical site; or (f) premixing said first and second components, and applying the resulting mixture to said at least one anatomical site before said resulting mixture completely cures; wherein the acetoacetate and/or acetoacetamide groups of step (b) react at ambient temperature with the amine groups of step (c) to form a hydrogel, and (g) contacting said at least two anatomical sites together.

15. The method as recited in claim 14, wherein polyvinyl alcohol) has a weight-average molecular weight in the range of from about 10,000 Daltons to about 50,000 Daltons.

16. The method as recited in claim 14, wherein the degree of hydrolysis of said poly(vinyl alcohol) is from about 60% to about 100% OH groups, the balance being acetate groups.

17. The method as recited in claim 14, wherein said second polyamino compound is selected from the group consisting of amino-terminated linear or branched poly(ethylene oxide), amino-terminated linear or branched poly(propylene oxide), amino-terminated linear or branched copolymers of poly(ethylene oxide) and poly(propylene oxide), amino-terminated linear or branched poly(1,3-trimethylene oxide), amino-terminated linear or branched poly(1,4-tetramethylene oxide), amino-terminated star poly(ethylene oxide), amino-terminated comb poly(ethylene oxide), amino-terminated star poly(propylene oxide), amino-terminated comb poly(propylene oxide), linear or branched poly(ethyleneimine), poly(allylamine), poly(lysine), poly(vinyl alcohol) derivatized with 4-aminobutyral acetal groups, poly(vinyl alcohol-co-vinylamine), linear or branched diaminoalkanes in the weight average molecular weight range of from about 80 Daltons to about 300 Daltons, 4,9-dioxa-1,12-dodecanediamine, N,N'-bis(3-aminopropyl)piperazine, 5-amino-1,3,3-trimethylcyclohexanemethylamine, 1,3-bis(aminomethyl)cyclohexane, 1,4-diaminocyclohexane, xylylenediamine, adipic dihydrazide, (hydrazidocarboxymethyl)-terminated linear or branched poly(ethylene oxide), (hydrazidocarboxymethyl)-terminated linear or branched poly(propylene oxide), (hydrazidocarboxymethyl)-terminated linear or branched poly(ethylene oxide)-poly(propylene oxide) copolymer, (hydrazidocarboxymethyl)-terminated linear or branched poly(1,3-trimethylene oxide), (hydrazidocarboxymethyl)-terminated linear or branched poly(1,4-tetramethylene oxide), spermine, spermidine, dendrimeric amino-terminated copoly(ethylenediaminetetrapropionic acid-ethylenediamine) poly(amidoamines), and mixtures thereof.

18. The method as recited in claim 14, wherein the concentration of the poly(hydroxylic) compound derivatized with acetoacetate groups in the aqueous solution of (b) is from about 15% to about 30% by weight.

19. The method as recited in claim 14, wherein the concentration of said second polyamino compound in the aqueous solution of (c) is about 15% to about 30% by weight.

20. The method as recited in claim 14, wherein said aqueous solution of (b) further comprises at least one oxidized polysaccharide containing aldehyde groups, having a weight-average molecular weight of about 1,000 to about 1,000,000 Daltons, said oxidized polysaccharide having an equivalent weight per aldehyde group of about 90 to about 1500 Daltons, said aqueous solution containing from about 2% to about 20% by weight of the oxidized polysaccharide.

21. The method as recited in claim 20, wherein said oxidized polysaccharide is selected from the group consisting of dextran, chitin, starch, agar, cellulose, and hyaluronic acid.

* * * * *